(12) United States Patent
Feng et al.

(10) Patent No.: US 10,000,512 B2
(45) Date of Patent: Jun. 19, 2018

(54) COMPOUNDS FOR THE TREATMENT OF INFECTIOUS DISEASES

(71) Applicant: Hoffmann-La Roche Inc., Little Falls, NJ (US)

(72) Inventors: Song Feng, Shanghai (CN); Haixia Liu, Shanghai (CN); Guolong Wu, Shanghai (CN); Hongying Yun, Shanghai (CN); Dongdong Chen, Shanghai (CN); Chao Li, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days. days.

(21) Appl. No.: 15/484,015

(22) Filed: Apr. 10, 2017

(65) Prior Publication Data

US 2017/0217990 A1    Aug. 3, 2017

Related U.S. Application Data

(63) Continuation of application No. PCT/EP2015/073202, filed on Oct. 8, 2015.

(30) Foreign Application Priority Data

Oct. 11, 2014  (WO) ............... PCT/CN2014/088404
Jul. 31, 2015  (WO) ............... PCT/CN2015/085653

(51) Int. Cl.
| | |
|---|---|
| *A01N 43/90* | (2006.01) |
| *A61K 31/519* | (2006.01) |
| *C07D 239/00* | (2006.01) |
| *C07D 471/00* | (2006.01) |
| *C07D 487/00* | (2006.01) |
| *C07D 491/00* | (2006.01) |
| *C07D 513/04* | (2006.01) |

(52) U.S. Cl.
CPC .......... *C07D 513/04* (2013.01); *A61K 31/519* (2013.01)

(58) Field of Classification Search
None
See application file for complete search history.

(56) References Cited

U.S. PATENT DOCUMENTS

2008/0020989 A1    1/2008  Haley et al.

FOREIGN PATENT DOCUMENTS

| WO | 2006/066080 A1 | 6/2006 |
|---|---|---|
| WO | 2010048549 A2 | 4/2010 |
| WO | 2010108140 A1 | 9/2010 |
| WO | 2013009737 A1 | 1/2013 |

OTHER PUBLICATIONS

Jin et al., "Diastereoselective Synthesis of the Potent Antiviral Agent (−)-2'-Deoxy-3'-thiacytidine and Its Enantiomer" J Org Chem 60(8):2621-2623 (Apr. 1995).
Kano et al., "Direct Asymmetric Benzoyloxylation of Aldehydes Catalyzed by 2-Tritylpyrrolidine" J Am Chem Soc 131(10):3450-3451 (Feb. 19, 2009).

*Primary Examiner* — Jeffrey H Murray
(74) *Attorney, Agent, or Firm* — Jonathan Duffield

(57) ABSTRACT

The present invention relates to compounds of formula (I),

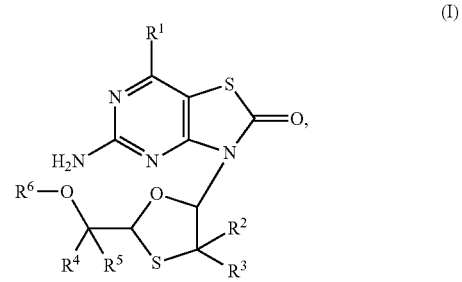

wherein $R^1$, $R^2$, $R^3$, $R^4$, $R^5$ and $R^6$ are as described herein, and their prodrugs or pharmaceutically acceptable salt, enantiomer or diastereomer thereof, and compositions including the compounds and methods of using the compounds.

21 Claims, 2 Drawing Sheets

COMPOUNDS FOR THE TREATMENT OF INFECTIOUS DISEASES

CROSS REFERENCE TO RELATED APPLICATIONS

This application is a continuation of International Application No. PCT/EP2015/073202, filed Oct. 8, 2015, which application claims the benefit of prirotiy to International Application PCT/CN2015/085653, filed Jul. 31, 2015, and to International Application PCT/CN2014/088404, filed Oct. 11, 2014, all of which applications are hereby incorporated by reference.

FIELD OF THE INVENTION

The present invention relates to novel 3-substituted 5-amino-6H-thiazolo[4,5-d]pyrimidine-2,7-dione compounds, that have Toll-like receptor agonism activity and their prodrugs thereof, as well as their manufacture, pharmaceutical compositions containing them and their potential use as medicaments.

BACKGROUND OF THE INVENTION

Toll-like receptors (TLRs) are a family of evolutionarily conserved pattern recognition receptors (PRRs) expressed by a variety of cell types, particularly those of the innate immune system such as dendritic cells and monocytes. The innate immune system can recognize pathogen-associated molecular patterns (PAMP) via these TLRs expressed on the cell surface of certain types of immune cells. Recognition of foreign pathogens activates the production of cytokines and up-regulation of co-stimulatory molecules on phagocytes. This leads to the modulation of T cell and B cell behaviour (D. J Connolly and L. A J O'Neill, Current Opinion in Pharmacology 2012, 12:510-518).

Toll-like receptor 7 (TLR7) is a member of this receptor class that is found predominantly in the endosomal compartment of plasmacytoid dendritic cells (pDCs), which are the primary source of interferon-α (IFN-α). The receptor is also expressed at significant levels in B cells. The native ligand for TLR7 is single-stranded RNA, particularly of viral origin. Following the binding of ssRNA to TLR7, the receptor in its dimer form is believed to undergo a structural change leading to subsequent recruitment of adaptor proteins, including MyD88, to the cytoplasmic domain and initiation of the receptor signalling cascade. This alternation results in the activation of cytoplasmic transcription factors, including IRF-7 and NF-κB, that undergo translocation to the nucleus and initiate transcription of various genes, e.g., IFN-α and other antiviral cytokine genes. The altered responsiveness of pDCs might contribute to the reduced innate immune responses during chronic viral infections. Agonist-induced activation of TLR7 might therefore represent a novel approach for the treatment of chronic viral infections (P. A. Roethle et al, J. Med. Chem. 2013, 56, 7324-7333).

Agonists of TLR7 mediate antiviral activity against a variety of viruses due to the production of endogenous interferons and other antiviral cytokines, and by induction of an antiviral immune response. Pegylated IFN-α (PEG-IFN-α) is currently used to treat chronic HBV and is an alternative to potentially life-long treatment with antiviral nucleos(t)ide analogues. In a subset of chronic HBV patients, PEG-IFN-α therapy can induce sustained immunologic control of the virus following a finite duration of therapy. However, the percentage of HBV patients that achieve seroconversion with interferon therapy is low (up to 27% for HBeAg-positive patients) and the treatment is typically poorly tolerated. Furthermore, functional cure (defined as HBsAg loss and seroconversion) is also very infrequent with both PEG-IFN-α and nucleos(t)ide treatment. Given these limitations, there is an urgent need for improved therapeutic options to treat and induce a functional cure for chronic HBV. Treatment with an oral, small-molecule TLR7 agonist is a promising approach that has the potential to provide greater efficacy and tolerability (T. Asselah et al, Clin Liver Dis 2007, 11, 839-849).

A number of identified TLR7 agonists have demonstrated anti-viral properties. For example, the TLR7 agonist imiquimod (ALDARA™) was approved by the U.S. FDA as a topical agent for the treatment of skin lesions caused by certain strains of the human papillomavirus. The TLR7/8 agonist resiquimod (R-848) is being evaluated as a topical agent for the treatment of human genital herpes. 852A, a TLR7 agonist, has shown promise in Phase I trials in cancer patients. This compound has also completed a Phase II trial for the treatment of chemotherapy-refractory metastatic melanoma. Another compound, ANA773 is an oral pro-drug TLR7 agonist, developed for the treatment of patients with chronic hepatitis C virus (HCV) infection and cancer (A. X. Xiang et al, Nucleosides, Nucleotides, and Nucleic Acids, 26:635-640, 2007). GS-9620 is an orally available TLR7 agonist. A phase Ib study demonstrated that treatment with GS-9620 was safe, well tolerated and resulted in significant dose-dependent ISG15 mRNA induction in patients with chronic hepatitis B (E. J. Gane et al, Annu Meet Am Assoc Study Liver Dis (November 1-5, Washington, D.C.) 2013, Abst 946). Therefore there are high unmet clinical needs for developing high potent and safe TLR7 agonists as new HBV treatment to offer more therapeutic solutions or replace existing partly effective treatment.

FIELD OF THE INVENTION

The present invention provides a series of novel 3-substituted 5-amino-6H-thiazolo[4,5-d]pyrimidine-2,7-dione compounds, that have Toll-like receptor agonism activity and their prodrugs. The invention also provides the bioactivity of such compounds to induce SEAP level increase by activating Toll-like receptors, such as TLR7 receptor, the metabolic conversion of prodrugs to parent compounds in the presence of cynomolgus monkey hepatocytes and human hepatocytes, and the therapeutic or prophylactic use of such compounds and their pharmaceutical compositions comprising these compounds and their prodrugs to treat or prevent infectious disease like HBV or HCV or disorders associated with Toll-like receptors modulation, such as TLR7 receptor.

The present invention relates to compounds of formula (I),

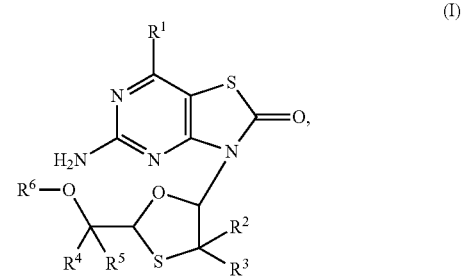

and the prodrugs of formula (Ia), (Ia)

wherein $R^1$ to $R^{11}$ are described below, or pharmaceutically acceptable salt, enantiomer or diastereomer thereof.

SUMMARY OF THE INVENTION

The present invention relates to novel compounds of formula (I)

(I)

wherein
$R^1$ is hydroxy;
$R^2$ and $R^3$ are independently selected from hydrogen, $C_{2-6}$alkenyl and $C_{1-6}$alkyl;
$R^4$ and $R^5$ are independently selected from hydrogen, $C_{1-6}$alkyl, $C_{3-7}$cycloalkyl, $C_{3-7}$ cycloalkyl$C_{2-6}$alkynyl, $C_{2-6}$alkenyl, $C_{2-6}$alkynyl and 2-thiophenyl;
$R^6$ is hydrogen or $C_{1-6}$alkylcarbonyl;
or pharmaceutically acceptable salt, enantiomer or diastereomer thereof.

The present invention also relates to the prodrugs of formula (Ia), (Ia)

wherein
$R^7$ and $R^8$ are hydrogen;
$R^9$ and $R^{19}$ are independently selected from hydrogen, $C_{2-6}$alkynyl and $C_{3-7}$cycloalkyl;
$R^{11}$ is hydrogen or $C_{1-6}$alkylcarbonyl;
or pharmaceutically acceptable salt, enantiomer or diastereomer thereof.

The invention is also relates to their manufacture, medicaments based on a compound in accordance with the invention and their production as well as the use of compounds of formula (I) or prodrugs thereof as TLR7 agonist. Accordingly, the compounds of formula (I) or prodrugs of formula (Ia) are useful for the treatment or prophylaxis of HBV and/or HCV infection with Toll-like receptors agonism.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.
Definitions As used herein, the term "$C_{1-6}$alkyl" signifies a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "$C_{1-6}$alkyl" groups are methyl, ethyl, n-propyl, isopropyl, n-butyl and isobutyl.

The term "$C_{2-6}$alkenyl" signifies an unsaturated, linear or branched chain alkenyl group containing 2 to 6, particularly 2 to 4 carbon atoms, for example vinyl, propenyl, allyl, butenyl and the like. Particular "$C_{2-6}$alkenyl" group is allyl.

The term "$C_{2-6}$alkynyl" signifies an unsaturated, linear or branched chain alkynyl group containing 2 to 6, particularly 2 to 4 carbon atoms, for example ethynyl, 1-propynyl, propargyl, butynyl and the like. Particular "$C_{2-6}$alkynyl" groups are ethynyl, 1-propynyl and propargyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclobutyl and cyclohexyl.

The term "$C_{3-7}$cycloalkylalkynyl" refers to alkynyl substituted by $C_{3-7}$cycloalkyl, wherein the "$C_{3-7}$cycloalkyl" is as defined above. Particular "$C_{3-7}$cycloalkylalkynyl" group is 2-cyclopropylethynyl.

The term "carbonyl" alone or in combination refers to the group —C(O)—.

The term "$C_{1-6}$alkylcarbonyl" refers to a group $C_{1-6}$alkyl-C(O)—, wherein the "$C_{1-6}$alkyl" is as defined above. Particular "$C_{1-6}$alkylcarbonyl" group is acetyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) and their prodrugs which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The compounds of the invention may exhibit the phenomenon of tautomerism. While the formula drawings cannot expressly depict tall possible tautomeric forms, it is to be understood they are intended to represent any tautomeric form of the depicted compound and are not to be limited merely to a specific compound form depicted by the formula drawings. For example, it is understood for formula (II) that regardless of whether or not the substituents are shown in their enol or their keto form, they represent the same compound (as shown in the example below).

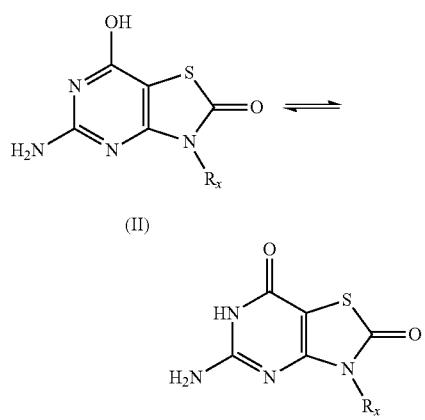

(II)

$R_x$ refers to any feasible substituent.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form. As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.). Additionally, compounds and prodrugs of formula (I), and other compounds of the invention are intended to cover solvated as well as unsolvated forms of the identified structures. For example, formula (I) includes compounds of the indicated structure in both hydrated and non-hydrated forms. Other examples of solvates include the structures in combination with isopropanol, ethanol, methanol, DMSO, ethyl acetate, acetic acid, or ethanolamine.

The term "prodrug" denotes a form or derivative of a compound which is metabolized in vivo, e.g., by biological fluids or enzymes by a subject after administration, into a pharmacologically active form of the compound in order to produce the desired pharmacological effect. Prodrugs are described e.g. in "The Organic Chemistry of Drug Design and Drug Action", by Richard B. Silverman, Academic Press, San Diego, 2004, Chapter 8 Prodrugs and Drug Delivery Systems, pp. 497-558.

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

TLR7 Agonist and Prodrug

The present invention relates to (i) a compound of formula (I):

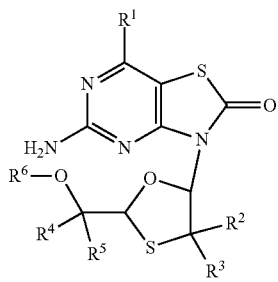

(I)

wherein
$R^1$ is hydroxy;
$R^2$ and $R^3$ are independently selected from hydrogen, $C_{2-6}$alkenyl, $C_{3-7}$cycloalkyl and $C_{1-6}$alkyl;
$R^4$ and $R^5$ are independently selected from hydrogen, $C_{1-6}$alkyl, $C_{3-7}$cycloalkyl, $C_{3-7}$cycloalkyl$C_{2-6}$alkynyl, $C_{2-6}$alkenyl, $C_{2-6}$alkynyl, phenyl and thiophenyl;
$R^6$ is hydrogen, $C_{1-6}$alkoxylcarbonyl or $C_{1-6}$alkylcarbonyl;
or pharmaceutically acceptable salt, enantiomer or diastereomer thereof.

Further embodiment of present invention is (ii) a compound of formula (I), wherein
$R^1$ is hydroxy;
$R^2$ and $R^3$ are independently selected from hydrogen, methyl, cyclopropyl and allyl;
$R^4$ and $R^5$ are independently selected from hydrogen, methyl, ethyl, n-propyl, n-butyl, isobutyl, cyclopropyl, ethynyl, 1-propynyl, 2-cyclopropylethynyl, allyl, phenyl, 3-thiophenyl and 2-thiophenyl;
$R^6$ is hydrogen, ethoxycarbonyl or acetyl;
or pharmaceutically acceptable salt, enantiomer or diastereomer thereof.

Another embodiment of present invention is (iii) a compound of formula (I), wherein $R^1$ is hydroxy;
$R^2$ and $R^3$ are independently selected from hydrogen, $C_{2-6}$alkenyl and $C_{1-6}$alkyl;
$R^4$ and $R^5$ are independently selected from hydrogen, $C_{1-6}$alkyl, $C_{3-7}$cycloalkyl, $C_{3-7}$cycloalkyl$C_{2-6}$alkynyl, $C_{2-6}$alkenyl, $C_{2-6}$alkynyl and 2-thiophenyl;
$R^6$ is hydrogen or $C_{1-6}$alkylcarbonyl;
or pharmaceutically acceptable salt, enantiomer or diastereomer thereof.

Further embodiment of present invention is (iv) a compound of formula (I), wherein
$R^1$ is hydroxy;
$R^2$ and $R^3$ are independently selected from hydrogen, methyl and allyl;
$R^4$ and $R^5$ are independently selected from hydrogen, methyl, ethyl, n-propyl, n-butyl, isobutyl, cyclopropyl, ethynyl, 1-propynyl, 2-cyclopropylethynyl, allyl and 2-thiophenyl;
$R^6$ is hydrogen or acetyl;
or pharmaceutically acceptable salt, enantiomer or diastereomer thereof.

Another embodiment of present invention is (v) a compound of formula (I) or pharmaceutically acceptable salts, enantiomers, or diastereomers thereof, wherein $R^2$ and $R^3$ are independently selected from hydrogen and $C_{1-6}$alkyl.

A further embodiment of present invention is (vi) a compound of formula (I) or pharmaceutically acceptable salts, enantiomers, or diastereomers thereof, wherein $R^2$ and $R^3$ are independently selected from hydrogen and methyl.

Another embodiment of present invention is (vii) a compound of formula (I) or pharmaceutically acceptable salts, enantiomers, or diastereomers thereof, wherein $R^4$ and $R^5$ are independently selected from hydrogen, $C_{1-6}$alkyl, $C_{3-7}$cycloalkyl, $C_{2-6}$alkenyl, $C_{2-6}$alkynyl and 2-thiophenyl.

A further embodiment of present invention is (viii) a compound of formula (I) or pharmaceutically acceptable salts, enantiomers, or diastereomers thereof, wherein $R^4$ and $R^5$ are independently selected from hydrogen, methyl, ethyl, n-butyl, cyclopropyl, ethynyl, 1-propynyl, allyl and 2-thiophenyl.

Another embodiment of present invention is (ix) a compound of formula (I) or pharmaceutically acceptable salts, enantiomers, or diastereomers thereof, wherein $R^6$ is hydrogen.

A further embodiment of present invention is (x) a compound of formula (I), wherein $R^1$ is hydroxy;
$R^2$ and $R^3$ are independently selected from hydrogen and $C_{1-6}$alkyl;
$R^4$ and $R^5$ are independently selected from hydrogen, $C_{1-6}$alkyl, $C_{3-7}$cycloalkyl, $C_{2-6}$alkenyl, $C_{2-6}$alkynyl and 2-thiophenyl;
$R^6$ is hydrogen;
or pharmaceutically acceptable salt, enantiomer or diastereomer thereof.

Another embodiment of present invention is (xi) a compound of formula (I), wherein $R^1$ is hydroxy;
$R^2$ and $R^3$ are independently selected from hydrogen and methyl;
$R^4$ and $R^5$ are independently selected from hydrogen, methyl, ethyl, n-propyl, n-butyl, cyclopropyl, ethynyl, 1-propynyl, allyl and 2-thiophenyl;
$R^6$ is hydrogen;
or pharmaceutically acceptable salt, enantiomer or diastereomer thereof.

Another embodiment of present invention is that (xii) particular compounds of formula (I) are the following:
5-Amino-3-[2-(hydroxymethyl)-1,3-oxathiolan-5-yl]-6H-thiazolo[4,5-d] pyrimidine-2,7-dione;
5-Amino-3-[(2S)-2-(hydroxymethyl)-1,3-oxathiolan-5-yl]-6H-thiazolo[4,5-d] pyrimidine-2,7-dione;
5-Amino-3-[(2S)-2-(hydroxymethyl)-1,3-oxathiolan-5-yl] thiazolo[4,5-d] pyrimidin-2-one;
5-Amino-3-[(2S,5R)-2-[cyclopropyl(hydroxy)methyl]-1,3-oxathiolan-5-yl]-6H-thiazolo[4,5-d]pyrimidine-2,7-dione;
5-Amino-3-[(2S,5R)-2-[-cyclopropyl(hydroxy)methyl]-1,3-oxathiolan-5-yl]thiazolo[4,5-d]pyrimidin-2-one;
[[(2S,5R)-5-(5-Amino-2-oxo-thiazolo[4,5-d]pyrimidin-3-yl)-1,3-oxathiolan-2-yl]-cyclopropyl-methyl] acetate;
[[(2S,5R)-5-(5-Amino-2,7-dioxo-6H-thiazolo[4,5-d]pyrimidin-3-yl)-1,3-oxathiolan-2-yl]-cyclopropyl-methyl] acetate;
5-Amino-3-[(2S,5R)-2-(1-hydroxypropyl)-1,3-oxathiolan-5-yl]-6H-thiazolo[4,5-d] pyrimidine-2,7-dione;
5-Amino-3-[(2S,5R)-2-(1-hydroxybutyl)-1,3-oxathiolan-5-yl]-6H-thiazolo[4,5-d]pyrimidine-2,7-dione;
5-Amino-3-[(2S,5R)-2-(1-hydroxybut-2-ynyl)-1,3-oxathiolan-5-yl]-6H-thiazolo[4,5-d]pyrimidine-2,7-dione;
5-Amino-3-[(2S,5R)-2-(1-hydroxybut-2-ynyl)-1,3-oxathiolan-5-yl]thiazolo[4,5-d]pyrimidin-2-one;
1-[(2S,5R)-5-(5-Amino-thiazolo[4,5-d]pyrimidin-3-yl)-1,3-oxathiolan-2-yl] but-2-ynyl acetate;
1-[(2S,5R)-5-(5-Amino-2,7-dioxo-6H-thiazolo[4,5-d]pyrimidin-3-yl)-1,3-oxathiolan-2-yl]but-2-ynyl acetate;

5-Amino-3-[(2S,5R)-2-(3-cyclopropyl-1-hydroxy-prop-2-ynyl)-1,3-oxathiolan-5-yl]-6H-thiazolo[4,5-d]pyrimidine-2,7-dione;

5-Amino-3-[(2S,5R)-2-(1-hydroxyprop-2-ynyl)-1,3-oxathiolan-5-yl]-6H-thiazolo[4,5-d]pyrimidine-2,7-dione;

5-Amino-3-[(2S,5R)-2-(1-hydroxyethyl)-1,3-oxathiolan-5-yl]-6H-thiazolo[4,5-d]pyrimidine-2,7-dione;

5-Amino-3-[(2S,5R)-2-(1-hydroxy-3-methyl-butyl)-1,3-oxathiolan-5-yl]-6H-thiazolo[4,5-d]pyrimidine-2,7-dione;

5-Amino-3-[(2S,5R)-2-(1-hydroxybut-3-enyl)-1,3-oxathiolan-5-yl]-6H-thiazolo[4,5-d]pyrimidine-2,7-dione;

5-Amino-3-[(2S,5R)-2-(1-hydroxypentyl)-1,3-oxathiolan-5-yl]-6H-thiazolo[4,5-d] pyrimidine-2,7-dione;

5-amino-3-[(2S,5R)-2-[hydroxy(2-thienyl)methyl]-1,3-oxathiolan-5-yl]-6H-thiazolo[4,5-d]pyrimidine-2,7-dione;

5-Amino-3-[(2S,4S)-2-(hydroxymethyl)-4-methyl-1,3-oxathiolan-5-yl]-6H-thiazolo[4,5-d]pyrimidine-2,7-dione;

5-Amino-3-[(4S)-2-[(1S)-1-hydroxypropyl]-4-methyl-1,3-oxathiolan-5-yl]-6H-thiazolo[4,5-d]pyrimidine-2,7-dione;

5-Amino-3-[(2S,4S)-2-[cyclopropyl(hydroxy)methyl]-4-methyl-1,3-oxathiolan-5-yl]-6H-thiazolo[4,5-d]pyrimidine-2,7-dione;

5-Amino-3-[(4S)-2-(1-hydroxybut-2-ynyl)-4-methyl-1,3-oxathiolan-5-yl]-6H-thiazolo[4,5-d]pyrimidine-2,7-dione;

and 3-[4-Allyl-2-(hydroxymethyl)-1,3-oxathiolan-5-yl]-5-amino-6H-thiazolo[4,5-d]pyrimidine-2,7-dione;

or pharmaceutically acceptable salt, enantiomer or diastereomer thereof.

A further embodiment of present invention is that (xiii) more particular compounds of formula (I) are the following:

5-Amino-3-[(2S)-2-(hydroxymethyl)-1,3-oxathiolan-5-yl]-6H-thiazolo[4,5-d]pyrimidine-2,7-dione;

5-Amino-3-[(2S,5R)-2-[cyclopropyl(hydroxy)methyl]-1,3-oxathiolan-5-yl]-6H-thiazolo[4,5-d]pyrimidine-2,7-dione;

5-Amino-3-[(2S,5R)-2-(1-hydroxypropyl)-1,3-oxathiolan-5-yl]-6H-thiazolo[4,5-d] pyrimidine-2,7-dione;

5-Amino-3-[(2S,5R)-2-(1-hydroxybutyl)-1,3-oxathiolan-5-yl]-6H-thiazolo[4,5-d]pyrimidine-2,7-dione;

5-Amino-3-[(2S,5R)-2-(1-hydroxybut-2-ynyl)-1,3-oxathiolan-5-yl]-6H-thiazolo[4,5-d]pyrimidine-2,7-dione;

5-Amino-3-[(2S,5R)-2-(1-hydroxyprop-2-ynyl)-1,3-oxathiolan-5-yl]-6H-thiazolo[4,5-d]pyrimidine-2,7-dione;

5-Amino-3-[(2S,5R)-2-(1-hydroxyethyl)-1,3-oxathiolan-5-yl]-6H-thiazolo[4,5-d]pyrimidine-2,7-dione;

5-Amino-3-[(2S,5R)-2-(1-hydroxybut-3-enyl)-1,3-oxathiolan-5-yl]-6H-thiazolo[4,5-d]pyrimidine-2,7-dione;

5-Amino-3-[(2S,5R)-2-(1-hydroxypentyl)-1,3-oxathiolan-5-yl]-6H-thiazolo[4,5-d] pyrimidine-2,7-dione;

5-amino-3-[(2S,5R)-2-[hydroxy(2-thienyl)methyl]-1,3-oxathiolan-5-yl]-6H-thiazolo[4,5-d]pyrimidine-2,7-dione;

5-Amino-3-[(2S,4S)-2-(hydroxymethyl)-4-methyl-1,3-oxathiolan-5-yl]-6H-thiazolo[4,5-d]pyrimidine-2,7-dione;

5-Amino-3-[(4S)-2-[(1S)-1-hydroxypropyl]-4-methyl-1,3-oxathiolan-5-yl]-6H-thiazolo[4,5-d]pyrimidine-2,7-dione;

and 5-Amino-3-[(2S,4S)-2-[cyclopropyl(hydroxy)methyl]-4-methyl-1,3-oxathiolan-5-yl]-6H-thiazolo[4,5-d]pyrimidine-2,7-dione;

or pharmaceutically acceptable salt, enantiomer or diastereomer thereof.

Another embodiment of present invention is (xiv) a compound of formula (Ia),

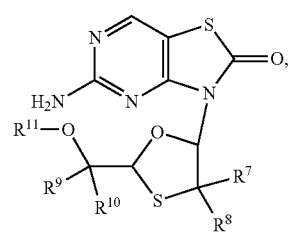

(Ia)

wherein $R^7$ and $R^8$ are independently selected from hydrogen, $C_{2-6}$alkenyl and $C_{1-6}$alkyl;

$R^9$ and $R^{10}$ are independently selected from hydrogen, $C_{1-6}$alkyl, $C_{3-7}$cycloalkyl, $C_{3-7}$cycloalkyl$C_{2-6}$alkynyl, $C_{2-6}$alkenyl, $C_{2-6}$alkynyl and 2-thiophenyl;

$R^{11}$ is hydrogen or $C_{1-6}$alkylcarbonyl;

or pharmaceutically acceptable salt, enantiomer or diastereomer thereof.

A further embodiment of present invention is (xv) a compound of formula (Ia), wherein $R^7$ and $R^8$ are independently selected from hydrogen, methyl and allyl;

$R^9$ and $R^{10}$ are independently selected from hydrogen, methyl, ethyl, n-propyl, n-butyl, isobutyl, cyclopropyl, ethynyl, 1-propynyl, 2-cyclopropylethynyl, allyl and 2-thiophenyl;

$R^{11}$ is hydrogen or acetyl;

or pharmaceutically acceptable salt, enantiomer or diastereomer thereof.

Another embodiment of present invention is (xvi) a compound of formula (Ia), wherein $R^7$ and $R^8$ are hydrogen;

$R^9$ and $R^{10}$ are independently selected from hydrogen, $C_{2-6}$alkynyl and $C_{3-7}$cycloalkyl;

$R^{11}$ is hydrogen or $C_{1-6}$alkylcarbonyl;

or pharmaceutically acceptable salt, enantiomer or diastereomer thereof.

A further embodiment of present invention is (xvii) a compound of formula (Ia), wherein $R^7$ and $R^8$ are hydrogen;

$R^9$ and $R^{10}$ are independently selected from hydrogen, 1-propynyl and cyclopropyl;

$R^{11}$ is hydrogen or acetyl;

or pharmaceutically acceptable salt, enantiomer or diastereomer thereof.

Another embodiment of present invention is that (xviii) particular compounds of formula (Ia) are the following:

5-Amino-3-[(2S)-2-(hydroxymethyl)-1,3-oxathiolan-5-yl]thiazolo[4,5-d] pyrimidin-2-one;

5-Amino-3-[(2S,5R)-2-[-cyclopropyl(hydroxy)methyl]-1,3-oxathiolan-5-yl]thiazolo[4,5-d]pyrimidin-2-one;

[[(2S,5R)-5-(5-Amino-2-oxo-thiazolo[4,5-d]pyrimidin-3-yl)-1,3-oxathiolan-2-yl]-cycl opropyl-methyl] acetate;

5-Amino-3-[(2S,5R)-2-(1-hydroxybut-2-ynyl)-1,3-oxathiolan-5-yl]thiazolo[4,5-d]pyrimidin-2-one;

and 1-[(2S,5R)-5-(5-Amino-2-oxo-thiazolo[4,5-d]pyrimidin-3-yl)-1,3-oxathiolan-2-yl]but-2-ynyl acetate;

or pharmaceutically acceptable salt, enantiomer or diastereomer thereof.

A further embodiment of present invention is that

5-Amino-3-[(2S)-2-(hydroxymethyl)-1,3-oxathiolan-5-yl]thiazolo[4,5-d] pyrimidin-2-one, 5-Amino-3-[(2S,5R)-2-[-cyclopropyl(hydroxy)methyl]-1,3-oxathiolan-5-yl]thiazolo[4,5-d]pyrimidin-2-one,

[[(2S,5R)-5-(5-Amino-2-oxo-thiazolo[4,5-d]pyrimidin-3-yl)-1,3-oxathiolan-2-yl]-cyclopropyl-methyl] acetate, 5-Amino-3-[(2S,5R)-2-(1-hydroxybut-2-ynyl)-1,3-oxathiolan-5-yl]thiazolo[4,5-d]pyrimidin-2-one, and 1-[(2S,5R)-5-(5-Amino-2-oxo-thiazolo[4,5-d]pyrimidin-3-yl)-1,3-oxathiolan-2-yl]but-2-ynyl acetate;

or pharmaceutically acceptable salt, enantiomer or diastereomer thereof; are prodrugs.

Synthesis

The compounds of the present invention can be prepared by any conventional means. Suitable processes for synthesizing these compounds as well as their starting materials are provided in the schemes below and in the examples. All substituents, in particular, $R^1$ to $R^{11}$ are as defined above unless otherwise indicated. Furthermore, and unless explicitly otherwise stated, all reactions, reaction conditions, abbreviations and symbols have the meanings well known to a person of ordinary skill in organic chemistry.

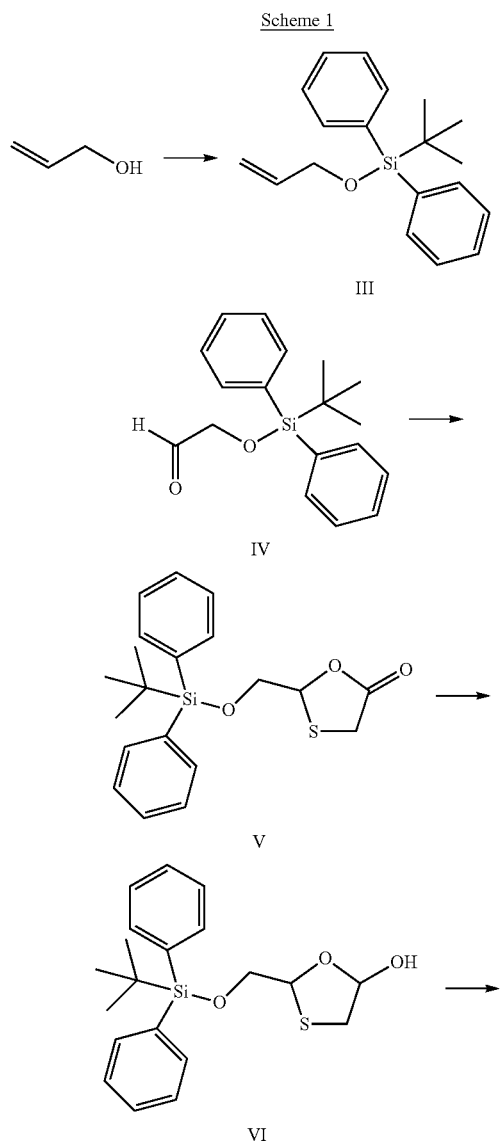

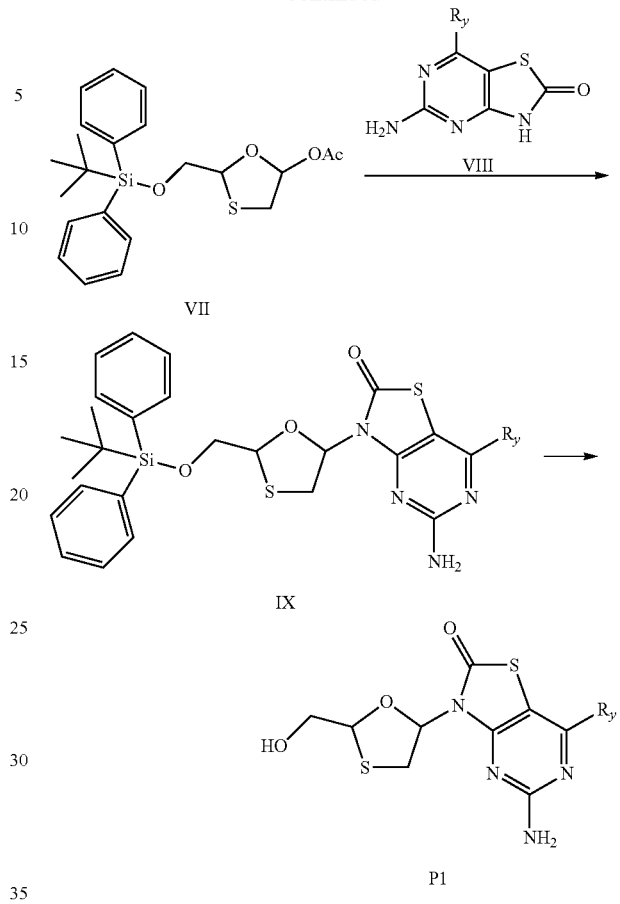

$R_y$ is hydrogen or hydroxy.

Protection of allyl alcohol with tert-butylchlorodiphenylsilane in the presence of imidazole gives silyl ether III. Oxidation of III with ozone affords aldehyde IV. Cyclization of the intermediate IV with mercaptoacetic acid gives lactone V. Reduction of the lactone V with reductant, such as diisobutyl aluminium hydride, gives hemiacetal VI. Acylation of the hemiacetal VI with acetic anhydride affords intermediate VII. Coupling of VII and VIII in the presence of one appropriate silicon etherification agent such as N,O-bis(trimethylsilyl)acetamide and Lewis acid gives the intermediate IX. Deprotection of IX with fluoride reagent, such as TBAF, and purification by preparative HPLC affords compound P1.

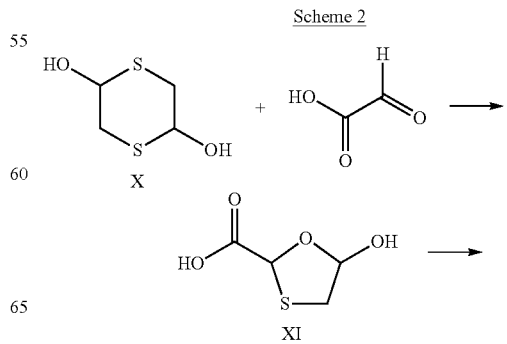

13

-continued

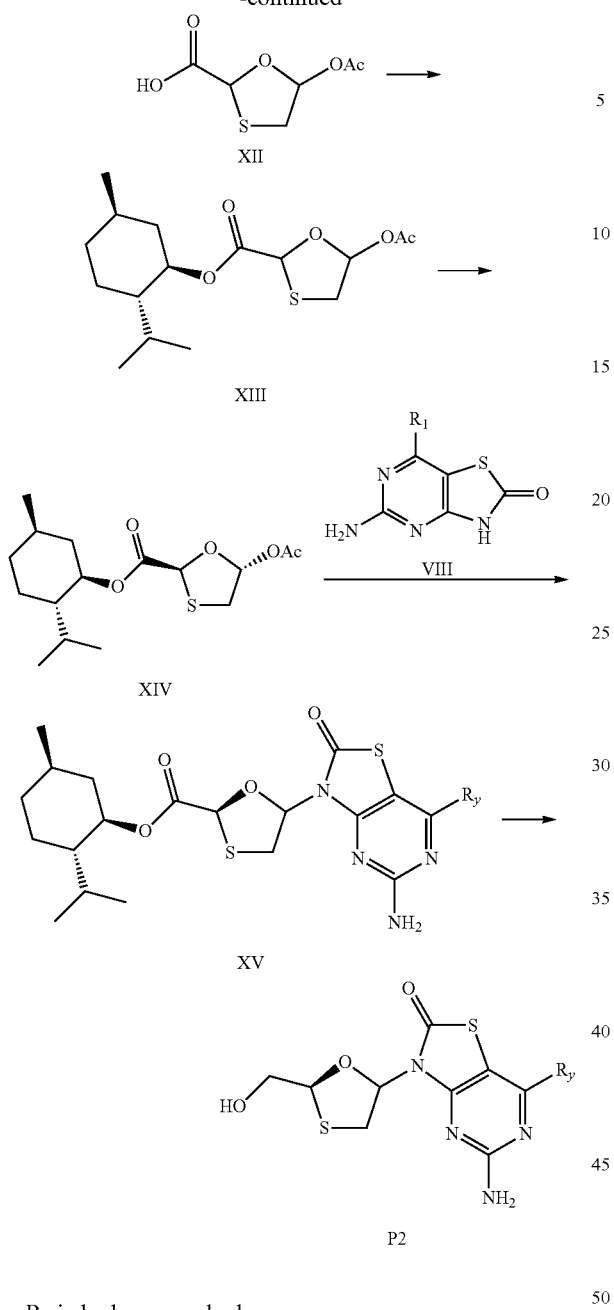

$R_y$ is hydrogen or hydroxy.

Cyclization of 1,4-dithiane-2,5-diol X with oxaldehydic acid gives intermediate XI. Acylation of the intermediate XI with acetic anhydride affords intermediate XII. Coupling of intermediate XII with L-(−)-menthol in the presence of appropriate base, such as DMAP, and condensation reagent, such as dicyclohexylcarbodiimide, affords ester XIII. Chiral separation of ester XIII by supercritical fluid chromatography (SFC) affords optical pure compound XIV. Coupling of XIV and VIII in the presence of appropriate silicon etherification reagent, such as N,O-bis(trimethylsilyl)acetamide and Lewis acid, gives intermediate XV. Reduction of XV with reductant, such as LiAlH₄, and purification by preparative HPLC affords compound P2.

14

Scheme 3

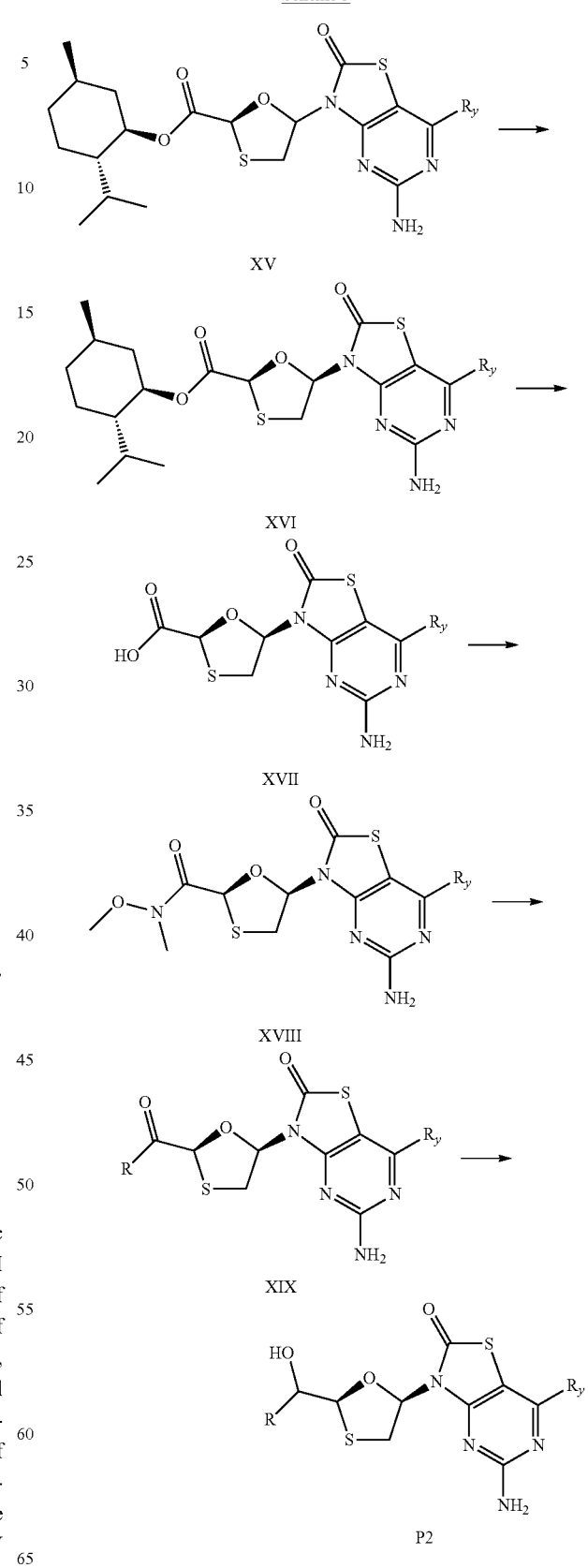

R is $R^4$, $R^5$, $R^9$ or $R^{10}$. $R_y$ is hydrogen or hydroxy.

Chiral separation of intermediate XV by supercritical fluid chromatography (SFC) affords optical pure compound XVI. Hydrolysis of compound XVI with an appropriate base, such as LiOH, gives acid XVII. Coupling of acid XVII with Weinreb amine in the presence of appropriate base, such as LiOH, and condensation agent, such as 4-(4,6-dimethoxy-1,3,5-triazin-2-yl)-4-methylmorpholinium chloride, affords Weinreb amide XVIII. The Weinreb amide XVIII is treated with a nucleophile agent, such as Grignard reagent, and gives the ketone XIX. Reduction of the ketone XIX with reductant, such as NaBH$_4$, and purification by preparative HPLC affords compound P3.

R is R$^4$, R$^5$, R$^9$ or R$^{10}$. R$_y$ is hydrogen or hydroxy.

Compound P3 can also be prepared via Scheme 4. Protection of the amino group of Weinreb amide XVIII with 1-(chlorodiphenylmethyl)-4-methoxybenzene gives intermediate XX. The Intermediate XX is treated with Grignard reagent or organolithium reagent and gives ketone XXI. Reduction of the ketone XXI with reductant, such as NaBH$_4$, affords alcohol XXII. Deprotection of XXII with acid, such as formic acid, and purification by preparative HPLC affords compound P3. Esterification of alcohol XXII with acyl chloride or acid anhydride affords ester XXIII.

Scheme 4

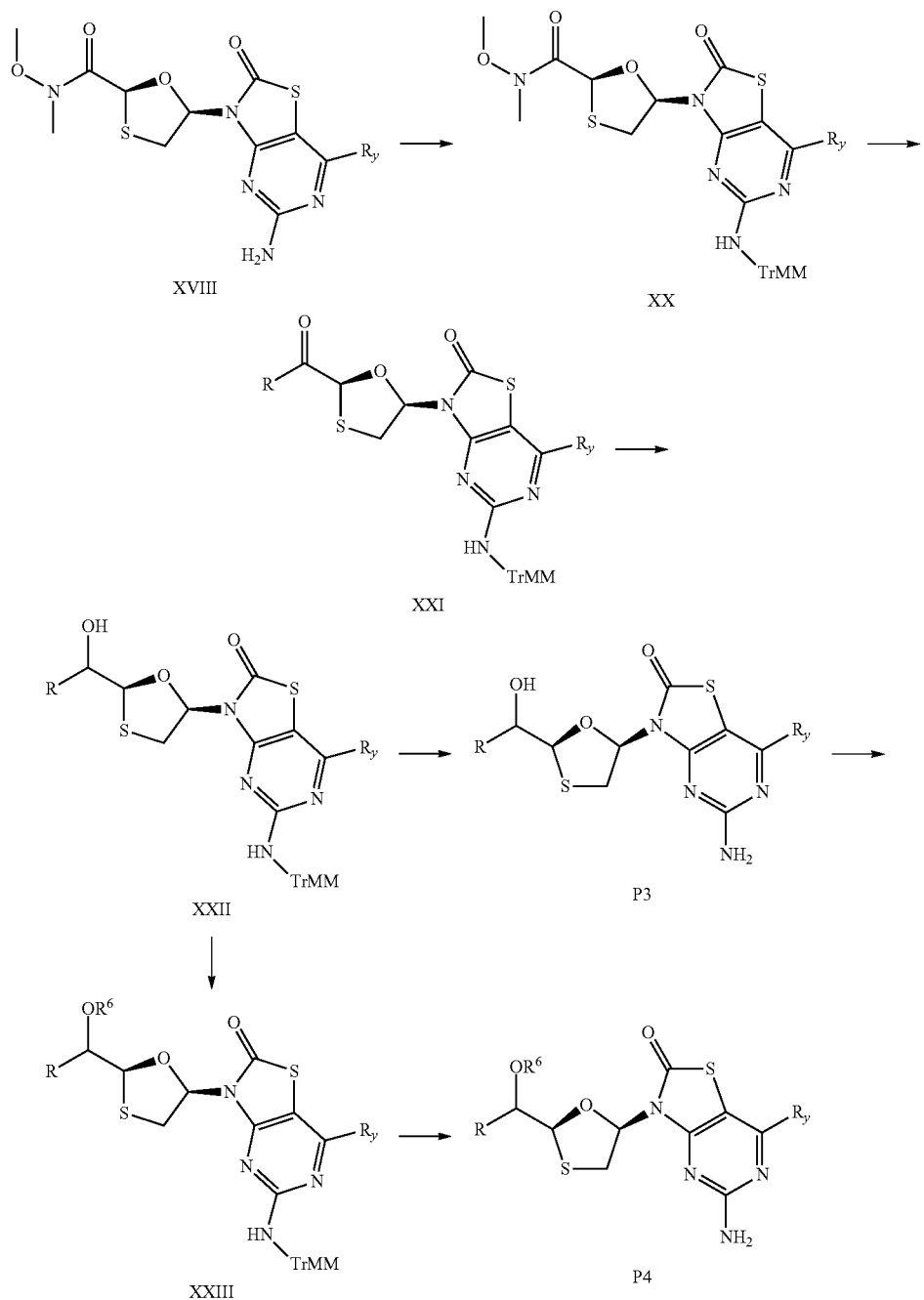

Deprotection of XXIII with acid, such as formic acid, and purification by preparative HPLC affords compound P4.

This invention also relates to a process for the preparation of a compound of formula I comprising the reaction of:

(a) the reaction of a compound of formula (IX),

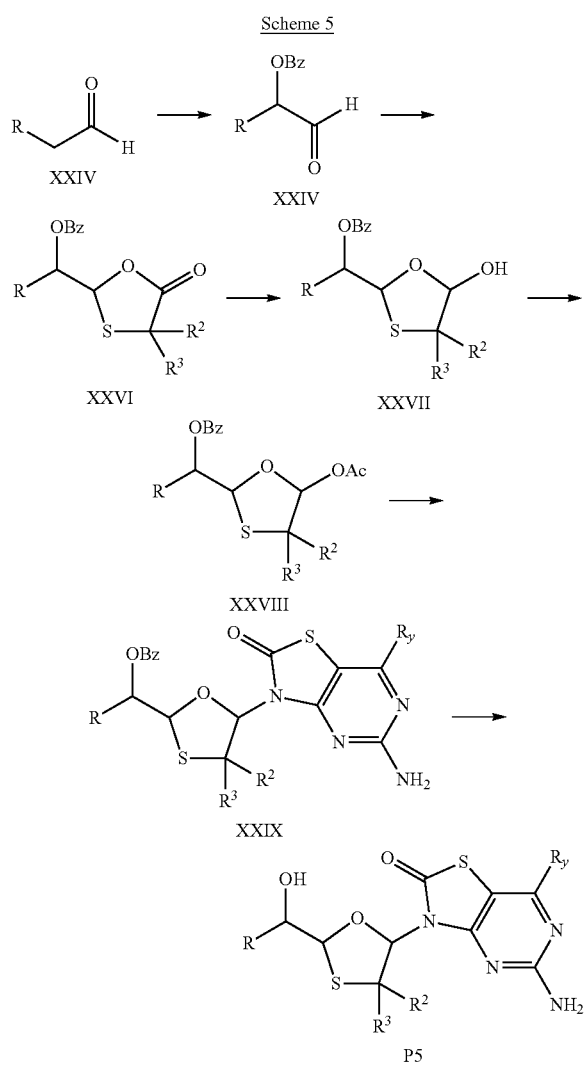

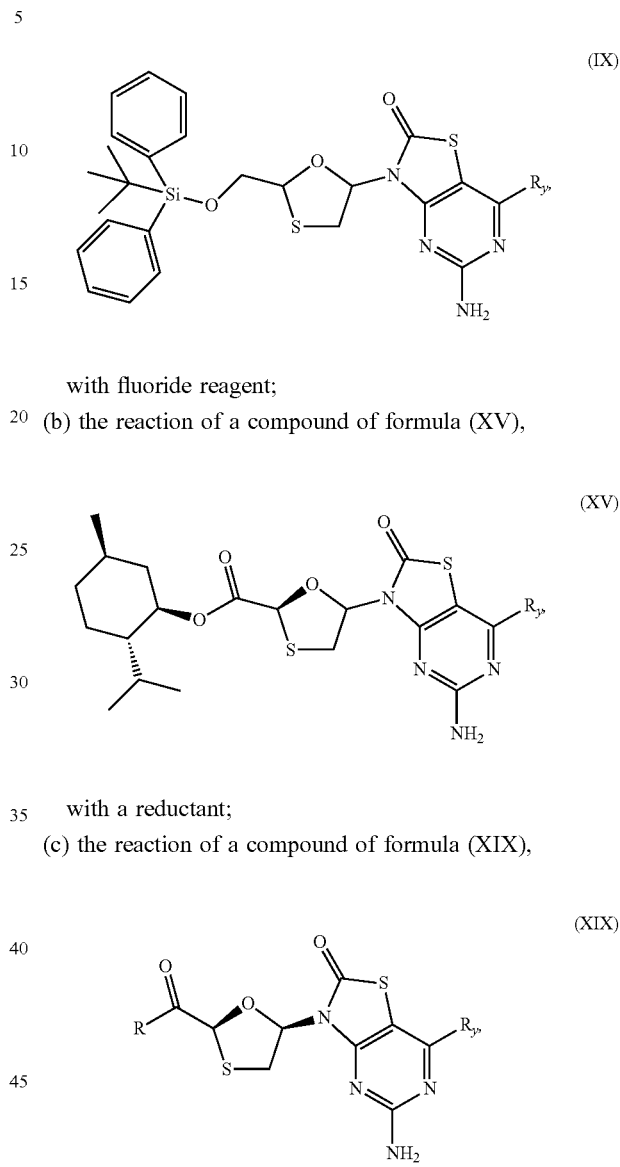

with fluoride reagent;

(b) the reaction of a compound of formula (XV), with a reductant;

(c) the reaction of a compound of formula (XIX),

R is $R^4$, $R^5$, $R^9$ or $R^{10}$. $R_y$ is hydrogen or hydroxy.

Benzoylation of XXIV in the presence of [diphenyl-[(2R)-pyrrolidin-2-yl]methoxy]-trimethyl-silane and benzoyl peroxide affords intermediate XXV. Cyclization of the intermediate XXV with substituted or un-substituted mercaptoacetic acid without solvent or with solvent, such as toluene, gives lactone XXVI. Reduction of the lactone XXVI with reductant, such as lithium tri-tert-butoxyaluminum hydride, gives hemiacetal XXVII. Acylation of the hemiacetal XXVII with acetic anhydride affords intermediate XXVIII. Coupling of the XXVIII and VIII in the presence of appropriate silicon agent such as N,O-bis(trimethylsilyl)acetamide and Lewis acid gives XXIX. Hydrolysis of compound XXIX with a base, such as $K_2CO_3$, and purification by preparative HPLC affords compound P5.

with a reductant, wherein R is $R^4$, $R^5$, $R^9$ or $R^{10}$;

(d) the reaction of a compound of formula (XXII),

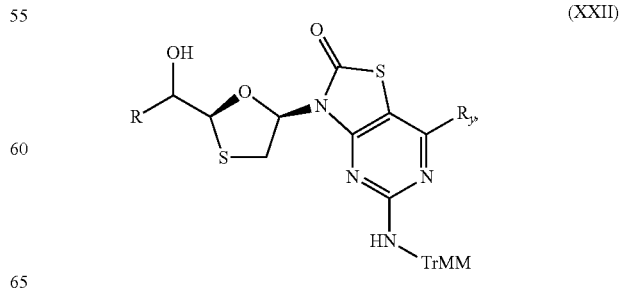

with an acid, wherein R is $R^4$, $R^5$, $R^9$ or $R^{10}$;

(e) the reaction of a compound of formula (XXIII),

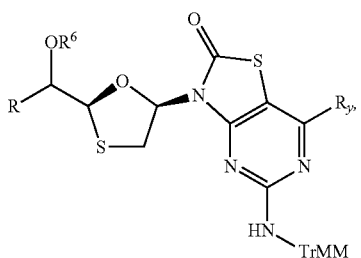

(XXIII)

with an acid, wherein R is $R^4$, $R^5$, $R^9$ or $R^{10}$; or
(f) the reaction of a compound of formula (XXIX),

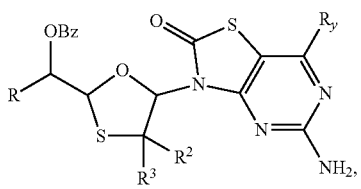

(XXIX)

with a base, wherein R is $R^4$, $R^5$, $R^9$ or $R^{10}$;
wherein $R_y$, $R^2$, $R^3$, $R^4$, $R^5$, $R^6$, $R^9$ and $R^{10}$ are defined above.

In step (a), the fluoride reagent can be for example TBAF.
In step (b), the reductant can be for example $LiAlH_4$.
In step (c), the reductant can be for example $NaBH_4$.
In step (d) and (e), the acid can be for example formic acid.
In step (f), the base can be for example $K_2CO_3$.

A compound of formula (I) or (Ia) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) or their prodrugs may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) or their prodrugs are formulated in an acetate buffer, at pH 5. In another embodiment, the compounds of formula (I) or their prodrugs are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to activate TLR7 receptor and lead to produce INF-α and other cytokines, which can be used, but not limited, for the treatment or prevention of hepatitis B and/or C viral infected patients.

In one example, the pharmaceutically effective amount of the compound of the invention administered parenterally per dose will be in the range of about 0.1 to 50 mg/kg, alternatively about 0.1 to 30 mg/kg of patient body weight per day, with the typical initial range of compound used being 0.3 to 15 mg/kg/day. In another embodiment, oral unit dosage forms, such as tablets and capsules, preferably contain from about 20 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 20 to 1000 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 20 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I) or their prodrugs, or pharmaceutically acceptable salts or enantiomers or diastereomers thereof.

In a further embodiment includes a pharmaceutical composition comprising a compound of formula (I) or their prodrugs, or pharmaceutically acceptable salts or enantiomers or diastereomers thereof, together with a pharmaceutically acceptable carrier or excipient.

Another embodiment includes a pharmaceutical composition comprising a compound of formula (I) or their prodrugs or pharmaceutically acceptable salts or enantiomers or diastereomers thereof for use in the treatment of hepatitis B virus infection.

Indications and Methods of Treatment

The present invention provides methods for treating or preventing a hepatitis B viral infection and/or hepatitis C viral infection in a patient in need thereof.

The present invention further provides methods for introducing a therapeutically effective amount of a formula (I) compound or their prodrugs, or other compound of the invention or combination of such compounds into the blood stream of a patient in the treatment and/or prevention of hepatitis B and/or C viral infection.

The magnitudes of a prophylactic or therapeutic dose of a formula (I) compound or their prodrugs, or other compound of the invention or a pharmaceutically acceptable salt, solvate, or hydrate, thereof in the acute or chronic treatment or prevention of an infection will vary, however, with the nature and severity of the infection, and the route by which the active ingredient is administered. The dose, and in some cases the dose frequency, will also vary according to the infection to be treated, the age, body weight, and response of the individual patient. Suitable dosing regimens can be readily selected by those skilled in the art with due consideration of such factors.

The methods of the present invention are particularly well suited for human patients. In particular, the methods and doses of the present invention can be useful for immunocompromised patients including, but not limited to HBV and/or HCV infected patients, and patients with an immunodegenerative disease. Furthermore, the methods can be useful for immunocompromised patients currently in a state of remission. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Another embodiment includes a method of treating or preventing hepatitis B viral infection and/or hepatitis C viral infection in a mammal in need of such treatment, wherein the method comprises administering to said mammal a therapeutically effective amount of a compound of formula (I), or enantiomers, diastereomers, prodrugs or pharmaceutically acceptable salts thereof.

EXAMPLES

Figure 1:
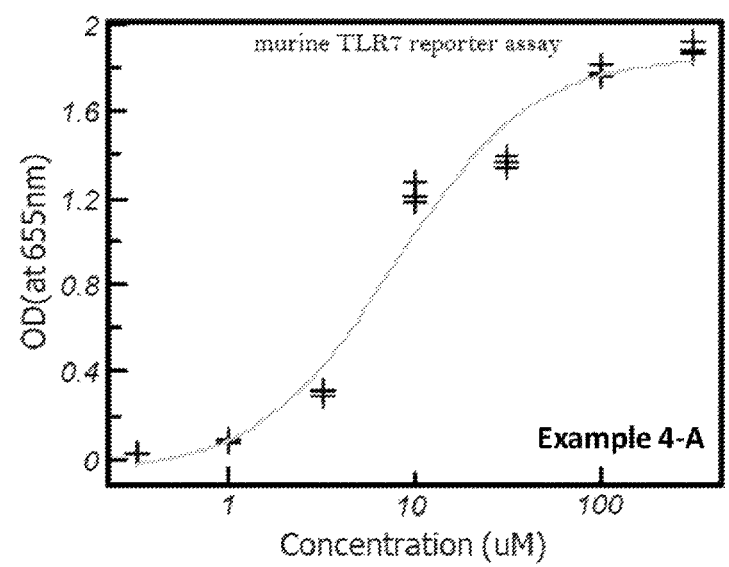
FIG. 1: Example 4-A activated murine TLR7 in an HEK-Blue-mTLR7 assay. The cells were incubated with Example 4-A at indicated concentrations for 20 hours. The activation of murine TLR7 was measured using a Quanti-Blue assay.

The invention will be more fully understood by reference to the following examples. They should not, however, be construed as limiting the scope of the invention.

ABBREVIATIONS

ACN: acetonitrile
MMTrCl: 1-(chlorodiphenylmethyl)-4-methoxybenzene
DCE: 1,2-dichloroethane
HATU: 1-[bis(dimethylamino)methylene]-1H-1,2,3-triazolo[4,5-b]pyridinium 3-oxid hexafluorophosphate
DMAP: 4-dimethylaminopyridine
p-TsOH: 4-methylbenzenesulfonic acid
FBS: fetal bovine serum
Hz: hertz
HPLC: high performance liquid chromatography
LiAlH$_4$: lithium aluminium hydride
MS (ESI): mass spectroscopy (electron spray ionization)
MHz: megahertz
BSA: N, O-bis(trimethylsilyl)acetamide
obsd. observed
NaBH$_4$: sodium borohydride
TBAF: tetrabutylammonium fluoride
EC$_{50}$: The molar concentration of an agonist, which produces 50% of the maximum possible response for that agonist
TLC: thin layer chromatography
TEA: triethylamine
TMSI: trimethylsilyl iodide
TMSOTf: trimethylsilyl trifluoromethanesulfonate
General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column.

LC/MS spectra were obtained using a Waters UPLC-SQD Mass. Standard LC/MS conditions were as follows (running time 3 minutes):

Acidic condition: A: 0.1% formic acid and 1% acetonitrile in $H_2O$; B: 0.1% formic acid in acetonitrile;

Basic condition: A: 0.05% $NH_3 \cdot H_2O$ in $H_2O$; B: acetonitrile.

Mass spectra (MS): generally only ions which indicate the parent mass are reported, and unless otherwise stated the mass ion quoted is the positive mass ion $(M+H)^+$.

NMR Spectra were obtained using Bruker Avance 400 MHz.

All reactions involving air-sensitive reagents were performed under an argon atmosphere. Reagents were used as received from commercial suppliers without further purification unless otherwise noted.

PREPARATIVE EXAMPLES

Example 1

5-Amino-3-[2-(hydroxymethyl)-1,3-oxathiolan-5-yl]-6H-thiazolo[4,5-d] pyrimidine-2,7-dione

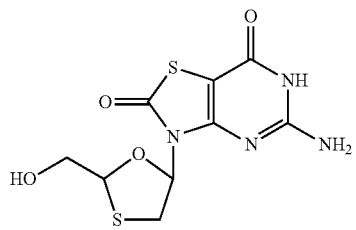

1

Preparation of allyloxy-tert-butyl-diphenyl-silane

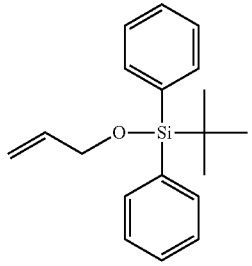

III

To a solution of allyl alcohol (35 g, 603 mmol) and imidazole (82 g, 1.2 mol) in DCM (560 mL) was added tert-butylchlorodiphenylsilane (198 g, 723 mmol) dropwise with stirring. After being stirred at room temperature for 16 hours, the resulting reaction mixture was filtered. The filtrate was concentrated in vacuo and the residue was purified by column chromatography on silica gel (eluting with petroleum ether) to afford the allyloxy-tert-butyl-diphenyl-silane (compound III) 143 g as a colorless liquid.

Compound III: $^1$H NMR (400 MHz, DMSO-d6) δ ppm: 7.60-7.62 (m, 4H), 7.36-7.42 (m, 6H), 5.85-5.95 (m, 1H), 5.33 (dd, J=17.2, 2.0 Hz, 1H), 5.09 (dd, J=10.8, 2.0 Hz, 1H), 4.16-4.17 (m, 2H), 0.98 (s, 9H).

Preparation of 2-[tert-butyl(diphenyl)silyl]oxyacetaldehyde

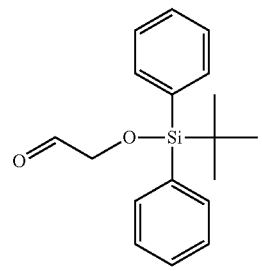

IV

To a solution of allyloxy-tert-butyl-diphenyl-silane (20 g, 67 mmol) in DCM (516 mL) was added ozone at −78° C. until the solution became blue. After being stirred at −78° C. for 30 minutes, nitrogen was added into the reaction mixture until the solution became colorless, then dimethyl sulfide (19.4 mL, 263 mmol) was added dropwise. After being stirred at room temperature for 16 hours, the solution was washed with brine and concentrated in vacuo. The residue was purified by column chromatography on silica gel (eluting with 1:20 ethyl acetate in petroleum ether) to afford 2-[tert-butyl(diphenyl)silyl]oxyacetaldehyde (compound IV) 12 g as a colorless oil.

Compound IV: $^1$H NMR (400 MHz, DMSO-d6) δ ppm: 9.55 (s, 1H), 7.61-7.66 (m, 4H), 7.38-7.44 (m, 6H), 4.38 (s, 2H), 0.95-1.01 (m, 9H).

Preparation of 2-[[tert-butyl(diphenyl)silyl]oxymethyl]-1,3-oxathiolan-5-one

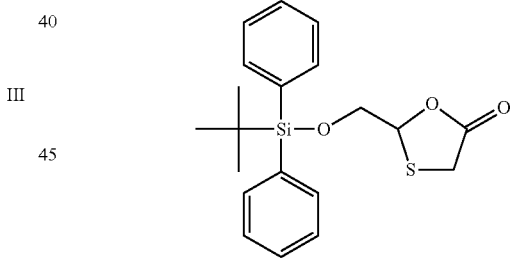

V

The solution of 2-[tert-butyl(diphenyl)silyl]oxyacetaldehyde (6.5 g, 21.7 mmol) and thioglycolic acid (1.52 mL, 21.7 mmol) in toluene (87 mL) was refluxed for 2 hours. After being cooled to room temperature, the resulting reaction mixture was washed with saturated $NaHCO_3$ solution. The aqueous phase was extracted with diethyl ether (100 mL) twice. The combined organic phase was washed with water (200 mL) twice, dried over $MgSO_4$, filtered and concentrated in vacuo to give colorless oil. The oil was purified by column chromatography on silica gel (eluting with 1:20 ethyl acetate in petroleum ether) to give a crude product which was recrystallized from petroleum ether to afford 2-[[tert-butyl(diphenyl)silyl]oxymethyl]-1,3-oxathiolan-5-one (compound V) 4.0 g as a white solid.

Compound V: $^1$H NMR (400 MHz, DMSO-d6) δ ppm: 7.62-7.67 (m, 4H), 7.44-7.50 (m, 6H), 5.77 (t, J=3.6 Hz, 1H), 3.91-3.94 (m, 1H), 3.79-3.83 (m, 3H), 1.00 (s, 9H).

Preparation of [2-[[tert-butyl(diphenyl)silyl]oxymethyl]-1,3-oxathiolan-5-yl] acetate

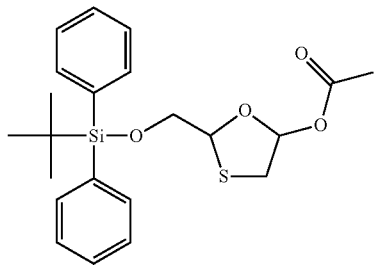

VII

To a solution of 2-[[tert-butyl(diphenyl)silyl]oxymethyl]-1,3-oxathiolan-5-one (1 g, 2.7 mmol) was added diisobutyl aluminium hydride (2.8 mL, 1.0 M in toluene, 2.8 mmol) dropwise while keeping inner temperature at −78° C. After the completion of the addition, the reaction mixture was stirred at −78° C. for another 30 minutes then acetic anhydride (1 mL, 10.6 mmol) was added. After being stirred at room temperature for 16 hours, water (1 mL) was added and the resulting reaction mixture was stirred at room temperature for 1 hour. The mixture was diluted with methyl tert-butyl ether (60 mL), dried over MgSO$_4$ and filtered. The filtrate was concentrated in vacuo and purified by column chromatography on silica gel (eluting with 1:10 ethyl acetate in petroleum ether) to give [2-[[tert-butyl(diphenyl)silyl]oxymethyl]-1,3-oxathiolan-5-yl] acetate (compound VII) 0.3 g as a yellow oil.

Compound VII: $^1$H NMR (400 MHz, DMSO-d6) δ ppm: 7.62-7.65 (m, 4H), 7.42-7.48 (m, 6H), 6.59-6.60 (m, 1H), 5.42-5.46 (m, 1H), 3.75-3.82 (m, 2H), 3.26-3.34 (m, 1H), 3.11-3.14 (m, 1H), 2.04 (s, 2H), 1.83 (s, 1H), 1.00 (s, 9H).

Preparation of 5-amino-3-[2-[[tert-butyl(diphenyl)silyl]oxymethyl]-1,3-oxathiolan-5-yl]-6H-thiazolo[4,5-d]pyrimidine-2,7-dione

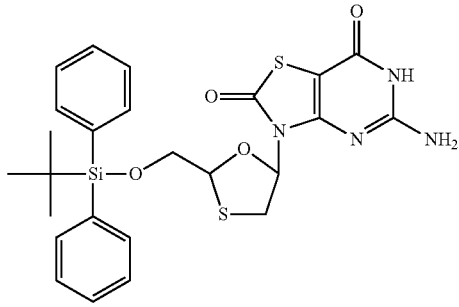

1e

To a suspension of 5-amino-3,6-dihydrothiazolo[4,5-d]pyrimidine-2,7-dione (CAS #: 30161-97-8, commercial available from J&K Scientific, 265 mg, 1.4 mmol) in ACN (5 mL) was added BSA (588 mg, 2.9 mmol). The resulting reaction mixture was then stirred at 70° C. for 0.5 hour under argon to form a clear solution. After the solution was cooled to room temperature, [2-[[tert-butyl(diphenyl)silyl]oxymethyl]-1,3-oxathiolan-5-yl] acetate (400 mg, 0.96 mmol) and TMSOTf (213 mg, 0.96 mmol) were added in sequence. After being heated with stirring at 70° C. for 14 hours, the solvent was removed in vacuo. The residue was partitioned between EtOAc and saturated NaHCO$_3$ solution (30 mL). The organic layer was separated and the aqueous phase was extracted with EtOAc (30 mL) twice. The combined organic layer was washed with brine, and dried over Na$_2$SO$_4$. After concentration, the residue was purified by preparative HPLC to afford [2-[[tert-butyl(diphenyl)silyl]oxymethyl]-1,3-oxathiolan-5-yl] acetate (compound 1e) 20 mg as a white solid. MS obsd. (ESI$^-$) [(M−H)$^-$]: 539.

Preparation of 5-amino-3-[2-(hydroxymethyl)-1,3-oxathiolan-5-yl]-6H-thiazolo[4,5-d]pyrimidine-2,7-dione

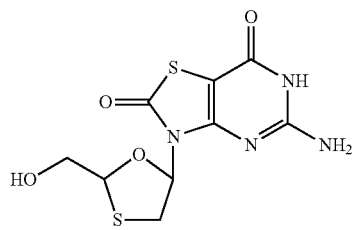

1

To a solution of [2-[[tert-butyl(diphenyl)silyl]oxymethyl]-1,3-oxathiolan-5-yl] acetate (20 mg, 0.04 mmol) in THF (5 mL) was added TBAF (1M in THF, 1 mL, 1 mmol). After being stirred at room temperature for 2 hours, the resulting reaction mixture was concentrated in vacuo and purified by preparative HPLC to give two sets of diastereomers with cis- and trans-configuration, one of which was characterized as Example 1-A and the other was Example 1-B.

Example 1-A 1.8 mg, $^1$H NMR (400 MHz, DMSO-d6) δ ppm: 6.09 (dd, J=9.0, 5.8 Hz, 1H), 5.08 (t, J=5.6 Hz, 1H), 3.94-4.03 (m, 1H), 3.66 (dd, J=11.4, 6.1 Hz, 1H), 3.51 (dd, J=11.4, 5.1 Hz, 1H), 3.11-3.23 (m, 1H). MS obsd. (ESI$^-$) [(M−H)$^-$]: 301.

Example 1-B $^1$H NMR (400 MHz, DMSO-d6) δ ppm: 6.54 (s, 1H), 5.73 (dd, J=5.6, 4.1 Hz, 1H), 3.97 (dd, J=11.3, 7.3 Hz, 1H), 3.75-3.82 (m, 1H), 3.69-3.74 (m, 1H), 3.39-3.43 (m, 1H). MS obsd. (ESI$^-$) [(M−H)$^-$]: 301.

Example 2

5-Amino-3-[(2S)-2-(hydroxymethyl)-1,3-oxathiolan-5-yl]-6H-thiazolo[4,5-d]pyrimidine-2,7-dione

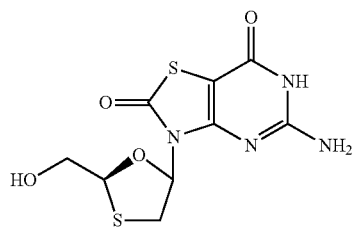

2

Preparation of 5-hydroxy-1,3-oxathiolane-2-carboxylic acid

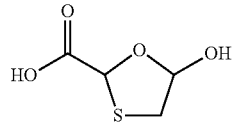

XI

To a stirred solution of 1,4-dithiane-2,5-diol (150 g, 0.98 mol) in methyl tert-butyl ether (500 mL) and cyclohexane (150 mL) was added glyoxylic acid (180 g, 1.96 mol). The resulting reaction mixture was stirred at 80° C. under Dean-Stark conditions for 16 hours. The resulting solution was concentrated in vacuo. The residue was purified by column chromatography on silica gel (eluting with 1:7 ethyl acetate in petroleum ether to 100% ethyl acetate) to afford 220 g of the crude 5-hydroxy-1,3-oxathiolane-2-carboxylic acid (compound XI), which was used directly in the next step without further purification.

Preparation of trans-5-acetoxy-1,3-oxathiolane-2-carboxylic acid

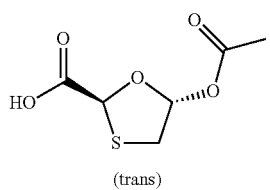

2b (trans)

To a solution of 5-hydroxy-1,3-oxathiolane-2-carboxylic acid (220 g, 1.5 mol) in HOAc (1.5 L) was added concentrated sulfuric acid (1 mL) and acetic anhydride (50 g, 0.5 mol). After being stirred at room temperature for 16 hours, the resulting reaction mixture was diluted with water and extracted with EtOAc. The organic phase was combined and concentrated in vacuo. The residue was purified by column chromatography on silica gel (eluting with 1:10 to 1:7 ethyl acetate in petroleum ether) to afford crude product, which was recrystallized from toluene to give trans-5-acetoxy-1,3-oxathiolane-2-carboxylic acid (compound 2b) 10 g. (For the synthesis, please also refer to: *J. Org. Chem.* 1995, 60, 2621-2623)

Compound 2b: $^1$H NMR (400 MHz, DMSO-d6) δ ppm: 13.26 (br, 1H), 6.66 (d, J=4.0 Hz, 1H), 5.66 (s, 1H), 3.30-3.37 (m, 1H), 3.19-3.25 (m, 1H), 2.04 (s, 3H).

Preparation of [(1R,2S,5R)-2-isopropyl-5-methyl-cyclohexyl] (2S,5S)-5-acetoxy-1,3-oxathiolane-2-carboxylate

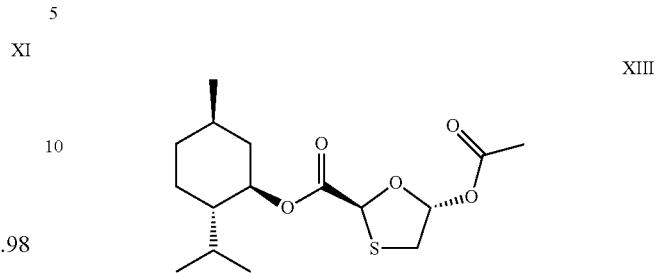

XIII

A solution of dicyclohexylcarbodiimide (12 g, 57 mmol) in DCM (50 mL) was added to a round bottom flask containing a solution of trans-5-acetoxy-1,3-oxathiolane-2-carboxylic acid (10 g, 52 mmol), L-(−)-menthol (8.9 g, 57 mmol) and DMAP (0.6 g, 5.2 mmol) in DCM (100 mL) at 0° C. The reaction mixture was stirred at room temperature for 16 hours to the above mixture were added methanol (2 mL) and glacial acetic acid (2 mL). After being stirred for another 10 minutes, the reaction mixture was diluted with hexane (250 mL), filtrated through celite and the filtrate was concentrated to yield crude product. (*J. Org. Chem.* 1995, 60, 2621-2623). The crude product was re-dissolved in hexane (250 mL), filtered and the filtrate was concentrated in vacuo. The residue was purified by supercritical fluid chromatography (SFC) to give [(1R,2S,5R)-2-isopropyl-5-methyl-cyclohexyl] (2S,5S)-5-acetoxy-1,3-oxathiolane-2-carboxylate (compound XIII) 3.2 g with a diastereoisomeric excess of 85% as a colorless oil. The diastereoisomeric excess value of compound XIII was obtained by HPLC (Agilent 1260 HPLC) analysis using a chiral column (CHIRALPAK IA-3 ODH (4.6 mm×250 mm, 5 μm)). The mobile phase of the chiral analysis was 20:80 acetonitrile in MeOH.

Compound XIII: $^1$H NMR (400 MHz, CDCl$_3$) δ ppm: 6.81 (d, J=4.0 Hz, 1H), 5.63 (s, 1H), 4.76 (dt, J=10.9, 4.5 Hz, 1H), 3.44 (dd, J=11.7, 4.1 Hz, 1H), 3.17 (d, J=11.8 Hz, 1H), 2.11 (s, 3H), 2.00 (d, J=12.0 Hz, 1H), 1.85 (dt, J=6.9, 2.5 Hz, 1H), 1.69 (d, J=11.0 Hz, 2H), 1.55-1.26 (m, 3H), 1.11-1.00 (m, 2H), 0.91 (dd, J=6.8, 9.8 Hz, 6H), 0.76 (d, J=7.0 Hz, 3H).

Preparation of [(1R,2S,5R)-2-isopropyl-5-methyl-cyclohexyl] (2S)-5-(5-amino-2,7-dioxo-6H-thiazolo[4,5-d]pyrimidin-3-yl)-1,3-oxathiolane-2-carboxylate

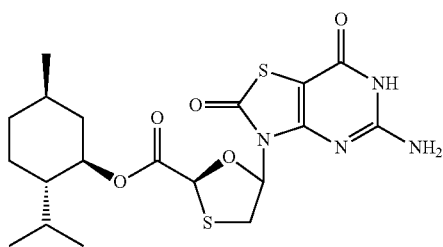

2d

To a suspension of 5-amino-3,6-dihydrothiazolo[4,5-d]pyrimidine-2,7-dione (736 mg, 4 mmol) in ACN (25 mL) was added BSA (2.44 g, 12 mmol). The reaction mixture was heated with stirring at 70° C. for 0.5 hour under argon to form a clear solution. After concentration, the white solid was re-dissolved in DCM (25 mL). To the resulting DCM solution was added [(1R,2S,5R)-2-isopropyl-5-methyl-cyclohexyl] (2S,5S)-5-acetoxy-1,3-oxathiolane-2-carboxylate (660 mg, 2 mmol) and TMSI (800 mg, 4 mmol) in sequence, and the mixture was further stirred at 40° C. for 14 hours. After the reaction was completed, the reaction mixture was quenched with saturated $NaHCO_3$ solution (30 mL). The organic layer was separated and the aqueous phase was extracted with DCM (30 mL) twice. The combined organic phase was washed with brine, dried over $MgSO_4$ and filtered. After concentration, the residue was purified by column chromatography on silica gel (eluting with 1:50 to 1:10 methanol in DCM) to afford [(1R,2S,5R)-2-isopropyl-5-methyl-cyclohexyl] (2S)-5-(5-amino-2,7-dioxo-6H-thiazolo[4,5-d]pyrimidin-3-yl)-1,3-oxathiolane-2-carboxylate (compound 2d) 620 mg as a yellow solid. MS obsd. (ESI⁻) [(M−H)⁻]: 453.

Preparation of 5-amino-3-[(2S)-2-(hydroxymethyl)-1,3-oxathiolan-5-yl]-6H-thiazolo[4,5-d]pyrimidine-2,7-dione

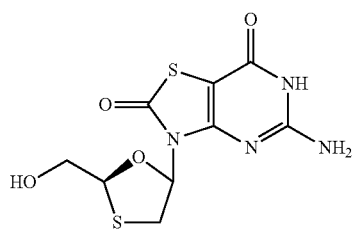

2

To a solution of [(1R,2S,5R)-2-isopropyl-5-methyl-cyclohexyl] (2S)-5-(5-amino-2,7-dioxo-6H-thiazolo[4,5-d]pyrimidin-3-yl)-1,3-oxathiolane-2-carboxylate (454 mg, 1 mmol) in THF (25 mL) was added $LiAlH_4$ solution (2.4 M in THF, 0.8 mL, 2 mmol) at 0° C. under argon. After being stirred at 0° C. for another 0.5 hour, $Na_2SO_4 \cdot 10H_2O$ (644 mg, 2 mmol) was added and the reaction mixture was stirred at room temperature for another 0.5 hour. The suspension was filtered and the filtrate was concentrated in vacuo to give the residue which was purified by preparative HPLC to afford 5-amino-3-[(2S,5R)-2-(hydroxymethyl)-1,3-oxathiolan-5-yl]-6H-thiazolo[4,5-d]pyrimidine-2,7-dione (Example 2-A) 12.4 mg and 5-amino-3-[(2S,5R)-2-(hydroxymethyl)-1,3-oxathiolan-5-yl]-6H-thiazolo[4,5-d]pyrimidine-2,7-dione (Example 2-B) as white solid. The configuration of Example 2-A and Example 2-B were determined by NOESY.

Example 2-A 13.1 mg, ¹H NMR (400 MHz, $CD_3OD$) δ ppm: 6.31 (dd, J=5.5, 9.4 Hz, 1H), 5.22 (dd, J=4.3, 5.3 Hz, 1H), 4.06-4.15 (m, 1H), 3.69-3.89 (m, 2H), 3.11 (dd, J=5.5, 10.4 Hz, 1H). MS obsd. (ESI⁻) [(M−H)⁻]: 301.

Example 2-B 16.9 mg, ¹H NMR (400 MHz, $CD_3OD$) δ ppm: 6.58-6.51 (m, 1H), 5.75-5.70 (m, 1H), 4.02-3.95 (m, 1H), 3.81-3.69 (m, 2H), 3.42-3.37 (m, 1H). MS obsd. (ESI⁻) [(M−H)⁻]: 301.

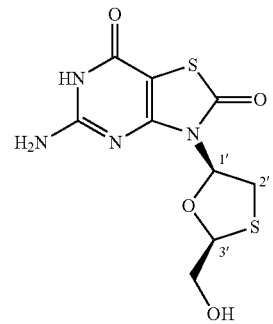

Example 2-A

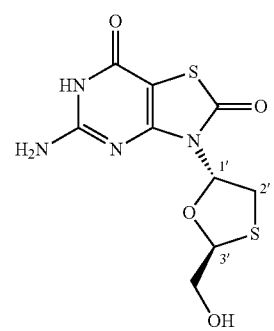

Example 2-B

For Example 2-A, NOESY correlation of 1'-H and 3'-H was observed; and for Example 2-B, NOESY correlation of 1'-H and 3'-H was not observed.

Example 3

5-Amino-3-[(2S)-2-(hydroxymethyl)-1,3-oxathiolan-5-yl]thiazolo[4,5-d] pyrimidin-2-one

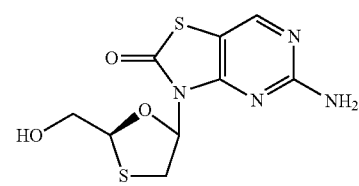

3

Preparation of [(1R,2S,5R)-2-isopropyl-5-methyl-cyclohexyl] (2S)-5-(5-amino-2-oxo-thiazolo [4,5-d]pyrimidin-3-yl)-1,3-oxathiolane-2-carboxylate

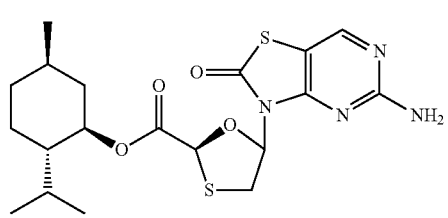

3a

To a suspension of 5-amino-3H-thiazolo[4,5-d]pyrimidin-2-one (CAS #: 848691-22-5, commercially available from Shanghai Shao Yuan Co. Ltd., 672 mg, 4 mmol) in acetonitrile (25 mL) was added BSA (2.44 g, 12 mmol). The reaction mixture was stirred at 70° C. for 0.5 hour under argon to form a clear solution. After concentration, the white solid was re-dissolved in DCM (25 mL), and to this DCM solution were added [(1R,2S,5R)-2-isopropyl-5-methyl-cyclohexyl] (2S,5S)-5-acetoxy-1,3-oxathiolane-2-carboxylate (660 mg, 2 mmol) and TMSI (800 mg, 4 mmol) in sequence. After being heated with stirring at 40° C. for 14 hours, the reaction mixture was quenched with saturated NaHCO$_3$ solution (30 mL). The organic layer was separated and the aqueous phase was extracted with DCM (30 mL) twice. The organic layer was combined and washed with brine, dried over MgSO$_4$ and filtered. After concentration, the residue was purified by flash column chromatography on silica gel to afford [(1R,2S,5R)-2-isopropyl-5-methyl-cyclohexyl] (2S)-5-(5-amino-2-oxo-thiazolo[4,5-d]pyrimidin-3-yl)-1,3-oxathiolane-2-carboxylate (compound 3a) 277 mg as a white solid. MS obsd. (ESI$^+$) [(M+H)$^+$]: 439.

Preparation of 5-amino-3-[(2S)-2-(hydroxymethyl)-1,3-oxathiolan-5-yl]thiazolo[4,5-d] pyrimidin-2-one

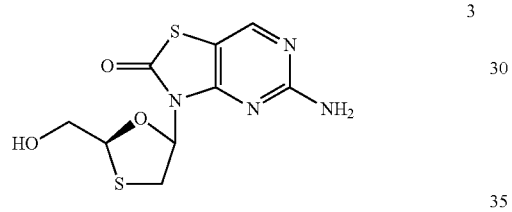

3

To a solution of [(1R,2S,5R)-2-isopropyl-5-methyl-cyclohexyl] (2S)-5-(5-amino-2-oxo-thiazolo[4,5-d]pyrimidin-3-yl)-1,3-oxathiolane-2-carboxylate (277 mg, 0.68 mmol) in MeOH (40 mL) was added NaBH$_4$ (160 mg, 4 mmol) at 0° C. After being stirred at 0° C. for another 0.5 hour, the reaction solution was quenched by NH$_4$Cl solution (1 mL). The resulting mixture was concentrated in vacuo and the residue was purified by preparative HPLC to afford 5-amino-3-[(2S,5R)-2-(hydroxymethyl)-1,3-oxathiolan-5-yl]thiazolo[4,5-d]pyrimidin-2-one (Example 3-A) and 5-amino-3-[(2S,5S)-2-(hydroxymethyl)-1,3-oxathiolan-5-yl]thiazolo[4,5-d]pyrimidin-2-one (Example 3-B). The configuration of Example 3-A and Example 3-B were determined by NOESY.

Example 3-A 11.2 mg, $^1$H NMR (400 MHz, CD$_3$OD) δ ppm: 8.24 (s, 1H), 6.41 (dd, J=9.3, 5.5 Hz, 1H), 5.25 (dd, J=5.5, 4.3 Hz, 1H), 4.14 (dd, J=10.4, 9.3 Hz, 1H), 3.76-3.87 (m, 2H), 3.15 (dd, J=10.4, 5.5 Hz, 1H). MS obsd. (ESI$^+$) [(M+H)$^+$]: 287.

Example 3-B 13.7 mg, $^1$H NMR (400 MHz, CD$_3$OD) δ ppm: 8.22 (s, 1H), 6.64 (t, J=7.0 Hz, 1H), 5.76 (dd, J=4.3, 5.5 Hz, 1H), 4.04-3.97 (m, 1H), 3.77 (dd, J=4.8, 15.3 Hz, 2H), 3.47-3.40 (m, 1H). MS obsd. (ESI$^+$) [(M+H)$^+$]: 287.

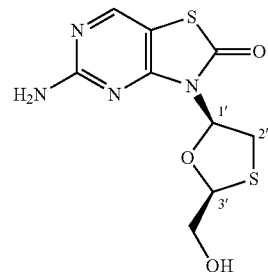

Example 3-A

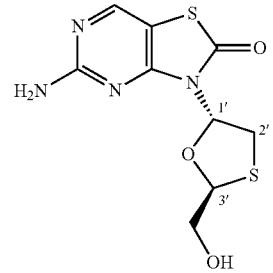

Example 3-B

For Example 3-A, NOESY correlation of 1'-H and 3'-H was observed; and for Example 3-B, NOESY correlation of 1'-H and 3'-H was not observed.

Example 4

5-Amino-3-[(2S,5R)-2-[cyclopropyl(hydroxy)methyl]-1,3-oxathiolan-5-yl]-6H-thiazolo[4,5-d]pyrimidine-2,7-dione

4

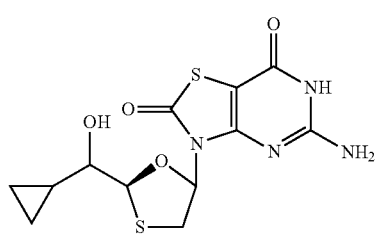

Preparation of [(1R,2S,5R)-2-isopropyl-5-methyl-cyclohexyl] (2S,5R)-5-(5-amino-2,7-dioxo-6H-thiazolo[4,5-d]pyrimidin-3-yl)-1,3-oxathiolane-2-carboxylate and [(1R,2S,5R)-2-isopropyl-5-methyl-cyclohexyl] (2S,5S)-5-(5-amino-2,7-dioxo-6H-thiazolo[4,5-d]pyrimidin-3-yl)-1,3-oxathiolane-2-carboxylate

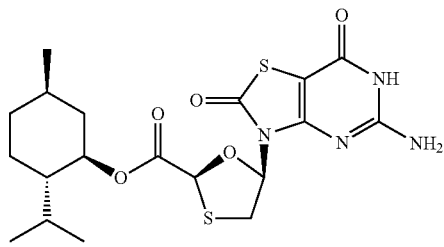

4a-R

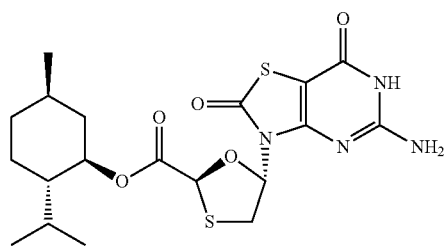

4a-S

[(1R,2S,5R)-2-isopropyl-5-methyl-cyclohexyl] (2S)-5-(5-amino-2,7-dioxo-6H-thiazolo[4,5-d]pyrimidin-3-yl)-1,3-oxathiolane-2-carboxylate (4.0 g, 7.3 mmol) was further purified and separated by preparative HPLC to afford [(1R,2S,5R)-2-isopropyl-5-methyl-cyclohexyl] (2S,5R)-5-(5-amino-2,7-dioxo-6H-thiazolo[4,5-d]pyrimidin-3-yl)-1,3-oxathiolane-2-carboxylate (compound 4a-R) 2.0 g and [(1R,2S,5R)-2-isopropyl-5-methyl-cyclohexyl] (2S,5S)-5-(5-amino-2,7-dioxo-6H-thiazolo[4,5-d]pyrimidin-3-yl)-1,3-oxathiolane-2-carboxylate (compound 4a-S). The configuration of compound 4a-R and compound 4a-S were determined by NOESY in analogy to Example 2-A and 2-B.

Compound 4a-R: 2.0 g, $^1$H NMR (400 MHz, DMSO-$d_6$) δ ppm: 11.20-11.40 (br.s., 1H), 6.83-7.19 (br. s., 2H), 6.18 (dd, J=5.71, 8.22 Hz, 1H), 5.66 (s, 1H), 4.63 (d, J=4.39 Hz, 1H), 4.18 (dd, J=8.34, 10.35 Hz, 1H), 3.35-3.42 (m, 1H), 1.78-1.95 (m, 2H), 1.63 (dd, J=2.95, 10.10 Hz, 2H), 1.30-1.56 (m, 2H), 0.77-1.14 (m, 9H), 0.70 (d, J=6.90 Hz, 3H). MS obsd. (ESI$^-$) [(M−H)$^-$]: 453.

Compound 4a-S: 530 mg, $^1$H NMR (400 MHz, DMSO-$d_6$) δ ppm: 11.27 (br. s., 1H), 6.99 (br. s., 2H), 6.55 (t, J=6.84 Hz, 1H), 5.86-5.97 (m, 1H), 4.67 (dt, J=4.39, 10.92 Hz, 1H), 3.90 (dd, J=7.09, 10.85 Hz, 1H), 3.49 (dd, J=6.71, 10.85 Hz, 1H), 1.79-1.94 (m, 2H), 1.64 (d, J=11.42 Hz, 2H), 1.32-1.56 (m, 2H), 0.81-1.13 (m, 9H), 0.72 (d, J=6.90 Hz, 3H). MS obsd. (ESI$^-$) [(M−H)$^-$]: 453.

Preparation of (2S,5R)-5-(5-amino-2,7-dioxo-6H-thiazolo[4,5-d]pyrimidin-3-yl)-N-methoxy-N-methyl-1,3-oxathiolane-2-carboxamide

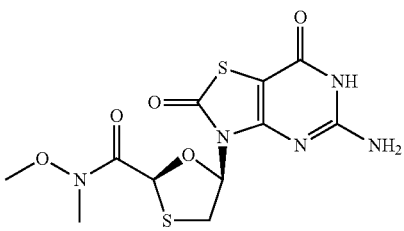

4b

To a solution [(1R,2S,5R)-2-isopropyl-5-methyl-cyclohexyl] (2S,5R)-5-(5-amino-2,7-dioxo-6H-thiazolo [4,5-d]pyrimidin-3-yl)-1,3-oxathiolane-2-carboxylate (0.60 g, 1.3 mmol) in the mixture of THF (15 mL) and MeOH (5 mL) was added LiOH.H$_2$O (0.13 g, 3.3 mmol). After being stirred at 0° C. for 2 hours, N,O-dimethylhydroxylamine hydrochloride (0.32 g, 3.3 mmol) and 4-(4,6-dimethoxy-1,3,5-triazin-2-yl)-4-methylmorpholinium chloride (0.91 g, 3.3 mmol) were added. The solution was stirred at room temperature overnight. After concentration, the residue was purified by flash column chromatography on silica gel (eluting with 1:20 methanol in dichloromethane) to afford (2S,5R)-5-(5-amino-2,7-dioxo-6H-thiazolo[4,5-d]pyrimidin-3-yl)-N-methoxy-N-methyl-1,3-oxathiolane-2-carboxamide (compound 4b) 0.45 g as a white solid. MS obsd. (ESI$^-$) [(M−H)$^-$]: 358.

Preparation of 5-amino-3-[(2S,5R)-2-(cyclopropanecarbonyl)-1,3-oxathiolan-5-yl]-6H-thiazolo[4,5-d]pyrimidine-2,7-dione

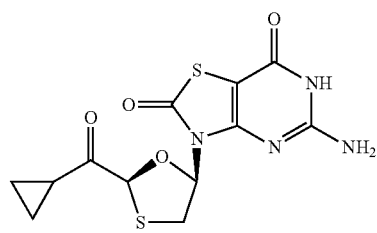

4c

To a solution of (2S,5R)-5-(5-amino-2,7-dioxo-6H-thiazolo[4,5-d]pyrimidin-3-yl)-N-methoxy-N-methyl-1,3-oxathiolane-2-carboxamide (450 mg, 1.2 mmol) in THF (20 mL) was added cyclopropyl magnesium bromide (0.7 M in THF, 7 mL, 4.9 mmol) dropwise via additional funnel at room temperature under argon. After the reaction was completed, the reaction was quenched by saturated NH$_4$Cl solution, extracted by EtOAc (30 mL) three times. The combined organic layer was concentrated to give a crude product which was further purified by flash column chromatography on silica gel (eluting with 1:20 methanol in dichloromethane) to afford 5-amino-3-[(2S,5R)-2-(cyclopropanecarbonyl)-1,3-oxathiolan-5-yl]-6H-thiazolo[4,5-d]pyrimidine-2,7-dione (compound 4c) 340 mg as a white solid.

Compound 4c: $^1$H NMR (400 MHz, DMSO-d6) δ ppm: 11.31 (s, 1H), 6.90-7.09 (m, 2H), 6.25 (dd, J=9.2, 5.3 Hz, 1H), 5.48 (s, 1H), 4.16 (t, J=9.7 Hz, 1H), 3.40 (dd, J=10.3, 5.4 Hz, 1H), 2.58-2.65 (m, 1H), 0.93-1.11 (m, 3H), 0.81 (d, J=4.4 Hz, 1H). MS obsd. (ESI$^-$) [(M–H)$^-$]: 339.

Preparation of 5-amino-3-[(2S,5R)-2-[cyclopropyl(hydroxy)methyl]-1,3-oxathiolan-5-yl]-6H-thiazolo[4,5-d]pyrimidine-2,7-dione (Example 4)

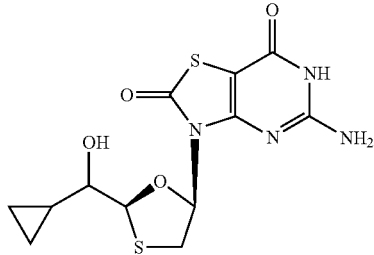

To a solution of 5-amino-3-[(2S,5R)-2-(cyclopropanecarbonyl)-1,3-oxathiolan-5-yl]-6H-thiazolo[4,5-d]pyrimidine-2,7-dione (600 mg, 0.3 mmol) in MeOH (15 mL) was added NaBH$_4$ (38 mg, 1 mmol) at 0° C. The resulting reaction mixture was stirred at 0° C. until the reaction was completed. After being adjusted to pH7.0 with HOAc (102 mg, 1.7 mmol), the reaction was concentrated in vacuo. The residue was purified and separated by preparative HPLC to afford Example 4-A (the diastereomer 1) and Example 4-B (the diastereomer 2) as white solid.

Example 4-A 73 mg, $^1$H NMR (400 MHz, CD$_3$OD) δ ppm: 6.30 (dd, J=9.3, 5.8 Hz, 1H), 5.20 (d, J=5.5 Hz, 1H), 3.99-4.06 (m, 1H), 3.12-3.17 (m, 2H), 0.93-1.02 (m, 1H), 0.38-0.58 (m, 4H). MS obsd. (ESI$^+$) [(M+H)$^+$]: 343.

Example 4-B 18 mg, $^1$H NMR (400 MHz, CD$_3$OD) δ ppm: 6.32 (dd, J=9.7, 5.4 Hz, 1H), 5.26 (d, J=3.5 Hz, 1H), 3.86-3.98 (m, 1H), 3.25 (dd, J=8.3, 3.8 Hz, 1H), 3.08-3.16 (m, 1H), 0.89-0.99 (m, 1H), 0.32-0.58 (m, 4H). MS obsd. (ESI$^+$) [(M+H)$^+$]: 343.

Example 5

5-Amino-3-[(2S,5R)-2-[-cyclopropyl(hydroxy)methyl]-1,3-oxathiolan-5-yl]thiazolo[4,5-d]pyrimidin-2-one

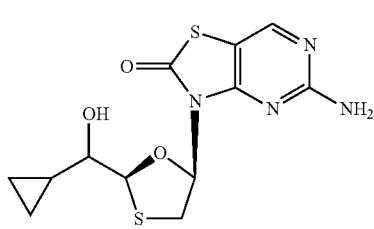

Preparation of [(1R,2S,5R)-2-isopropyl-5-methyl-cyclohexyl] (2S,5R)-5-(5-amino-2-oxo-thiazolo[4,5-d]pyrimidin-3-yl)-1,3-oxathiolane-2-carboxylate and [(1R,2S,5R)-2-isopropyl-5-methyl-cyclohexyl] (2S,5S)-5-(5-amino-2-oxo-thiazolo[4,5-d]pyrimidin-3-yl)-1,3-oxathiolane-2-carboxylate

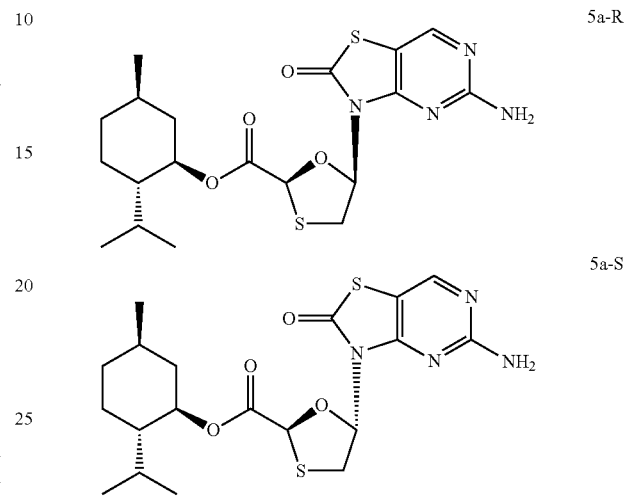

A suspension of 5-amino-3H-thiazolo[4,5-d]pyrimidin-2-one (6.0 g, 36 mmol) and BSA (24.0 g, 118 mmol) in DCE (250 mL) was heated at 85° C. for 1 hour. The reaction mixture was cooled to 0° C., to the above mixture was added a solution of [(1R,2S,5R)-2-isopropyl-5-methyl-cyclohexyl] (2S,5S)-5-acetoxy-1,3-oxathiolane-2-carboxylate (9.0 g, 27 mmol) in DCE (10 mL), followed by TMSI (14 g, 70 mmol) dropwise. The reaction mixture was stirred at 60° C. for 5 hours, quenched by aqueous NaHCO$_3$ solution, and then extracted with EtOAc. The organic layer was washed with brine, dried over anhydrous Na$_2$SO$_4$ and concentrated to give the crude product as an oil, which was purified by column chromatography on silica gel (eluting with 1:100 to 1:50 methanol in dichloromethane) to give [(1R,2S,5R)-2-isopropyl-5-methyl-cyclohexyl] (2S)-5-(5-amino-2-oxo-thiazolo[4,5-d]pyrimidin-3-yl)-1,3-oxathiolane-2-carboxylate (compound 3a) 7.7 g as a mixture of two isomers, which was further purified and separated by preparative HPLC to give the desired beta isomer [(1R,2S,5R)-2-isopropyl-5-methyl-cyclohexyl] (2S,5R)-5-(5-amino-2-oxo-thiazolo[4,5-d]pyrimidin-3-yl)-1,3-oxathiolane-2-carboxylate (compound 5a-R) and [(1R,2S,5R)-2-isopropyl-5-methyl-cyclohexyl] (2S,5S)-5-(5-amino-2-oxo-thiazolo[4,5-d]pyrimidin-3-yl)-1,3-oxathiolane-2-carboxylate (compound 5a-S) as white solid. The configuration of compound 5a-R and compound 5a-S were determined by NOESY in analogy to Example 2-A and 2-B.

Compound 5a-R: 2.8 g, $^1$H NMR (400 MHz, CDCl$_3$) δ ppm: 8.17 (s, 1H), 6.44 (m, 1H), 5.51 (s, 1H), 5.12 (bs, 2H), 4.78 (m, 1H), 4.47 (m, 1H), 3.16 (m, 1H), 2.00 (m, 1H), 1.79 (m, 1H), 1.62 (m, 2H), 1.38 (m, 2H), 0.98 (m, 2H), 0.9-0.72 (m, 10H). MS obsd. (ESI$^+$) [(M+H)$^+$]: 439.

Compound 5a-S: 1.5 g, $^1$H NMR (400 MHz, CDCl$_3$) δ ppm: 8.17 (s, 1H), 6.90 (t, J=4.8 Hz, 1H), 5.79 (s, 1H), 5.13 (bs, 2H), 4.80 (m, 1H), 4.02 (m, 1H), 3.42 (m, 1H), 2.04 (m, 1H), 1.87 (m, 1H), 1.69 (m, 2H), 1.47 (m, 2H), 0.96 (m, 2H), 0.90-0.75 (m, 7H), 0.77 (d, J=8.0 Hz, 3H). MS obsd. (ESI$^+$) [(M+H)$^+$]: 439.

Preparation of (2S,5R)-5-(5-amino-2-oxo-thiazolo[4,5-d]pyrimidin-3-yl)-N-methoxy-N-methyl-1,3-oxathiolane-2-carboxamide

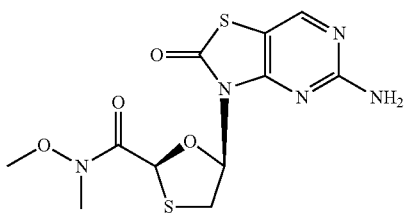

5b

A solution of [(1R,2S,5R)-2-isopropyl-5-methyl-cyclohexyl] (2S,5R)-5-(5-amino-2-oxo-thiazolo[4,5-d]pyrimidin-3-yl)-1,3-oxathiolane-2-carboxylate (3.0 g, 7.5 mmol) in 80% TFA aqueous (20 mL) was stirred at 50° C. for 16 hours, and then concentrated to give the crude acid as a white solid, which was re-dissolved in THF (40 mL). To the above mixture was added N-methoxymethylamine hydrochloride (2.1 g, 22 mmol), DIPEA (14.5 g, 112 mmol) and HATU (8.36 g, 22 mol) at room temperature. After being stirred at room temperature for 16 hours, the reaction mixture was diluted with DCM, washed by water and brine, dried over anhydrous Na$_2$SO$_4$, and concentrated to give the crude product which was purified by flash chromatography on silica gel (eluting with 1:100 to 1:50 methanol in dichloromethane) to give the (2S,5R)-5-(5-amino-2-oxo-thiazolo[4,5-d]pyrimidin-3-yl)-N-methoxy-N-methyl-1,3-oxathiolane-2-carboxamide (compound 5b) 2.1 g as a white solid.

Compound 5b: $^1$H NMR (400 MHz, CDCl$_3$) δ ppm: 8.16 (s, 1H), 6.42 (m, 1H), 5.83 (s, 1H), 5.14 (bs, 2H), 4.46 (t, J=9.6 Hz, 1H), 3.72 (s, 3H), 3.23 (s, 3H), 3.15 (m, 1H). MS obsd. (ESI$^+$) [(M+H)$^+$]: 344.

Preparation of (2S,5R)—N-methoxy-5-[5-[[(4-methoxyphenyl)-diphenyl-methyl]amino]-2-oxo-thiazolo[4,5-d]pyrimidin-3-yl]-N-methyl-1,3-oxathiolane-2-carboxamide

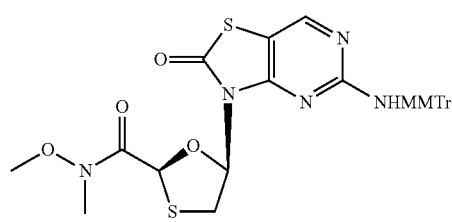

5c

To a solution of (2S,5R)-5-(5-amino-2-oxo-thiazolo[4,5-d]pyrimidin-3-yl)-N-methoxy-N-methyl-1,3-oxathiolane-2-carboxamide (2.1 g, 6.1 mmol) in DCM (30 mL) was added collidine (1.45 g, 12 mmol), AgNO$_3$ (2.04 g, 12 mmol) and MMTrCl (3.8 g, 12 mmol) at room temperature. After being stirred at room temperature for 16 hours, the reaction mixture was diluted with DCM, filtered to remove the solid. The filtrate was washed with water and brine, dried over anhydrous Na$_2$SO$_4$ and concentrated to give the crude product, which was purified by flash chromatography on silica gel (eluting with 1:100 to 2:1 ethyl acetate in petroleum ether) to give (2S,5R)—N-methoxy-5-[5-[[(4-methoxyphenyl)-diphenyl-methyl]amino]-2-oxo-thiazolo[4,5-d]pyrimidin-3-yl]-N-methyl-1,3-oxathiolane-2-carboxamide (compound 5c) 3.6 g as a yellow solid. (ESI$^+$) [(M+H)$^+$]: 616.

Preparation of 3-[(2S,5R)-2-[cyclopropyl(hydroxy)methyl]-1,3-oxathiolan-5-yl]-5-[[(4-methoxyphenyl)-diphenyl-methyl]amino]thiazolo[4,5-d]pyrimidin-2-one

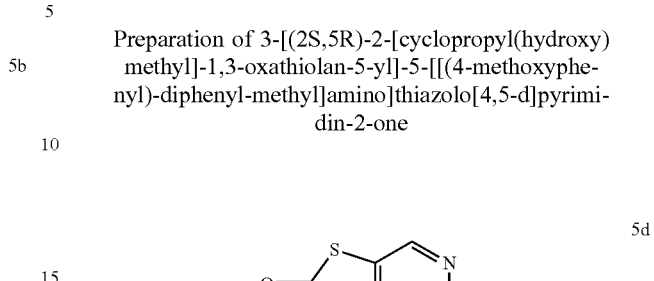

5d

To a solution of (2S,5R)—N-methoxy-5-[5-[[(4-methoxyphenyl)-diphenyl-methyl]amino]-2-oxo-thiazolo[4,5-d]pyrimidin-3-yl]-N-methyl-1,3-oxathiolane-2-carboxamide (3 g, 5 mmol) in THF (40 mL) was added Grignard reagent, cyclopropylmagnesium bromide (0.5 M, 25 mL) at 0° C. The reaction mixture was stirred at 0° C. for 30 min. The reaction was quenched with saturated NH$_4$Cl solution and extracted with EtOAc. The organic layer was dried and concentrated to give the crude product, which was re-dissolved in MeOH (50 mL). To the above mixture was added NaBH$_4$ (2.0 g, 540 mmol) at 0° C. The reaction mixture was stirred at room temperature for 30 min. The reaction was quenched with saturated NH$_4$Cl solution and extracted with DCM. The organic layer was dried over anhydrous Na$_2$SO$_4$ and concentrated to give the crude product, which was purified by flash chromatography on silica gel (eluting with 1:100 to 1:1 ethyl acetate in petroleum ether) to give 3-[(2S,5R)-2-[cyclopropyl(hydroxy)methyl]-1,3-oxathiolan-5-yl]-5-[[(4-methoxyphenyl)-diphenyl-methyl]amino]thiazolo[4, 5-d]pyrimidin-2-one (compound 5d) 1.8 gas a yellow solid. (ESI$^+$) [(M+H)$^+$]: 599.

Preparation of 5-amino-3-[(2S,5R)-2-[cyclopropyl(hydroxy)methyl]-1,3-oxathiolan-5-yl]thiazolo[4,5-d]pyrimidin-2-one

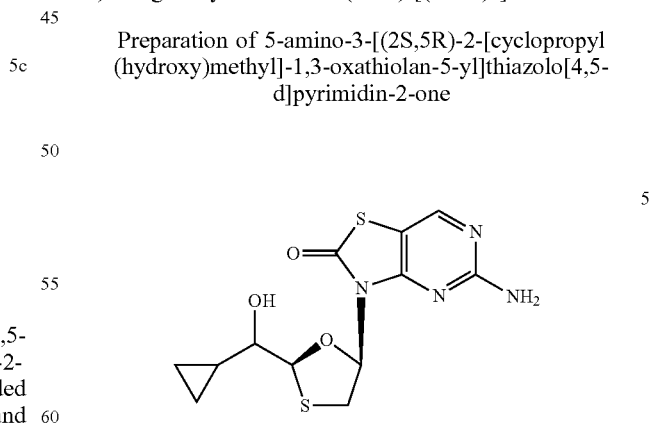

5

A solution of 3-[(2S,5R)-2-[cyclopropyl(hydroxy)methyl]-1,3-oxathiolan-5-yl]-5-[[(4-methoxyphenyl)-diphenyl-methyl]amino]thiazolo[4,5-d]pyrimidin-2-one (1 g, 1.67 mmol) in 50% HCOOH aqueous solution was stirred at room temperature for 1 hour. The reaction mixture was concentrated to give the crude product which was purified and separated by preparative HPLC to give Example 5-A (the diastereomer 1) and Example 5-B (the diastereomer 2) as white solid.

Example 5-A 120 mg, $^1$H NMR (400 MHz, CD$_3$OD) δ ppm: 8.23 (s, 1H), 6.36 (m, 1H), 5.21 (d, J=5.6 Hz, 1H), 4.04 (t, J=10.0 Hz, 1H), 3.16 (m, 2H), 0.97-0.39 (m, 5H). MS obsd. (ESI$^+$) [(M+Na)$^+$]: 349.

Example 5-B 81 mg, $^1$H NMR (400 MHz, CD$_3$OD) δ ppm: 8.25 (s, 1H), 6.38 (m, 1H), 5.27 (d, J=3.6 Hz, 1H), 3.96 (t, J=10.0 Hz, 1H), 3.26 (m, 1H), 3.13 (m, 1H), 0.94-0.32 (m, 5H). MS obsd. (ESI$^+$) [(M+Na)$^+$]: 349.

Example 6

[[(2S,5R)-5-(5-Amino-2-oxo-thiazolo[4,5-d]pyrimidin-3-yl)-1,3-oxathiolan-2-yl]-cyclopropyl-methyl] acetate

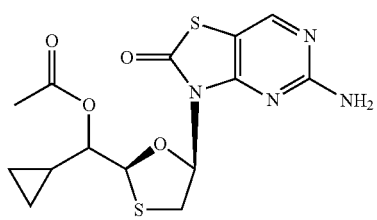

6

Preparation of [cyclopropyl-[(2S,5R)-5-[5-[[(4-methoxyphenyl)-diphenyl-methyl]amino]-2-oxo-thiazolo[4,5-d]pyrimidin-3-yl]-1,3-oxathiolan-2-yl]methyl]acetate

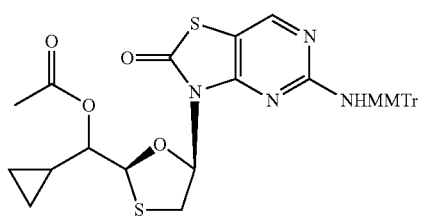

6a

To a solution of 3-[(2S,5R)-2-[cyclopropyl(hydroxy) methyl]-1,3-oxathiolan-5-yl]-5-[[(4-methoxy phenyl)-diphenyl-methyl]amino]thiazolo[4,5-d]pyrimidin-2-one (1.2 g, 2 mmol) in DCM (10 mL) was added TEA (800 mg, 8 mmol), DMAP (30 mg, 0.2 mmol) and Ac$_2$O (400 mg, 4 mmol) at 0° C. The reaction mixture was stirred at room temperature for 48 hours. After the reaction was completed, the reaction was quenched by water, extracted with DCM. The organic layer was dried and concentrated to give the crude product of [cyclopropyl-[(2S,5R)-5-[5-[[(4-methoxyphenyl)-diphenyl-methyl]amino]-2-oxo-thiazolo[4,5-d]pyrimidin-3-yl]-1,3-oxathiolan-2-yl]methyl] acetate (compound 6a) 1.3 g as a white solid, which was used directly in the next step without further purification. (ESI$^+$) [(M+H)$^+$]: 641.

Preparation of [[(2S,5R)-5-(5-amino-2-oxo-thiazolo[4,5-d]pyrimidin-3-yl)-1,3-oxathiolan-2-yl]-cyclopropyl-methyl] acetate

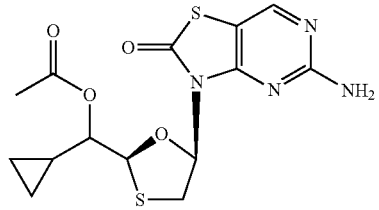

6

A solution of [cyclopropyl-[(2S,5R)-5-[5-[[(4-methoxyphenyl)-diphenyl-methyl]amino]-2-oxo-thiazolo[4,5-d]pyrimidin-3-yl]-1,3-oxathiolan-2-yl]methyl] acetate (1.3 g, 2 mmol) in 90% HCOOH aqueous solution (25 mL) was stirred at room temperature for 1 hour. The reaction mixture was concentrated and the residue was further purified and separated by preparative HPLC to give the Example 6-A (the diastereomer 1) and Example 6-B (the diastereomer 2) as white solid.

Example 6-A 114 mg, $^1$H NMR (400 MHz, CD$_3$OD) δ ppm: 8.20 (s, 1H), 6.34 (m, 1H), 5.34 (d, J=6.4 Hz, 1H), 4.54 (t, J=6.0 Hz, 1H), 4.18 (t, J=8.4 Hz, 1H), 3.31 (t, J=6.0 Hz, 1H), 2.02 (s, 3H), 1.13 (m, 1H), 0.65-0.42 (m, 4H). MS obsd. (ESI$^+$) [(M+Na)$^+$]: 391.

Example 6-B 87 mg, $^1$H NMR (400 MHz, CD$_3$OD) δ ppm: 8.21 (s, 1H), 6.38 (m, 1H), 5.30 (d, J=6.0 Hz, 1H), 4.87 (t, J=7.2 Hz, 1H), 4.19 (t, J=10.0 Hz, 1H), 3.31 (t, J=5.6 Hz, 1H), 2.10 (s, 3H), 1.04 (m, 1H), 0.56-0.33 (m, 4H). MS obsd. (ESI$^+$) [(M+Na)$^+$]: 391.

Example 7

[[(2S,5R)-5-(5-Amino-2,7-dioxo-6H-thiazolo[4,5-d]pyrimidin-3-yl)-1,3-oxathiolan-2-yl]-cyclopropyl-methyl] acetate

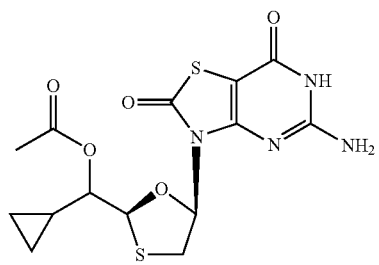

7

Preparation of (2S,5R)—N-methoxy-5-[5-[[(4-methoxyphenyl)-diphenyl-methyl]amino]-2,7-dioxo-6H-thiazolo[4,5-d]pyrimidin-3-yl]-N-methyl-1,3-oxathiolane-2-carboxamide

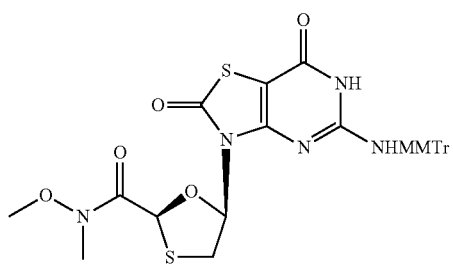

7a

To a solution of (2S,5R)-5-(5-amino-2,7-dioxo-6H-thiazolo[4,5-d]pyrimidin-3-yl)-N-methoxy-N-methyl-1,3-oxathiolane-2-carboxamide (crude 1.4 g, 2.2 mmol) in DCM (10 mL) was added collidine (750 mg, 6 mmol), $AgNO_3$ (1.08 g, 6 mmol) and MMTrCl (1.85 g, 6 mmol) at room temperature. After being stirred at room temperature for 16 hours, the reaction mixture was diluted with DCM, filtered to remove the solid. The filtrate was washed with water and brine, dried and concentrated to give the crude product which was purified by flash chromatography on silica gel (eluting with 1:100 to 2:1 ethyl acetate in petroleum ether) to give (2S,5R)—N-methoxy-5-[5-[[(4-methoxyphenyl)-diphenyl-methyl]amino]-2,7-dioxo-6H-thiazolo[4,5-d]pyrimidin-3-yl]-N-methyl-1,3-oxathiolane-2-carboxamide (compound 7a) 1.2 g as a yellow solid. MS obsd. $(ESI^+)$ $[(M+H)^+]$: 632.

Preparation of 3-[(2S,5R)-2-[cyclopropyl(hydroxy)methyl]-1,3-oxathiolan-5-yl]-5-[[(4-methoxyphenyl)-diphenyl-methyl]amino]-6H-thiazolo[4,5-d]pyrimidine-2,7-dione

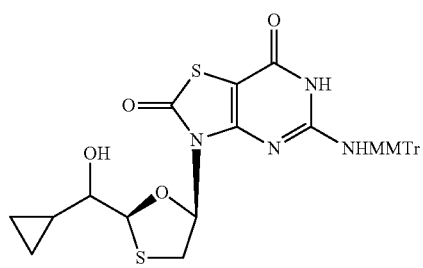

7b

To a solution of (2S,5R)—N-methoxy-5-[5-[[(4-methoxyphenyl)-diphenyl-methyl]amino]-2,7-dioxo-6H-thiazolo[4,5-d]pyrimidin-3-yl]-N-methyl-1,3-oxathiolane-2-carboxamide (140 mg, 0.2 mmol) in THF (2 mL) was added Grignard reagent cyclopropylmagnesium bromide (0.5 M in THF, 1 mL) at 0° C. The reaction mixture was stirred at 0° C. for 30 min. The reaction was quenched by saturated $NH_4Cl$ solution and extracted with EtOAc. The organic layer was dried and concentrated to give the crude product, which was re-dissolved in MeOH (5 mL). To the above mixture was added $NaBH_4$ (41 mg, 1 mmol) at 0° C. The reaction mixture was stirred at room temperature for 30 min. The reaction was quenched by saturated $NH_4Cl$ solution and extracted by DCM. The organic layer was washed with brine, dried and concentrated to give the crude product, which was purified by flash chromatography on silica gel (eluting with 1:100 to 1:1 ethyl acetate in petroleum ether) to afford crude 3-[(2S,5R)-2-[cyclopropyl(hydroxy)methyl]-1,3-oxathiolan-5-yl]-5-[[(4-methoxyphenyl)-diphenyl-methyl]amino]-6H-thiazolo[4,5-d]pyrimidine-2,7-dione (compound 7b) 150 mg as a yellow solid. MS obsd. $(ESI^+)$ $[(M+H)^+]$: 615.

Preparation of [[(2S,5R)-5-(5-amino-2,7-dioxo-6H-thiazolo[4,5-d]pyrimidin-3-yl)-1,3-oxathiolan-2-yl]-cyclopropyl-methyl] acetate

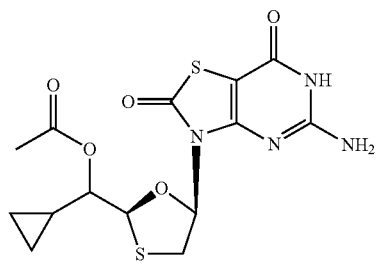

7

The title compound was prepared in analogy to Example 6, by using 3-[(2S,5R)-2-[cyclopropyl(hydroxy)methyl]-1,3-oxathiolan-5-yl]-5-[[(4-methoxyphenyl)-diphenyl-methyl]amino]-6H-thiazolo[4,5-d]pyrimidine-2,7-dione (compound 7b) instead of 3-[(2S,5R)-2-[cyclopropyl(hydroxy)methyl]-1,3-oxathiolan-5-yl]-5-[[(4-methoxyphenyl)-diphenyl-methyl]amino]thiazolo[4,5-d]pyrimidin-2-one (compound 5d). Compound of Example 7 was further purified and separated by preparative HPLC to afford Example 7-A (the diastereomer 1) and Example 7-B (the diastereomer 2) as white solid.

Example 7-A $^1H$ NMR (400 MHz, $CD_3OD$) δ ppm: 6.23 (m, 1H), 5.30 (d, J=6.4 Hz, 1H), 4.54 (m, 1H), 4.15 (t, J=10.0 Hz, 1H), 3.15 (m, 1H), 2.04 (s, 3H), 1.16-0.42 (m, 5H). MS obsd. $(ESI^+)$ $[(M+H)^+]$: 385.

Example 7-B $^1H$ NMR (400 MHz, $CD_3OD$) δ ppm: 6.29 (m, 1H), 5.28 (d, J=6.4 Hz, 1H), 4.79 (m, 1H), 4.15 (t, J=10.0 Hz, 1H), 3.04 (m, 1H), 2.10 (s, 3H), 1.07-0.38 (m, 5H). MS obsd. $(ESI^+)$ $[(M+H)^+]$: 385.

Example 8

5-Amino-3-[(2S,5R)-2-(1-hydroxypropyl)-1,3-oxa-thiolan-5-yl]-6H-thiazolo[4,5-d] pyrimidine-2,7-dione

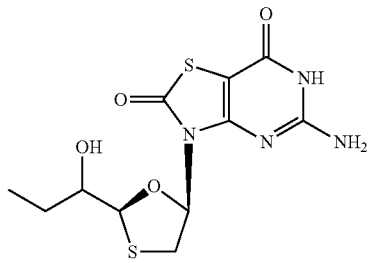

The title compound was prepared in analogy to Example 4, by using ethyl magnesium bromide instead of cyclopropyl magnesium bromide. Compound of Example 8 was further purified and separated by preparative HPLC to afford Example 8-A (the diastereomer 1) and Example 8-B (the diastereomer 2) as white solid.

Example 8-A $^1$H NMR (400 MHz, CD$_3$OD) δ ppm: 6.28 (dd, J=9.3, 5.5 Hz, 1H), 5.10 (d, J=5.3 Hz, 1H), 4.02 (t, J=9.8 Hz, 1H), 3.64 (dt, J=9.0, 4.5 Hz, 1H), 3.12 (dd, J=10.0, 5.5 Hz, 1H), 1.60-1.75 (m, 1H), 1.44-1.56 (m, 1H), 1.02 (t, J=7.5 Hz, 3H). MS obsd. (ESI$^+$) [(M+H)$^+$]: 331.

Example 8-B $^1$H NMR (400 MHz, CD$_3$OD) δ ppm: 6.30 (dd, J=9.5, 5.3 Hz, 1H), 5.12 (d, J=4.3 Hz, 1H), 3.92-4.00 (m, 1H), 3.76-3.82 (m, 1H), 3.09 (dd, J=10.7, 5.4 Hz, 1H), 1.56-1.67 (m, 1H), 1.42-1.53 (m, 1H), 1.02 (t, J=7.4 Hz, 3H). MS obsd. (ESI$^+$) [(M+H)$^+$]:331.

Example 9

5-Amino-3-[(2S,5R)-2-(1-hydroxybutyl)-1,3-oxa-thiolan-5-yl]-6H-thiazolo[4,5-d]pyrimidine-2,7-dione

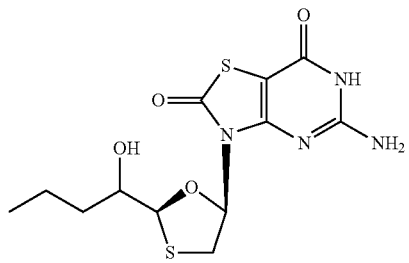

The title compounds were prepared in analogy to Example 4, by using propyl magnesium bromide instead of cyclopropyl magnesium bromide. Compound of Example 9 was further purified and separated by preparative HPLC to afford Example 9-A (the diastereomer 1) and Example 9-B (the diastereomer 2) as white solid.

Example 9-A $^1$H NMR (400 MHz, CD$_3$OD) δ ppm: 6.28 (dd, J=9.3, 5.5 Hz, 1H), 5.08 (d, J=5.3 Hz, 1H), 4.03 (t, J=9.8 Hz, 1H), 3.73 (m, 1H), 3.09-3.16 (m, 1H), 1.40-1.61 (m, 4H), 0.93-1.01 (m, 3H). MS obsd. (ESI$^+$) [(M+H)$^+$]: 345.

Example 9-B $^1$H NMR (400 MHz, CD$_3$OD) δ ppm: 6.30 (dd, J=9.5, 5.5 Hz, 1H), 5.09-5.12 (m, 1H), 3.86-3.98 (m, 2H), 3.05-3.16 (m, 1H), 1.37-1.62 (m, 4H), 0.97 (t, J=7.0 Hz, 3H). MS obsd. (ESI$^+$) [(M+H)$^+$]: 345.

Example 10

5-Amino-3-[(2S,5R)-2-(1-hydroxybut-2-ynyl)-1,3-oxathiolan-5-yl]-6H-thiazolo[4,5-d]pyrimidine-2,7-dione

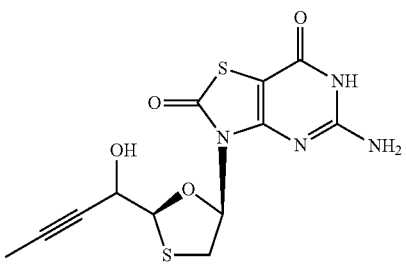

The title compounds were prepared in analogy to Example 4, by using 1-propynyl magnesium bromide instead of cyclopropyl magnesium bromide. Compound of Example 10 was further purified and separated by preparative HPLC to afford Example 10-A (the diastereomer 1) and Example 10-B (the diastereomer 2) as white solid.

Example 10-A $^1$H NMR (400 MHz, CD$_3$OD) δ ppm: 6.35 (dd, J=9.4, 5.6 Hz, 1H), 5.09 (d, J=7.0 Hz, 1H), 4.47-4.51 (m, 1H), 4.08-4.13 (m, 1H), 3.07-3.16 (m, 1H), 1.85 (d, J=2.0 Hz, 3H). MS obsd. (ESI$^+$) [(M+H)$^+$]: 341.

Example 10-B $^1$H NMR (400 MHz, CD$_3$OD) δ ppm: 6.33 (dd, J=9.5, 5.5 Hz, 1H), 5.18 (d, J=4.5 Hz, 1H), 4.57 (dd, J=4.6, 2.4 Hz, 1H), 3.97-4.03 (m, 1H), 3.05-3.17 (m, 1H), 1.85 (d, J=2.0 Hz, 3H). MS obsd. (ESI$^+$) [(M+H)$^+$]: 341.

Example 11

5-Amino-3-[(2S,5R)-2-(1-hydroxybut-2-ynyl)-1,3-oxathiolan-5-yl]thiazolo[4,5-d]pyrimidin-2-one

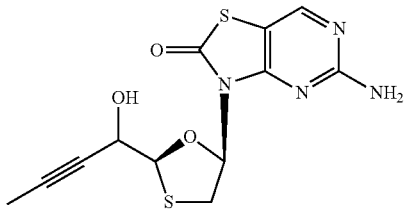

11

Preparation of 3-[(2S,5R)-2-(1-hydroxybut-2-ynyl)-1,3-oxathiolan-5-yl]-5-[[(4-methoxyphenyl)-diphenyl-methyl]amino]thiazolo[4,5-d]pyrimidin-2-one

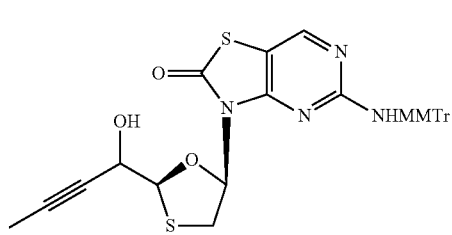

11a

The title compound was prepared in analogy to compound 5d, by using 1-propynyl magnesium bromide instead of cyclopropyl magnesium bromide. (ESI⁺) [(M+H)⁺]: 597.

Preparation of 5-Amino-3-[(2S,5R)-2-(1-hydroxybut-2-ynyl)-1,3-oxathiolan-5-yl]thiazolo[4,5-d]pyrimidin-2-one

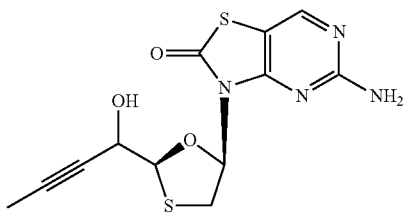

11

The title compound was prepared in analogy to Example 5, by using 3-[(2S,5R)-2-(1-hydroxybut-2-ynyl)-1,3-oxathiolan-5-yl]-5-[[(4-methoxyphenyl)-diphenyl-methyl]amino]thiazolo[4,5-d]pyrimidin-2-one (compound 11a) instead of 3-[(2S,5R)-2-[cyclopropyl(hydroxy)methyl]-1,3-oxathiolan-5-yl]-5-[[(4-methoxyphenyl)-diphenyl-methyl]amino]thiazolo[4,5-d]pyrimidin-2-one (compound 5d). Compound of Example 11 was further purified and separated by preparative HPLC to afford Example 11-A (the diastereomer 1) and Example 11-B (the diastereomer 2) as white solid.

Example 11-A

¹H NMR (400 MHz, CD₃OD) δ ppm: 8.24 (s, 1H), 6.40 (m, 1H), 5.18 (d, J=4.4 Hz, 1H), 4.49 (m, 1H), 4.12 (t, J=9.6 Hz, 1H), 3.11 (m, 1H), 1.83 (d, J=2.4 Hz, 3H). MS obsd. (ESI⁺) [(M+Na)⁺]: 347.

Example 11-B

¹H NMR (400 MHz, CD₃OD) δ ppm: 8.25 (s, 1H), 6.38 (m, 1H), 5.27 (d, J=3.6 Hz, 1H), 4.59 (m, 1H), 4.03 (t, J=10.0 Hz, 1H), 3.10 (m, 1H), 1.82 (d, J=2.0 Hz, 3H). MS obsd. (ESI⁺) [(M+Na)⁺]: 347.

Example 12

1-[(2S,5R)-5-(5-Amino-2-oxo-thiazolo[4,5-d]pyrimidin-3-yl)-1,3-oxathiolan-2-yl] but-2-ynyl acetate

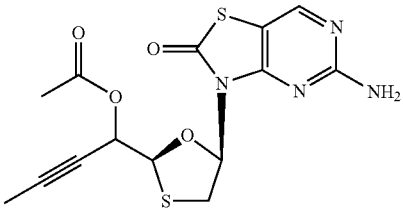

12

The title compound was prepared in analogy to Example 6, by using 3-[(2S,5R)-2-(1-hydroxybut-2-ynyl)-1,3-oxathiolan-5-yl]-5-[[(4-methoxyphenyl)-diphenyl-methyl]amino]thiazolo[4,5-d]pyrimidin-2-one (compound 11a) instead of 3-[(2S,5R)-2-[cyclopropyl(hydroxy)methyl]-1,3-oxathiolan-5-yl]-5-[[(4-methoxyphenyl)-diphenyl-methyl]amino]thiazolo[4,5-d]pyrimidin-2-one (compound 5d). Compound of Example 12 was further purified and separated by preparative HPLC to afford Example 12-A (the diastereomer 1) and Example 12-B (the diastereomer 2) as white solid.

Example 12-A

¹H NMR (400 MHz, CD₃OD) δ ppm: 8.20 (s, 1H), 6.43 (m, 1H), 5.54 (d, J=7.6 Hz, 1H), 5.28 (d, J=8.0 Hz, 1H), 4.19 (t, J=10.0 Hz, 1H), 3.15 (m, 1H), 2.00 (s, 3H), 1.84 (s, 3H). MS obsd. (ESI⁺) [(M+H)⁺]: 367.

Example 12-B

¹H NMR (400 MHz, CD₃OD) δ ppm: 8.22 (s, 1H), 6.42 (m, 1H), 5.94 (m, 1H), 5.26 (d, J=6.4 Hz, 1H), 4.21 (t, J=10.0 Hz, 1H), 3.10 (m, 1H), 2.11 (s, 3H), 1.79 (d, J=2.4 Hz, 3H). MS obsd. (ESI⁺) [(M+H)⁺]: 367.

Example 13

1-[(2S,5R)-5-(5-Amino-2,7-dioxo-6H-thiazolo[4,5-d]pyrimidin-3-yl)-1,3-oxathiolan-2-yl]but-2-ynyl acetate

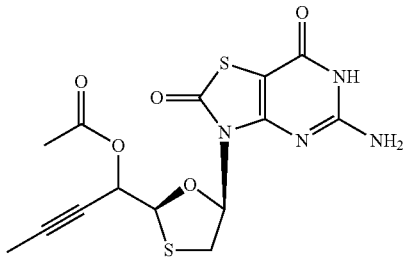

Preparation of 3-[(2S,5R)-2-(1-hydroxybut-2-ynyl)-1,3-oxathiolan-5-yl]-5-[[(4-methoxyphenyl)-diphenyl-methyl]amino]-6H-thiazolo[4,5-d]pyrimidine-2,7-dione

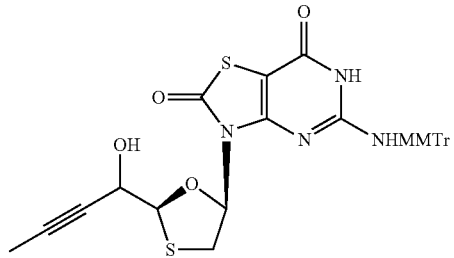

The title compound was prepared in analogy to compound 7b, by using 1-propynyl magnesium bromide instead of cyclopropyl magnesium bromide. MS obsd. (ESI$^+$) [(M+H)$^+$]: 613.

Preparation of 1-[(2S,5R)-5-(5-Amino-2,7-dioxo-6H-thiazolo[4,5-d]pyrimidin-3-yl)-1,3-oxathiolan-2-yl]but-2-ynyl acetate

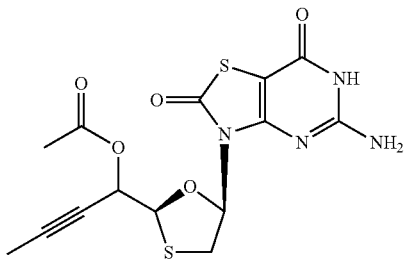

The title compound was prepared in analogy to Example 6, by 3-[(2S,5R)-2-(1-hydroxybut-2-ynyl)-1,3-oxathiolan-5-yl]-5-[[(4-methoxyphenyl)-diphenyl-methyl]amino]-6H-thiazolo[4,5-d]pyrimidine-2,7-dione (compound 13a) instead of 3-[(2S,5R)-2-[cyclopropyl(hydroxy)methyl]-1,3-oxathiolan-5-yl]-5-[[(4-methoxyphenyl)-diphenyl-methyl]amino]thiazolo[4,5-d]pyrimidin-2-one (compound 5d). Compound of Example 13 was further purified and separated by preparative HPLC to afford Example 13-A (the diastereomer 1) and Example 13-B (the diastereomer 2) as white solid.

Example 13-A $^1$H NMR (400 MHz, CD$_3$OD) δ ppm: 6.33 (m, 1H), 5.52 (m, 1H), 5.24 (d, J=8.0 Hz, 1H), 4.16 (t, J=10.0 Hz, 1H), 3.11 (m, 1H), 2.02 (s, 3H), 1.83 (d, J=2.0 Hz, 3H). MS obsd. (ESI$^+$) [(M+H)$^+$]: 383.

Example 13-B $^1$H NMR (400 MHz, CD$_3$OD) δ ppm: 6.32 (m, 1H), 5.85 (m, 1H), 5.23 (d, J=6.0 Hz, 1H), 4.16 (t, J=10.0 Hz, 1H), 3.06 (m, 1H), 2.11 (s, 3H), 1.81 (d, J=2.0 Hz, 3H). MS obsd. (ESI$^+$) [(M+H)$^+$]: 383.

Example 14

5-Amino-3-[(2S,5R)-2-(3-cyclopropyl-1-hydroxy-prop-2-ynyl)-1,3-oxathiolan-5-yl]-6H-thiazolo[4,5-d]pyrimidine-2,7-dione

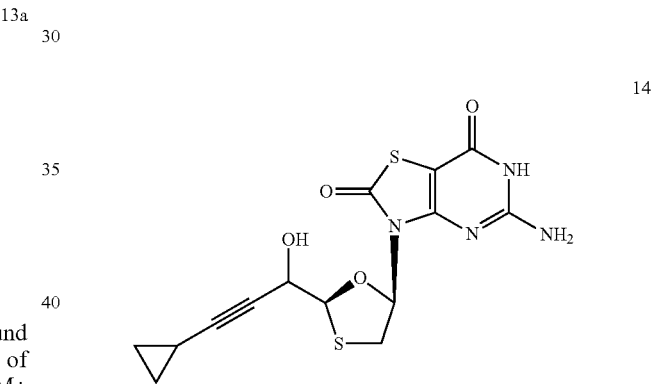

The title compound was prepared in analogy to Example 4, by using (2-cyclopropylethynyl) magnesium bromide instead of cyclopropyl magnesium bromide. Compound of Example 14 was further purified and separated by preparative HPLC to afford Example 14-A (the diastereomer 1) and Example 14-B (the diastereomer 2) as white solid.

Example 14-A $^1$H NMR (400 MHz, CD$_3$OD) δ ppm: 6.34 (dd, J=9.4, 5.6 Hz, 1H), 5.06 (d, J=7.0 Hz, 1H), 4.49 (dd, J=7.0, 1.8 Hz, 1H), 4.04-4.16 (m, 1H), 3.09 (dd, J=10.4, 5.6 Hz, 1H), 1.26-1.35 (m, 1H), 0.74-0.86 (m, 2H), 0.57-0.71 (m, 2H). MS obsd. (ESI$^+$) [(M+H)$^+$]: 367.

Example 14-B $^1$H NMR (400 MHz, CD$_3$OD) δ ppm: 6.33 (dd, J=9.7, 5.4 Hz, 1H), 5.18 (d, J=4.0 Hz, 1H), 4.60 (d, J=2.3 Hz, 1H), 3.97 (t, J=10.0 Hz, 1H), 3.08 (dd, J=10.4, 5.4 Hz, 1H), 1.20-1.37 (m, 1H), 0.74-0.88 (m, 2H), 0.61-0.71 (m, 2H). MS obsd. (ESI$^+$) [(M+H)$^+$]: 367.

Example 15

5-Amino-3-[(2S,5R)-2-(1-hydroxyprop-2-ynyl)-1,3-oxathiolan-5-yl]-6H-thiazolo[4,5-d]pyrimidine-2,7-dione

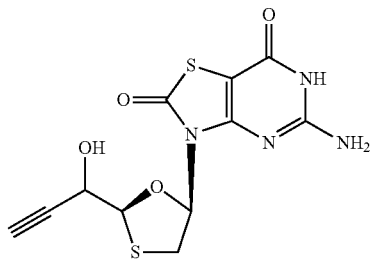

15

The title compound was prepared in analogy to Example 4, by using ethynyl magnesium bromide instead of cyclopropyl magnesium bromide. Compound of Example 15 was further purified and separated by preparative HPLC to afford Example 15-A (the diastereomer 1) and Example 15-B (the diastereomer 2) as white solid.

Example 15-A $^1$H NMR (400 MHz, CD$_3$OD) δ ppm: 6.37 (dd, J=9.5, 5.5 Hz, 1H), 5.16 (d, J=6.5 Hz, 1H), 4.55 (dd, J=6.7, 2.1 Hz, 1H), 4.00-4.21 (m, 1H), 3.04-3.17 (m, 1H), 2.89 (d, J=2.3 Hz, 1H). MS obsd. (ESI$^+$) [(M+H)$^+$]: 327.

Example 15-B $^1$H NMR (400 MHz, CD$_3$OD) δ ppm: 6.35 (dd, J=9.7, 5.4 Hz, 1H), 5.21 (d, J=5.0 Hz, 1H), 4.63 (dd, J=4.8, 2.0 Hz, 1H), 4.03 (t, J=10.0 Hz, 1H), 3.10 (dd, J=10.4, 5.6 Hz, 1H), 2.89 (d, J=2.3 Hz, 1H). MS obsd. (ESI$^+$) [(M+H)$^+$]:327.

Example 16

5-Amino-3-[(2S,5R)-2-(1-hydroxyethyl)-1,3-oxathiolan-5-yl]-6H-thiazolo[4,5-d]pyrimidine-2,7-dione

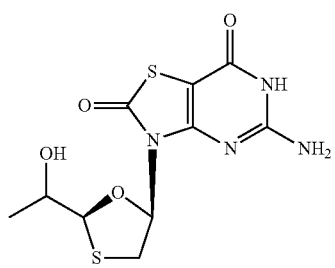

16

The title compound was prepared in analogy to Example 4, by using methyl magnesium iodide instead of cyclopropyl magnesium bromide. Compound of Example 16 was further purified and separated by preparative HPLC to afford Example 16-A (the diastereomer 1) and Example 16-B (the diastereomer 2) as white solid.

Example 16-A $^1$H NMR (400 MHz, CD$_3$OD) δ ppm: 6.29 (dd, J=9.3, 5.5 Hz, 1H), 5.03 (d, J=5.8 Hz, 1H), 4.02-4.09 (m, 1H), 3.96 (q, J=6.2 Hz, 1H), 3.08-3.16 (m, 1H), 1.24 (d, J=6.5 Hz, 3H). MS obsd. (ESI$^+$) [(M+H)$^+$]: 317.

Example 16-B $^1$H NMR (400 MHz, CD$_3$OD) δ ppm: 6.30 (dd, J=9.5, 5.3 Hz, 1H), 5.07 (d, J=4.0 Hz, 1H), 4.03 (dd, J=6.3, 4.0 Hz, 1H), 3.91-3.99 (m, 1H), 3.08 (dd, J=10.4, 5.4 Hz, 1H), 1.21 (d, J=6.5 Hz, 3H). MS obsd. (ESI+) [(M+H)+]:317.

Example 17

5-Amino-3-[(2S,5R)-2-(1-hydroxy-3-methyl-butyl)-1,3-oxathiolan-5-yl]-6H-thiazolo[4,5-d]pyrimidine-2,7-dione

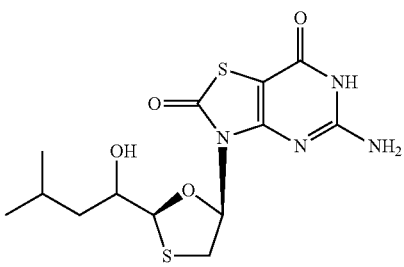

17

The title compounds were prepared in analogy to Example 4, by using isobutyl magnesium bromide instead of cyclopropyl magnesium bromide. Compound of Example 17 was further purified and separated by preparative HPLC to afford Example 17-A (the diastereomer 1) and Example 17-B (the diastereomer 2) as white solid.

Example 17-A $^1$H NMR (400 MHz, CD$_3$OD) δ ppm: 6.28 (dd, J=9.4, 5.6 Hz, 1H), 5.05 (d, J=5.3 Hz, 1H), 3.98-4.08 (m, 1H), 3.80 (ddd, J=7.8, 5.1, 2.6 Hz, 1H), 3.12 (dd, J=10.0, 5.5 Hz, 1H), 1.79-1.97 (m, 1H), 1.48 (ddd, J=14.1, 10.0, 4.3 Hz, 1H), 1.26-1.38 (m, 1H), 0.96 (dd, J=7.9, 6.7 Hz, 6H). MS obsd. (ESI$^+$) [(M+H)$^+$]: 359.

Example 17-B $^1$H NMR (400 MHz, CD$_3$OD) δ ppm: 6.30 (dd, J=9.5, 5.3 Hz, 1H), 5.09 (d, J=4.0 Hz, 1H), 3.92-4.01 (m, 2H), 3.08 (dd, J=10.3, 5.5 Hz, 1H), 1.79-1.93 (m, 1H), 1.37-1.47 (m, 1H), 1.25-1.35 (m, 1H), 0.96 (dd, J=12.3, 6.5 Hz, 6H). MS obsd. (ESI$^+$) [(M+H)$^+$]: 359.

Example 18

5-Amino-3-[(2S,5R)-2-(1-hydroxybut-3-enyl)-1,3-oxathiolan-5-yl]-6H-thiazolo[4,5-d]pyrimidine-2,7-dione

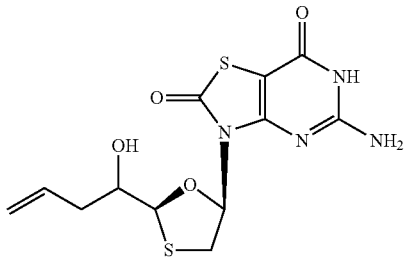

18

The title compound was prepared in analogy to Example 4, by using allyl magnesium bromide instead of cyclopropyl magnesium bromide. Compound of Example 18 was further purified and separated by preparative HPLC to afford Example 18-A (the diastereomer 1) and Example 18-B (the diastereomer 2) as white solid.

Example 18-A $^1$H NMR (400 MHz, CD$_3$OD) δ ppm: 6.29 (dd, J=9.5, 5.3 Hz, 1H), 5.92 (ddt, J=17.2, 10.2, 7.0 Hz, 1H), 5.16 (d, J=4.3 Hz, 1H), 5.10-5.15 (m, 1H), 5.05-5.09 (m, 1H), 4.00 (t, J=9.9 Hz, 1H), 3.78 (dt, J=8.2, 4.3 Hz, 1H), 3.07-3.16 (m, 1H), 2.38-2.46 (m, 1H), 2.26-2.37 (m, 1H). MS obsd. (ESI$^+$) [(M+H)$^+$]: 343.

Example 18-B $^1$H NMR (400 MHz, CD$_3$OD) δ ppm: 6.30 (dd, J=9.7, 5.4 Hz, 1H), 5.90 (dd, J=17.2, 10.4 Hz, 1H), 5.14-5.17 (m, 1H), 5.10-5.14 (m, 1H), 5.08 (d, J=10.0 Hz, 1H), 3.92-4.00 (m, 2H), 3.08 (dd, J=10.5, 5.3 Hz, 1H), 2.31 (dd, J=16.4, 7.7 Hz, 2H). MS obsd. (ESI$^+$) [(M+H)$^+$]: 343.

Example 19

5-Amino-3-[(2S,5R)-2-(1-hydroxypentyl)-1,3-oxathiolan-5-yl]-6H-thiazolo[4,5-d] pyrimidine-2,7-dione

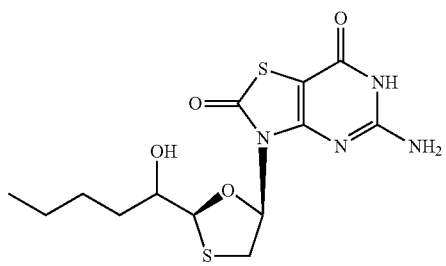

19

The title compound was prepared in analogy to Example 4, by using 1-butylmagnesium bromide instead of cyclopropyl magnesium bromide. Compound of Example 19 was further purified and separated by preparative HPLC to afford Example 19-A (the diastereomer 1) and Example 19-B (the diastereomer 2) as white solid.

Example 19-A $^1$H NMR (400 MHz, CD$_3$OD) δ ppm: 6.28 (dd, J=9.3, 5.5 Hz, 1H), 5.09 (d, J=5.0 Hz, 1H), 4.02 (t, J=9.8 Hz, 1H), 3.67-3.76 (m, 1H), 3.12 (dd, J=10.2, 5.6 Hz, 1H), 1.27-1.67 (m, 6H), 0.86-1.03 (m, 3H). MS obsd. (ESI$^+$) [(M+H)$^+$]: 359.

Example 19-B $^1$H NMR (400 MHz, CD$_3$OD) δ ppm: 6.30 (dd, J=9.5, 5.5 Hz, 1H), 5.09-5.15 (m, 1H), 3.95 (t, J=9.9 Hz, 1H), 3.84-3.90 (m, 1H), 3.08 (dd, J=10.3, 5.3 Hz, 1H), 1.44-1.59 (m, 3H), 1.32-1.43 (m, 3H), 0.94 (t, J=7.0 Hz, 3H). MS obsd. (ESI$^+$) [(M+H)$^+$]:359.

Example 20

5-amino-3-[(2S,5R)-2-[hydroxy(2-thienyl)methyl]-1,3-oxathiolan-5-yl]-6H-thiazolo[4,5-d]pyrimidine-2,7-dione

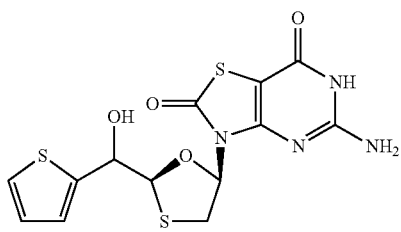

20

The title compound was prepared in analogy to Example 4, by using 2-thienyl magnesium bromide instead of cyclopropyl magnesium bromide. Compound of Example 20 was further purified and separated by preparative HPLC to afford Example 20-A (the diastereomer 1) and Example 20-B (the diastereomer 2) as white solid.

Example 20-A $^1$H NMR (400 MHz, CD$_3$OD) δ ppm: 7.32-7.39 (m, 1H), 7.05-7.16 (m, 1H), 6.96-7.03 (m, 1H), 6.31-6.40 (m, 1H), 5.28-5.34 (m, 1H), 5.09 (d, J=6.3 Hz, 1H), 4.04-4.12 (m, 1H), 3.08-3.17 (m, 1H). MS obsd. (ESI$^+$) [(M+H)$^+$]: 385.

Example 20-B $^1$H NMR (400 MHz, CD$_3$OD) δ ppm: 7.35 (dd, J=5.0, 1.3 Hz, 1H), 7.07 (d, J=3.5 Hz, 1H), 6.99 (dd, J=5.1, 3.6 Hz, 1H), 6.36 (dd, J=9.5, 5.3 Hz, 1H), 5.25-5.36 (m, 2H), 4.00-4.13 (m, 1H), 3.11 (dd, J=10.4, 5.4 Hz, 1H). MS obsd. (ESI$^+$) [(M+H)$^+$]: 385.

Example 21

5-Amino-3-[(2S,4S)-2-(hydroxymethyl)-4-methyl-1,3-oxathiolan-5-yl]-6H-thiazolo[4,5-d]pyrimidine-2,7-dione

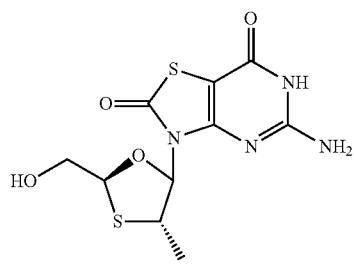

Synthetic Scheme of Example 21

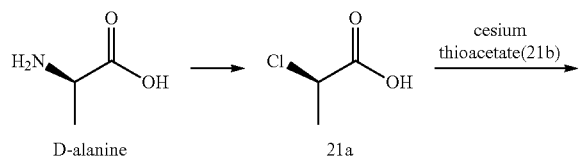

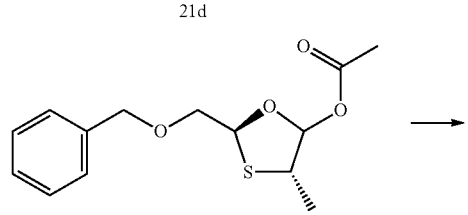

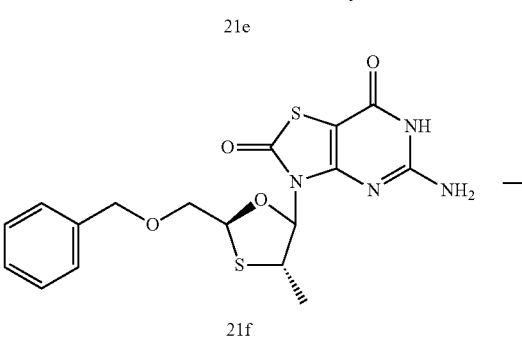

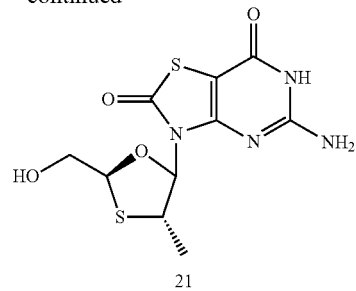

Preparation of (2R)-2-chloropropanoic acid

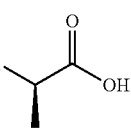

To a solution of D-alanine (35.6 g, 400 mmol) in aqueous HCl (6 N, 500 mL) was added NaNO$_2$ (44 g, 640 mmol) in small portions at 0° C. in 2.5 hours with vigorous stirring. After addition, the reaction was stirred at 0° C. for additional 4 hours. The solution was then extracted with ether (200 mL) three times, dried over anhydrous Na$_2$SO$_4$ and then concentrated in vacuo. The slightly yellow residue was fractionally distilled to afford (2R)-2-chloropropanoic acid (compound 21a) 21.4 g as a yellow oil.

Compound 21a: $^1$H NMR (400 MHz, DMSO-d6) δ ppm: 13.08-13.39 (m, 1H), 4.58 (d, J=6.90 Hz, 1H), 1.57 (d, J=6.78 Hz, 3H). MS obsd. (ESI$^-$)[(M−H)$^-$]: 107.

Preparation of cesium thioacetate (Compound 21b)

To a solution of thioacetic acid (10.7 g, 140 mmol) in methanol (100 mL) was added Cs$_2$CO$_3$ (22.9 g, 70 mmol) and the reaction mixture was stirred at room temperature for 7 hours. The mixture was concentrated in vacuo. The residue was triturated with dry acetone three times and again evaporated to give cesium thiolacetate (compound 21b) 33 g as a brown solid.

Preparation of (2S)-2-sulfanylpropanoic acid

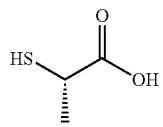

To a mixture of cesium thioacetate (42.8 g, 206 mmol) in DMF (250 mL) was added (2R)-2-chloropropanoic acid (21.4 g, 197 mmol) at room temperature. After being stirred at room temperature overnight, the reaction mixture was diluted with diethyl ether, washed with water and brine, dried over anhydrous Na$_2$SO$_4$ and then concentrated in vacuo. The residue was dissolved in 1N aqueous NH$_3$ (400 mL) and stirred at room temperature overnight. After being acidified to pH 4 to 5 with aqueous HCl (4N), the solution was then extracted with ether (200 mL) three times, dried over anhydrous Na₂SO₄ and concentrated. The residue was fractionally distilled to give (2S)-2-sulfanylpropanoic acid (compound 21c) 11.9 g as a light yellow oil.

Compound 21c: $^1$H NMR (400 MHz, DMSO-d6) δ ppm: 12.45-12.70 (m, 1H), 3.42-3.59 (m, 1H), 3.00-3.18 (m, 1H), 1.38 (d, J=7.03 Hz, 3H). MS obsd. (ESI⁻) [(M−H)⁻]: 105.

Preparation of (2S,4S)-2-(benzyloxymethyl)-4-methyl-1,3-oxathiolan-5-one and (2R,4S)-2-(benzyloxymethyl)-4-methyl-1,3-oxathiolan-5-one

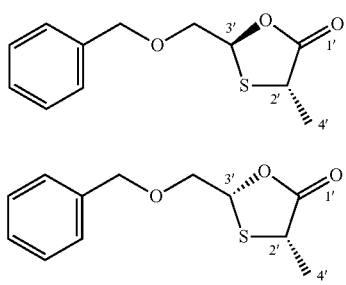

21d-S

21d-R

2-Benzyloxyacetaldehyde (4 mL, 28 mmol) was added dropwise to (2S)-2-sulfanylpropanoic acid (2 g, 19 mmol) at room temperature. The mixture was stirred at 50° C. overnight, diluted with ethyl acetate (150 mL), washed with saturated NaHCO₃ and brine, dried over anhydrous Na₂SO₄ and then concentrated. The residue was purified by column chromatography on silica gel (eluting with 1:20 to 1:5 ethyl acetate in petroleum ether) to afford (2S,4S)-2-(benzyloxymethyl)-4-methyl-1,3-oxathiolan-5-one (compound 21d-S) and (2R,4S)-2-(benzyloxymethyl)-4-methyl-1,3-oxathiolan-5-one (compound 21d-R) as a colorless oil. The configuration of compound 21d-S and compound 21-R were determined by NOESY.

Compound 21d-S: 0.88 g, $^1$H NMR (400 MHz, CD₃OD) δ ppm: 7.23-7.41 (m, 5H), 5.58-5.60 (m, 1H), 4.59 (s, 2H), 4.06-4.13 (m, 1H), 3.77-3.82 (m, 1H), 3.66-3.72 (m, 1H), 1.49 (d, J=7.03 Hz, 3H). MS obsd. (ESI⁺) [(M+H)⁺]: 239.

Compound 21d-R: 1.2 g, $^1$H NMR (400 MHz, CD₃OD) δ ppm: 7.25-7.42 (m, 5H), 5.65 (dd, J=5.27, 4.02 Hz, 1H), 4.62 (d, J=1.25 Hz, 2H), 4.11 (d, J=7.03 Hz, 1H), 3.73 (t, J=4.64 Hz, 2H), 1.52 (d, J=7.03 Hz, 3H). MS obsd. (ESI⁺) [(M+H)⁺]: 239.

For compound 21d-S, NOESY correlation of 3'-H and 4'-H was observed and NOESY correlation of 2'-H and 4'-H was not observed; and compound 21d-R, NOESY correlation of 3'-H and 4'-H was not observed and NOESY correlation of 2'-H and 4'-H was observed.

Preparation of [(2S,4S)-2-(benzyloxymethyl)-4-methyl-1,3-oxathiolan-5-yl] acetate

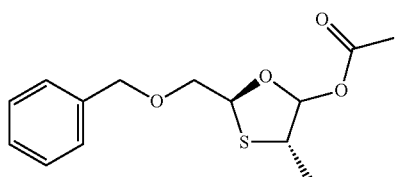

21e

To a solution of (2S,4S)-2-(benzyloxymethyl)-4-methyl-1,3-oxathiolan-5-one (0.4 g, 1.7 mmol) in anhydrous THF (5 mL) was added lithium tri-tert-butoxyaluminum hydride (1 M in THF, 2.5 mL, 2.5 mmol) dropwise at −78° C. The reaction mixture was allowed to warm to room temperature and stirred until the complete reduction of (2S,4S)-2-(benzyloxymethyl)-4-methyl-1,3-oxathiolan-5-one. To the reaction was added pyridine (0.68 mL, 8.4 mmol), acetic anhydride (0.8 mL, 8.4 mmol) and DMAP (0.62 g, 5.1 mmol). After being stirred at room temperature overnight, the reaction was quenched with saturated NH₄Cl solution (25 mL) and extracted with DCM (50 mL×3). The organic layer was combined, washed with brine, dried over anhydrous Na₂SO₄ and then concentrated in vacuo. The residue was purified by column chromatography on silica gel (eluting with 1:20 to 1:5 ethyl acetate in petroleum ether) to afford [(2S,4S)-2-(benzyloxymethyl)-4-methyl-1,3-oxathiolan-5-yl] acetate (compound 21e) 0.4 g as a colorless oil.

Compound 21e: $^1$H NMR (400 MHz, CD₃OD) δ ppm: 7.23-7.44 (m, 5H), 6.19-6.27 (m, 1H), 5.58-5.64 (m, 1H), 4.54-4.66 (m, 2H), 3.67-3.75 (m, 1H), 3.47-3.64 (m, 2H), 1.95 (s, 3H), 1.35 (d, J=7.03 Hz, 3H). MS obsd. (ESI⁺) [(M+NH₄)⁺]: 300.

Preparation of 5-amino-3-[(2S,4S)-2-(benzyloxymethyl)-4-methyl-1,3-oxathiolan-5-yl]-6H-thiazolo[4,5-d]pyrimidine-2,7-dione

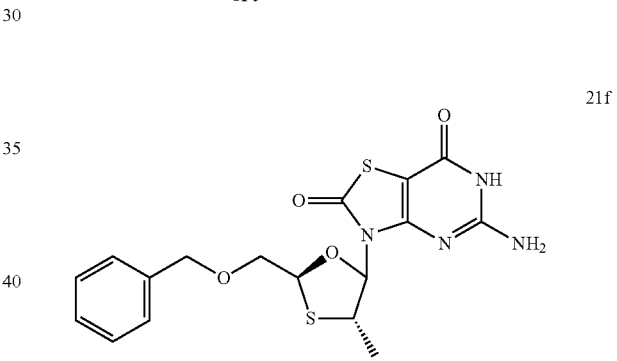

21f

To a suspension of 5-amino-7-hydroxy-3H-thiazolo[4,5-d]pyrimidin-2-one (244 mg, 1.3 mmol) in anhydrous ACN (20 mL) was added BSA (1.2 mL, 4.7 mmol). The mixture was heated at 60° C. until the solution is clear. The solvent was removed and the residue was re-dissolved in anhydrous DCM (20 mL). To the solution was added [(2S,4S)-2-(benzyloxymethyl)-4-methyl-1,3-oxathiolan-5-yl] acetate (300 mg, 1.1 mmol) and TMSI (0.41 mL, 2.9 mmol). The reaction mixture was stirred at room temperature overnight and then quenched with saturated NaHCO₃ solution. The mixture was extracted with DCM (50 mL) three times and washed with saturated NaHCO₃ solution and brine. The organic layer was dried over anhydrous Na₂SO₄ and then concentrated. The residue was purified by column chromatography on silica gel (eluting with 1:20 methanol in dichloromethane) to afford a mixture of 5-amino-3-[(2S,4S)-2-(benzyloxymethyl)-4-methyl-1,3-oxathiolan-5-yl]-6H-thiazolo[4,5-d]pyrimidine-2,7-dione (compound 21f) 140 mg as a colorless oil. MS obsd. (ESI⁺) [(M+H)⁺]: 407.

Preparation of 5-amino-3-[(2S,4S)-2-(hydroxymethyl)-4-methyl-1,3-oxathiolan-5-yl]-6H-thiazolo[4,5-d] pyrimidine-2,7-dione

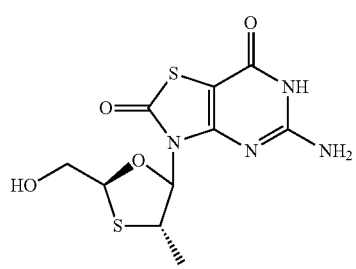

21

To a solution of the mixture of 5-amino-3-[(2S,4S,5R)-2-(benzyloxymethyl)-4-methyl-1,3-oxathiolan-5-yl]-6H-thiazolo[4,5-d]pyrimidine-2,7-dione and 5-amino-3-[(2S,4S,5S)-2-(benzyloxymethyl)-4-methyl-1,3-oxathiolan-5-yl]-6H-thiazolo[4,5-d]pyrimidine-2,7-dione (120 mg, 0.3 mmol) in anhydrous DCM (5 mL) was added a solution of boron trichloride (1.0 M in heptane, 1.2 mL, 1.2 mmol) at −78° C. The reaction mixture was stirred at −78° C. for 2 hours and then quenched with methanol (5 mL). The mixture was allowed to warm to room temperature and concentrated. The residue was purified and separated by preparative HPLC to afford Example 21-A (the diastereomer 1) and Example 21-B (the diastereomer 2) as white powders.

Example 21-A 6 mg, $^1$H NMR (400 MHz, CD$_3$OD) δ ppm: 5.84 (d, J=9.03 Hz, 1H), 5.26 (dd, J=5.27, 4.27 Hz, 1H), 4.57-4.64 (m, 1H), 3.71-3.82 (m, 2H), 1.30 (d, J=6.53 Hz, 3H). MS obsd. (ESI$^+$) [(M+H)$^+$]: 317.

Example 21-B 3.2 mg, $^1$H NMR (400 MHz, CD$_3$OD) δ ppm: 6.39 (d, J=6.27 Hz, 1H), 5.30-5.36 (m, 1H), 4.03 (dt, J=13.49, 6.81 Hz, 1H), 3.84-3.95 (m, 2H), 1.25-1.39 (m, 3H). MS obsd. (ESI$^+$) [(M+H)$^+$]: 317.

Example 22

5-Amino-3-[(4S)-2-[(1S)-1-hydroxypropyl]-4-methyl-1,3-oxathiolan-5-yl]-6H-thiazolo[4,5-d]pyrimidine-2,7-dione

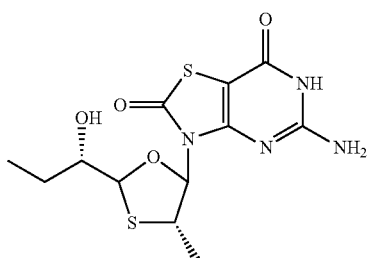

22

Preparation of [(1S)-1-formylpropyl] benzoate

22a

To a solution of butyl aldehyde (3.6 g, 50 mmol), [[diphenyl-[(2S)-pyrrolidin-2-yl]methoxy]-trimethyl-silane (1.6 g, 5.0 mmol) and hydroquinone (0.55 g, 5.0 mmol) in THF (60 mL) was added benzoyl peroxide (14.5 g, 60 mmol) dropwise at room temperature. After being stirred at room temperature for overnight, the reaction was diluted with EtOAc (100 mL), washed subsequently by 1N HCl (25 mL), water, saturated NaHCO$_3$ solution and brine, dried over anhydrous Na$_2$SO$_4$. The organic layer was then concentrated and the residue was purified by flash column chromatography on silica gel (eluting with 1:10 ethyl acetate in petroleum ether) to afford [(1S)-1-formylpropyl] benzoate (compound 22a) 3.8 g with an enantiomeric excess of 80%. The enantiomeric excess value of compound 22a was obtained by HPLC (Agilent 1260 HPLC) analysis using a chiral column (Diacel Chiralpak AZ-H (4.6 mm×250 mm, 5 μm)) after conversion to corresponding primary alcohol. The mobile phase of the chiral analysis was 20:80 ethanol in hexane. (For the synthesis, please refer to: *J. AM. CHEM. SOC.* 2009, 131, 3450-3451)

Compound 22a: $^1$H NMR (400 MHz, CDCl$_3$) δ ppm: 9.67 (d, J=0.8 Hz, 1H), 8.17-8.13 (m, 2H), 7.63 (s, 1H), 7.51 (d, J=7.8 Hz, 2H), 5.20 (ddd, J=7.8, 5.0, 0.8 Hz, 1H), 2.12-1.91 (m, 2H), 1.12 (t, J=7.4 Hz, 3H).

Preparation of [(1S)-1-[(4S)-4-methyl-5-oxo-1,3-oxathiolan-2-yl]propyl]benzoate

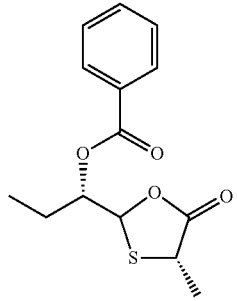

22b

The solution of [(1S)-1-formylpropyl]benzoate (1.15 g, 6.0 mmol), (2S)-2-sulfanylpropanoic acid (0.53 g, 5.0 mmol) and p-TsOH (5 mg) in toluene (50 mL) was heated for azeotropic dehydration at 130° C. for 2 hours, then concentrated and purified by flash column chromatography on silica gel (eluting with 1:20 ethyl acetate in petroleum ether) to afford [(1S)-1-[(4S)-4-methyl-5-oxo-1,3-oxathiolan-2-yl]propyl] benzoate (compound 22b) 1.3 g as a slightly yellow oil. [(M+NH$_4$)$^+$]: 298.

Preparation of [(1S)-1-[(4S)-5-acetoxy-4-methyl-1,3-oxathiolan-2-yl]propyl] benzoate

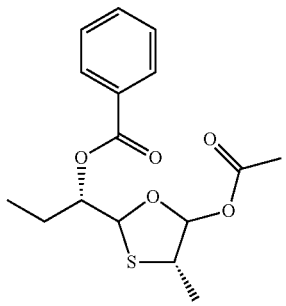

22c

To a solution of [(1S)-1-[(4S)-4-methyl-5-oxo-1,3-oxathiolan-2-yl]propyl] benzoate (0.62 g, 3.0 mmol) in THF (25 mL) was added lithium tri-tert-butoxyaluminum hydride at −5° C. (0.99 g, 3.9 mmol). The solution was then stirred at −5° C. for 2 hours and monitored by TLC until the complete reduction of [(1S)-1-[(4S)-4-methyl-5-oxo-1,3-oxathiolan-2-yl]propyl] benzoate. To the reaction was added acetic anhydride (1.0 g, 10 mmol) and TEA (2.0 g, 20 mmol). After being stirred at room temperature for 14 hours, the reaction mixture was quenched by saturated $NH_4Cl$ solution (25 mL), extracted by EtOAc (30 mL) three times, The combined organic layer was concentrated and the residue was purified by flash column chromatography on silica gel (eluting with 1:10 ethyl acetate in petroleum ether) to afford [(1S)-1-[(4S)-5-acetoxy-4-methyl-1,3-oxathiolan-2-yl]propyl] benzoate (compound 22c) 600 mg as a yellow oil. MS obsd. (ESI$^+$) [(M+NH$_4$)$^+$]: 342.

Preparation of [(1S)-1-[(4S)-5-(5-amino-2,7-dioxo-6H-thiazolo[4,5-d]pyrimidin-3-yl)-4-methyl-1,3-oxathiolan-2-yl]propyl] benzoate

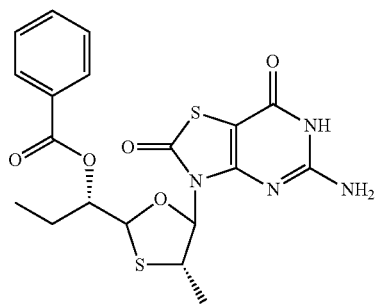

22d

To a suspension of 5-amino-3,6-dihydrothiazolo[4,5-d]pyrimidine-2,7-dione (460 mg, 2.5 mmol) in acetonitrile (30 mL) was added BSA (1.5 g, 7.5 mmol). The mixture was stirred at 70° C. for 0.5 hour under argon to form a clear solution. The solution was concentrated in vacuo to form a white solid which was re-dissolved in DCM (20 mL). To the above DCM solution was added [(1S)-1-[(4S)-5-acetoxy-4-methyl-1,3-oxathiolan-2-yl]propyl] benzoate (460 mg, 1.5 mmol) and TMSI (1.0 g, 5.0 mmol). After being stirred at 30° C. for 14 hours, the reaction mixture was concentrated and the residue was partitioned between ethyl acetate (25 mL) and saturated NaHCO$_3$ solution (15 mL). The organic layer was separated out and the aqueous phase was extracted with EtOAc (25 mL) two times. The organic layer was combined and washed with brine, dried over MgSO$_4$. The organic phase was concentrated and the residue was purified by flash column chromatography on silica gel (eluting with 1:10 methanol in dichloromethane) to afford [(1S)-1-[(4S)-5-(5-amino-2,7-dioxo-6H-thiazolo[4,5-d]pyrimidin-3-yl)-4-methyl-1,3-oxathiolan-2-yl]propyl] benzoate (compound 22d) 110 mg as a yellow solid. MS obsd. (ESI$^-$) [(M−H)]$^-$: 447.

Preparation of 5-amino-3-[(4S)-2-[(1S)-1-hydroxypropyl]-4-methyl-1,3-oxathiolan-5-yl]-6H-thiazolo[4,5-d]pyrimidine-2,7-dione

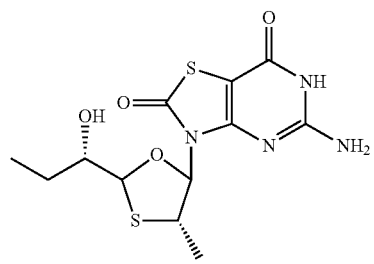

22

To a solution of [(1S)-1-[(4S)-5-(5-amino-2,7-dioxo-6H-thiazolo[4,5-d]pyrimidin-3-yl)-4-methyl-1,3-oxathiolan-2-yl]propyl] benzoate (150 mg, 0.33 mmol) in MeOH (20 mL) was added K$_2$CO$_3$ (276 mg, 2.0 mmol). After being stirred at room temperature overnight, the reaction solution was adjusted to pH 7.0 with HOAc (240 mg, 4.0 mmol), concentrated and purified and separated by preparative HPLC to afford Example 22-A (the diastereomer 1), Example 22-B (the diastereomer 2), Example 22-C (the diastereomer 3) and Example 22-D (the diastereomer 4) as white solids.

Example 22-A 2.4 mg, $^1$H NMR (400 MHz, CD$_3$OD) δ ppm: 5.82 (d, J=9.0 Hz, 1H), 5.16 (d, J=4.9 Hz, 1H), 4.50-4.56 (m, 1H), 3.58-3.64 (m, 1H), 1.65 (ddd, J=13.9, 7.5, 3.6 Hz, 1H), 1.46-1.53 (m, 1H), 1.29 (d, J=6.5 Hz, 3H), 1.02 (t, J=7.5 Hz, 3H). MS obsd. (ESI$^+$) [(M+H)$^+$]: 345.

Example 22-B 5.8 mg, $^1$H NMR (400 MHz, CD$_3$OD) δ ppm: 6.64 (d, J=6.4 Hz, 1H), 5.75 (d, J=4.9 Hz, 1H), 4.18-4.10 (m, 1H), 3.50 (s, 1H), 1.67-1.49 (m, 2H), 1.29 (d, J=6.9 Hz, 3H), 1.03 (t, J=7.4 Hz, 3H). MS obsd. (ESI$^+$) [(M+H)$^+$]: 345.

Example 22-C 1.9 mg, $^1$H NMR (400 MHz, CD$_3$OD) δ ppm: 5.98 (d, J=7.9 Hz, 1H), 5.66 (d, J=5.6 Hz, 1H), 4.59-4.51 (m, 1H), 3.70-3.63 (m, 1H), 1.72-1.65 (m, 1H), 1.46-1.40 (m, 1H), 1.36 (d, J=6.7 Hz, 3H), 1.01 (t, J=7.5 Hz, 3H). MS obsd. (ESI$^+$) [(M+H)$^+$]: 345.

Example 22-D 2.5 mg, $^1$H NMR (400 MHz, CD$_3$OD) δ ppm: 6.40 (d, J=6.5 Hz, 1H), 5.25 (d, J=4.1 Hz, 1H), 4.04-3.99 (m, 1H), 3.97-3.92 (m, 1H), 1.68-1.61 (m, 1H), 1.52-1.46 (m, 1H), 1.30 (d, J=7.0 Hz, 3H), 1.03 (t, J=7.5 Hz, 3H). MS obsd. (ESI$^+$) [(M+H)$^+$]: 345.

Example 23

5-Amino-3-[(2S,4S)-2-[cyclopropyl(hydroxy)methyl]-4-methyl-1,3-oxathiolan-5-yl]-6H-thiazolo[4,5-d]pyrimidine-2,7-dione

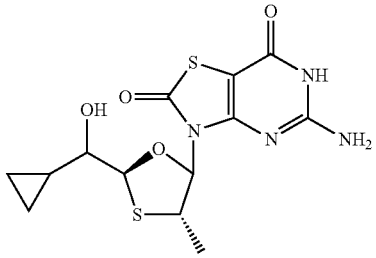

23

Preparation of 2-cyclopropylacetaldehyde

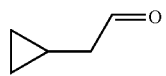

23a

To a solution of oxalyl chloride (7.4 mL, 87 mmol) in DCM (100 mL) was added DMSO (12.4 mL, 174 mmol) dropwise at −78° C. and the solution was stirred at −78° C. for 15 minutes, then to the reaction solution was added cyclopropyl ethylalcohol (5 g, 58 mmol, dissolved in DCM 10 mL). After being stirred at −78° C. for 1 hour, to the reaction solution was added TEA (40.4 ml, 290 mmol). The reaction solution was allowed to warm to room temperature and stirred for another 30 minutes. The reaction was quenched with water (50 ml) and extracted with DCM (50 mL) three times. The organic phase was combined, washed with saturated NH$_4$Cl solution, water and brine, and dried over anhydrous Na$_2$SO$_4$. The organic layer was concentrated and the residue was fractionally distilled to give 2-cyclopropylacetaldehyde (compound 23a) 1.3 g as a colorless oil.

Compound 23a: $^1$H NMR (400 MHz, DMSO-d6) δ ppm: 9.64-9.76 (m, 1H), 2.28-2.37 (m, 2H), 0.89-0.98 (m, 1H), 0.51 (dd, J=8.16, 1.63 Hz, 2H), 0.14 (dd, J=4.83, 1.44 Hz, 2H).

Preparation of 2-cyclopropyl-2-hydroxy-acetaldehyde

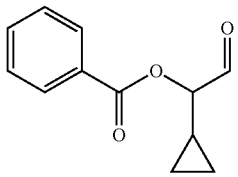

23b

A mixture of 2-cyclopropylacetaldehyde (1.3 g, 15.5 mmol), (S)-(−)-α,α-diphenyl-2-pyrrolidinemethanol trimethylsilyl ether (0.5 g, 1.5 mmol) and hydroquinone (0.17 g, 1.6 mmol) in THF (100 mL) was stirred at 0° C. To the reaction solution was added benzyl peroxide (4.2 g, 17.1 mmol). After being stirred at 0° C. to 25° C. for 4 hours, the reaction mixture was poured into 1N HCl and extracted with ethyl acetate (50 mL) three times. The organic layer was combined and washed with saturated NaHCO$_3$ solution and brine. The organic layer was dried over anhydrous Na$_2$SO$_4$ and then concentrated. The residue was purified by column chromatography on silica gel (eluting with 1:20 to 1:5 ethyl acetate in petroleum ether) to afford 2-cyclopropyl-2-hydroxy-acetaldehyde (compound 23b) 1.6 g as a brown oil.

Compound 23b: $^1$H NMR (400 MHz, DMSO-d6) δ ppm: 9.68 (s, 1H), 7.99-8.08 (m, 2H), 7.72 (s, 1H), 7.50-7.63 (m, 2H), 4.75 (d, J=9.16 Hz, 1H), 1.22-1.33 (m, 1H), 0.62-0.80 (m, 3H), 0.48-0.57 (m, 1H). MS obsd. (ESI$^+$)[(M+H)$^+$]: 205.

Preparation of [cyclopropyl-[(2S,4S)-4-methyl-5-oxo-1,3-oxathiolan-2-yl]methyl] benzoate and [cyclopropyl-[(2R,4S)-4-methyl-5-oxo-1,3-oxathiolan-2-yl]methyl] benzoate

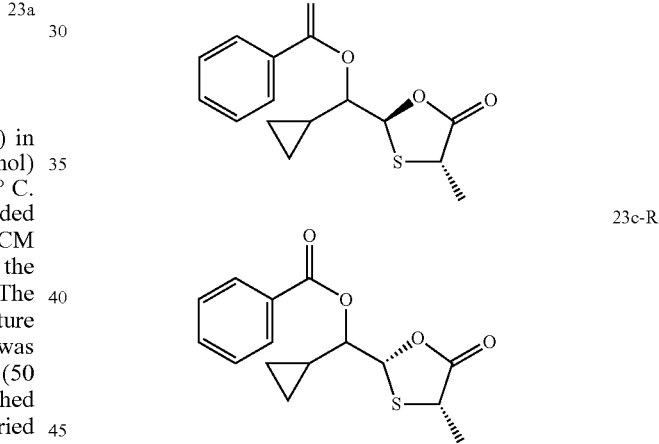

The mixture of 2-cyclopropyl-2-hydroxy-acetaldehyde (1.6 g, 7.8 mmol) and (2S)-2-sulfanylpropanoic acid (0.83 g, 7.8 mmol) was stirred at 50° C. overnight. After the reaction was completed, the reaction solution was diluted with ethyl acetate (50 mL), washed with saturated NaHCO$_3$ solution and brine, dried over anhydrous Na$_2$SO$_4$ and concentrated. The residue was purified by column chromatography on silica gel (eluting with 1:20 to 1:5 ethyl acetate in petroleum ether) to afford [cyclopropyl-[(2S,4S)-4-methyl-5-oxo-1,3-oxathiolan-2-yl]methyl] benzoate (compound 23c-S) and [cyclopropyl-[(2S,4S)-4-methyl-5-oxo-1,3-oxathiolan-2-yl]methyl] benzoate (compound 23c-R). The configuration of compound 23c-S and 23c-R were determined in analogy to compound 21d-S and 21d-R.

Compound 23c-S: 0.6 g, $^1$H NMR (400 MHz, CDCl$_3$) δ ppm: 8.03-8.11 (m, 2H), 7.58-7.67 (m, 1H), 7.43-7.55 (m, 2H), 5.68-5.74 (m, 1H), 4.72 (dd, J=9.29, 3.26 Hz, 1H), 3.94 (q, J=7.07 Hz, 1H), 1.54-1.59 (m, 3H), 1.35-1.42 (m, 1H), 0.70-0.79 (m, 1H), 0.59-0.70 (m, 2H), 0.47-0.59 (m, 1H). MS obsd. (ESI$^+$) [(M+H)$^+$]: 293.

Compound 23c-R: 0.9 g, ¹H NMR (400 MHz, CDCl₃) δ ppm: 8.01-8.14 (m, 2H), 7.57-7.65 (m, 1H), 7.43-7.52 (m, 2H), 5.67-5.75 (m, 1H), 4.90 (dd, J=8.53, 4.39 Hz, 1H), 4.02 (q, J=7.03 Hz, 1H), 1.63 (d, J=6.90 Hz, 3H), 1.13-1.24 (m, 1H), 0.71-0.81 (m, 1H), 0.52-0.70 (m, 3H). MS obsd. (ESI⁺) [(M+H)⁺]: 293.

Preparation of [[(2S,4S)-5-acetoxy-4-methyl-1,3-oxathiolan-2-yl]-cyclopropyl-methyl] benzoate

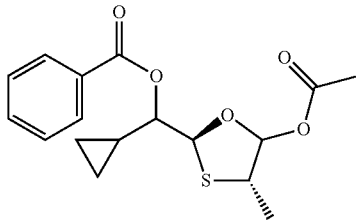

23d

To a solution of [cyclopropyl-[(2S,4S)-4-methyl-5-oxo-1,3-oxathiolan-2-yl]methyl] benzoate (0.6 g, 2.1 mmol) in dry THF (15 mL) was added lithium tri-tert-butoxyaluminum hydride (1.0 M in THF, 3.1 mL, 3.1 mmol) dropwise at −78° C. under nitrogen. The reaction mixture was stirred at 0° C. for 2 hours. Then to the reaction was added pyridine (0.83 mL, 10.3 mmol), acetic anhydride (0.97 mL, 10.3 mmol) and DMAP (0.75 g, 6.2 mmol). The reaction mixture was stirred at room temperature overnight and quenched with saturated NH₄Cl solution. The solution was extracted with DCM (50 mL) three times. The organic layer was combined and washed with brine, dried over anhydrous Na₂SO₄ and then concentrated. The residue was purified by column chromatography on silica gel (eluting with 1:20 to 1:5 ethyl acetate in petroleum ether) to afford [[(2S,4S)-5-acetoxy-4-methyl-1,3-oxathiolan-2-yl]-cyclopropyl-methyl] benzoate (compound 23d) 0.5 g as a colorless oil. MS obsd. (ESI⁺) [(M+NH₄)⁺]: 354.

Preparation of [[(2S,4S)-5-(5-amino-2,7-dioxo-6H-thiazolo[4,5-d]pyrimidin-3-yl)-4-methyl-1,3-oxathiolan-2-yl]-cyclopropyl-methyl]benzoate

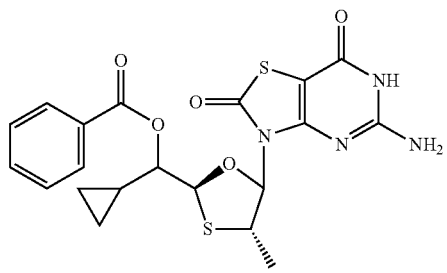

23e

To a solution of 5-amino-7-hydroxy-3H-thiazolo[4,5-d]pyrimidin-2-one (340 mg, 1.86 mmol) in CH₃CN (10 mL) was added BSA (1.6 mL, 6.5 mmol). The mixture was heated at 60° C. until a clear solution was formed. The solvent was removed in vacuo. The residue was re-dissolved in DCM (20 mL). To the solution was added [(S)-(2S,4S)-5-acetoxy-4-methyl-1,3-oxathiolan-2-yl]-cyclopropyl-methyl] benzoate (500 mg, 1.5 mmol) and trimethylsilyl iodide (0.57 mL, 4.1 mmol). The reaction mixture was stirred at room temperature overnight, quenched with saturated NaHCO₃ solution. The solution was extracted with DCM (50 mL) three times. The organic layer was combined and washed with saturated NaHCO₃ solution and brine. The organic layer was dried over anhydrous Na₂SO₄ and then concentrated. The residue was purified by column chromatography on silica gel (eluting with 1:3 methanol in dichloromethane) to afford [[(2S,4S)-5-(5-amino-2,7-dioxo-6H-thiazolo[4,5-d]pyrimidin-3-yl)-4-methyl-1,3-oxathiolan-2-yl]-cyclopropyl-methyl]benzoate (compound 23e) 0.15 g as a colorless oil (4 isomers, ratio 8:12:2:3). MS obsd. (ESI⁺) [(M+H)⁺]: 461.

Preparation of 5-amino-3-[(2S,4S)-2-[cyclopropyl(hydroxy)methyl]-4-methyl-1,3-oxathiolan-5-yl]-6H-thiazolo[4,5-d]pyrimidine-2,7-dione

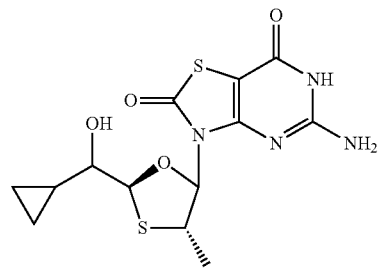

23

To a solution of [[(2S,4S)-5-(5-amino-2,7-dioxo-6H-thiazolo[4,5-d]pyrimidin-3-yl)-4-methyl-1,3-oxathiolan-2-yl]-cyclopropyl-methyl]benzoate (150 mg, 0.33 mmol) in methanol (10 mL) was added K₂CO₃ (180 mg, 1.3 mmol). After being stirred at room temperature for 5 hours, the reaction mixture was neutralized to pH 7 with HOAc (0.16 g, 2.6 mmol). The reaction solution was concentrated and the residue was purified and separated by preparative HPLC to afford Example 23-A (the diastereomer 1), Example 23-B (the diastereomer 2), Example 23-C (the diastereomer 3) and Example 23-D (the diastereomer 4) as white powders.

Example 23-A 6 mg, ¹H NMR (400 MHz, CD₃OD) δ ppm: 5.83 (d, J=8.78 Hz, 1H), 5.26 (d, J=5.02 Hz, 1H), 4.49-4.60 (m, 1H), 3.13 (dd, J=7.84, 5.08 Hz, 1H), 1.26-1.38 (m, 3H), 0.91-1.01 (m, 1H), 0.46-0.57 (m, 2H), 0.33-0.46 (m, 2H). MS obsd. (ESI⁺) [(M+H)⁺]: 357.

Example 23-B 1 mg ¹H NMR (400 MHz, CD₃OD) δ ppm: 5.83-5.88 (m, 1H), 5.28-5.32 (m, 1H), 4.41-4.47 (m, 1H), 3.21-3.24 (m, 1H), 1.24-1.35 (m, 3H), 0.90-0.95 (m, 1H), 0.47-0.58 (m, 2H), 0.39-0.47 (m, 1H), 0.31-0.36 (m, 1H). MS obsd. (ESI⁺) [(M+H)⁺]: 357.

Example 23-C 12 mg ¹H NMR (400 MHz, CD₃OD) δ ppm: 6.66 (d, J=6.27 Hz, 1H), 5.85 (d, J=4.89 Hz, 1H), 4.16 (q, J=6.74 Hz, 1H), 2.96 (dd, J=8.53, 4.89 Hz, 1H), 1.30 (d, J=6.90 Hz, 3H), 1.01-1.09 (m, 1H), 0.49-0.60 (m, 2H), 0.35-0.45 (m, 2H). MS obsd. (ESI⁺) [(M+H)⁺]: 357.

Example 23-D 4 mg ¹H NMR (400 MHz, CD₃OD) δ ppm: 6.67 (d, J=6.27 Hz, 1H), 5.85 (d, J=3.64 Hz, 1H), 4.13-4.21 (m, 1H), 3.15-3.19 (m, 1H), 1.28 (d, J=6.90 Hz, 3H), 0.92 (dt, J=8.13, 4.91 Hz, 1H), 0.49-0.58 (m, 2H), 0.33-0.42 (m, 2H). MS obsd. (ESI⁺) [(M+H)⁺]: 357.

Example 24

5-Amino-3-[(4S)-2-(1-hydroxybut-2-ynyl)-4-methyl-1,3-oxathiolan-5-yl]-6H-thiazolo[4,5-d]pyrimidine-2,7-dione

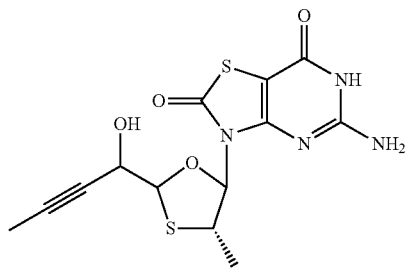

24

Synthetic Scheme of Example 29

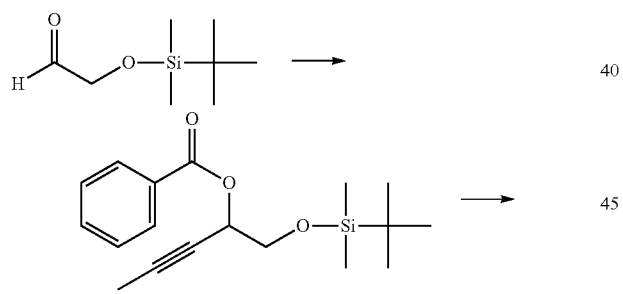

24a

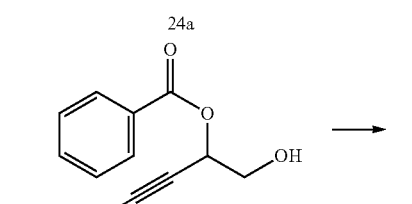

24b

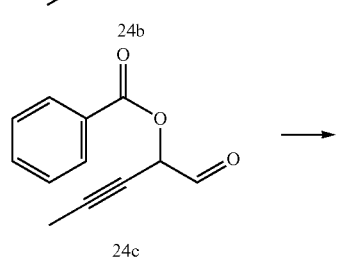

24c

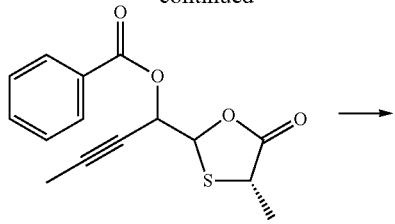

24d
(24d-1 and 24d-2 were used into next step)

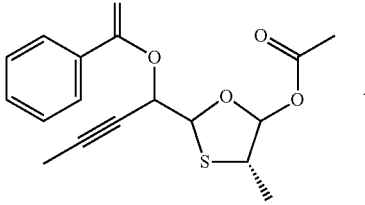

24e

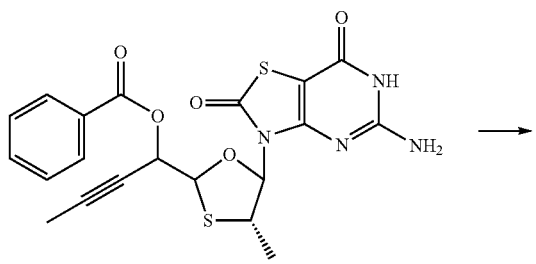

24f

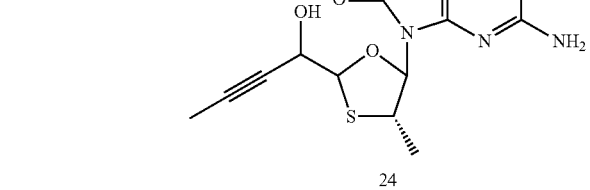

24

Preparation of 1-[[tert-butyl(dimethyl)silyl]oxymethyl]but-2-ynyl benzoate

24a

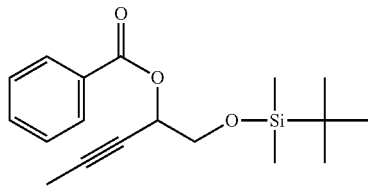

To a solution of 2-[tert-butyl(dimethyl)silyl]oxyacetaldehyde (3.48 g, 20 mmol) in anhydrous THF (20 mL) was added propynyl magnesium bromide (0.5 M in THF, 48 mL, 20 mmol) dropwise at 0° C. under nitrogen. The reaction mixture was stirred at 0° C. for 2 hours. Then to the reaction was added TEA (4.04 g, 40 mmol) and benzoic anhydride (6.0 g, 25 mmol). The reaction mixture was stirred at room temperature overnight and quenched with saturated NH₄Cl solution (50 mL). The solution was extracted with EtOAc (50 mL) three times. The organic layer was combined and washed with brine, dried over anhydrous Na₂SO₄ and then concentrated. The residue was purified by flash chromatography on silica gel (eluting with 1:20 ethyl acetate in petroleum ether) to afford 1-[[tert-butyl(dimethyl)silyl]oxymethyl]but-2-ynyl benzoate (compound 24a) 5.05 g as a colorless oil.

Compound 24a: $^1$H NMR (400 MHz, CDCl₃) δ ppm: 8.06-8.15 (m, 2H), 7.56-7.62 (m, 1H), 7.43-7.52 (m, 2H), 5.64-5.73 (m, 1H), 3.89-3.98 (m, 2H), 1.87 (d, J=2.13 Hz, 3H), 0.88 (s, 9H), 0.09 (d, J=12.30 Hz, 6H).

Preparation of 1-(hydroxymethyl)but-2-ynyl benzoate

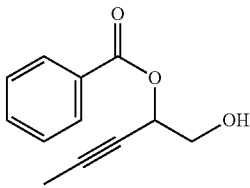

24b

To a solution of 1-[[tert-butyl(dimethyl)silyl]oxymethyl]but-2-ynyl benzoate (954 mg, 3 mmol) in the mixture of THF (15 mL) and MeOH (5 mL) was added hydrochloride acid (1 N, 3 mL, 3 mmol). The solution was stirred at room temperature for 4 hours and to the solution was added KHCO₃ (378 mg, 3 mmol). The reaction was concentrated in vacuo and the residue was partitioned between EtOAc and H₂O. The organic layer was separated and the aqueous phase was extracted with EtOAc (30 mL) twice. The organic layer was combined and washed with brine, dried over anhydrous Na₂SO₄ and then concentrated to yield 1-(hydroxymethyl)but-2-ynyl benzoate (compound 24b) 670 mg as a yellow solid, which was used directly in the next step.

Compound 24b: $^1$H NMR (400 MHz, CDCl₃) δ ppm: 8.05-8.19 (m, 2H), 7.59 (m, 1H), 7.43-7.52 (m, 2H), 5.63-5.73 (m, 1H), 3.93 (d, J=5.14 Hz, 2H), 1.89 (d, J=2.13 Hz, 3H).

Preparation of 1-formylbut-2-ynyl benzoate

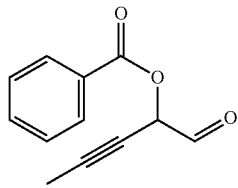

24c

To a solution of 1-(hydroxymethyl)but-2-ynyl benzoate (224 mg, 1.1 mmol) in DCM (15 mL) was added Dess-Martin periodinane (466 mg, 1.1 mmol). The mixture was stirred at room temperature for 1 hour and the solution was filtered through silica pad. The filtrate was concentrated and purified by flash chromatography on silica gel (eluting with 1:20 ethyl acetate in petroleum ether) to afford 1-formylbut-2-ynyl benzoate (compound 24c) 202 mg as a yellow oil.

Compound 24c: $^1$H NMR (400 MHz, CDCl₃) δ ppm: 9.50-9.59 (m, 1H), 8.13-8.17 (m, 2H), 7.61-7.67 (m, 1H), 7.47-7.53 (m, 2H), 5.83-5.96 (m, 1H), 1.97 (d, J=2.51 Hz, 3H).

Preparation of 1-[(4S)-4-methyl-5-oxo-1,3-oxathiolan-2-yl]but-2-ynyl benzoate

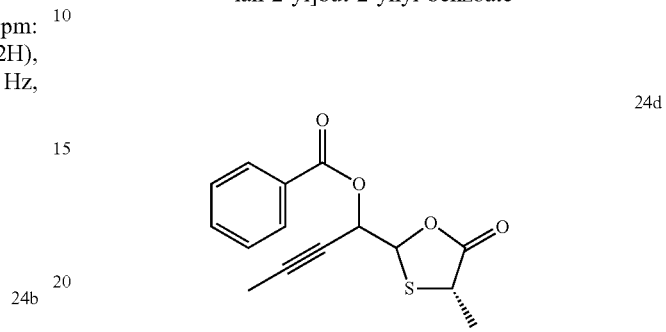

24d

The solution of 1-formylbut-2-ynyl benzoate (2.02 g, 10.0 mmol), (2S)-2-sulfanylpropanoic acid (1.06 g, 10 mmol) and p-TsOH (5 mg) in toluene (50 mL) was heated for azeotropic dehydration at 130° C. for 2 hours, the reaction mixture was then concentrated and purified by flash column chromatography on silica gel (eluting with 1:20 ethyl acetate in petroleum ether) to afford 1-[(4S)-4-methyl-5-oxo-1,3-oxathiolan-2-yl]but-2-ynyl benzoate compound 24d-1 (diastereomer 1) 60 mg, compound 24d-2 (diastereomer 2) 200 mg, compound 24d-3 (diastereomer 3) 200 mg, compound 24d-4 (diastereomer 4) 50 mg.

Compound 24d-1: $^1$H NMR (400 MHz, CDCl₃) δ ppm: 8.08 (dd, J=1.13, 8.41 Hz, 2H), 7.62 (m, 1H), 7.48-7.53 (m, 2H), 5.81-5.89 (m, 1H), 5.58-5.67 (m, 1H), 4.08 (d, J=7.28 Hz, 1H), 1.91 (d, J=2.01 Hz, 3H), 1.62 (d, J=7.28 Hz, 3H). MS obsd. (ESI⁺) [(M+H)⁺]: 291.

Compound 24d-2: $^1$H NMR (400 MHz, CDCl₃) δ ppm: 8.10-8.17 (m, 2H), 7.62-7.69 (m, 1H), 7.50-7.53 (m, 2H), 5.79-5.86 (m, 1H), 5.68 (d, J=6.53 Hz, 1H), 4.01-4.10 (m, 1H), 1.91 (d, J=2.26 Hz, 3H), 1.65 (d, J=7.03 Hz, 3H). MS obsd. (ESI⁺) [(M+H)⁺]: 291.

Compound 24d-3: $^1$H NMR (400 MHz, CDCl₃) δ ppm: 8.15 (dd, J=1.13, 8.16 Hz, 2H), 7.62-7.67 (m, 1H), 7.49-7.53 (m, 3H), 5.79-5.87 (m, 1H), 5.70 (s, 1H), 4.02-4.13 (m, 1H), 1.91 (d, J=2.26 Hz, 3H), 1.70 (d, J=7.03 Hz, 3H). MS obsd. (ESI⁺) [(M+H)⁺]: 291.

Compound 24d-4: MS obsd. (ESI⁺) [(M+H)⁺]: 291.

Preparation of 1-[(4S)-5-acetoxy-4-methyl-1,3-oxathiolan-2-yl]but-2-ynyl benzoate

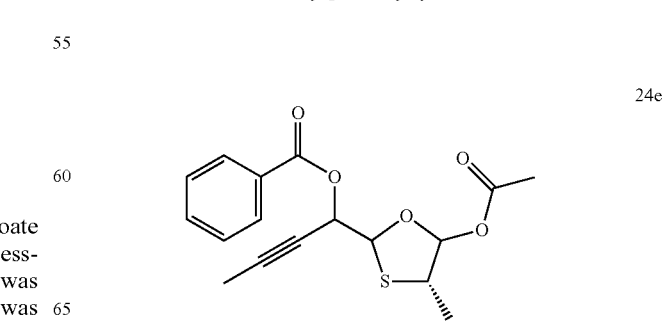

24e

To a solution of 1-[(4S)-4-methyl-5-oxo-1,3-oxathiolan-2-yl]but-2-ynyl benzoate (300 mg, 1.0 mmol, mixture of compound 24d-1 and compound 24d-2) in dry THF (15 mL) was added lithium tri-tert-butoxyaluminum hydride (300 mg, 1.2 mmol) at −78° C. The reaction mixture was stirred at 0° C. for 2 hours. Then to the reaction was added TEA (0.8 mL, 6.7 mmol), acetic anhydride (0.5 mL, 5.2 mmol). The reaction mixture was stirred at room temperature overnight and quenched with saturated NH$_4$Cl solution. The mixture was extracted with EtOAc (50 mL) three times. The organic layer was combined and washed with brine, dried over anhydrous Na$_2$SO$_4$ and then concentrated. The residue was purified by column chromatography on silica gel (eluting with 1:20 to 1:5 ethyl acetate in petroleum ether) to afford 1-[(4S)-5-acetoxy-4-methyl-1,3-oxathiolan-2-yl]but-2-ynyl benzoate (compound 24e) 300 mg as a colorless oil. MS obsd. (ESI$^+$) [(M+NH$_4$)$^+$]: 352.

Preparation of 1-[(4S)-5-(5-amino-2,7-dioxo-6H-thiazolo[4,5-d]pyrimidin-3-yl)-4-methyl-1,3-oxathiolan-2-yl]but-2-ynyl benzoate

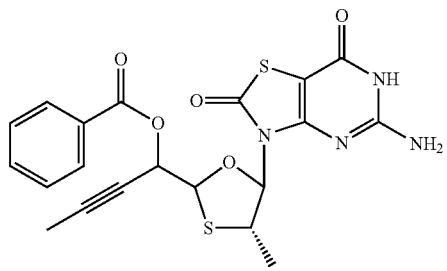

24f

To a solution of 5-amino-7-hydroxy-3H-thiazolo[4,5-d]pyrimidin-2-one (368 mg, 2 mmol) in CH$_3$CN (30 mL) was added BSA (1.2 g, 6 mmol). The mixture was heated at 70° C. to form a clear solution. The solvent was removed in vacuo. The residue was dissolved in DCM (15 mL). 1-[(4S)-5-acetoxy-4-methyl-1,3-oxathiolan-2-yl]but-2-ynyl benzoate (300 mg, 0.9 mmol) and trimethylsilyl iodide (800 mg, 4 mmol) were added to the above solution. The reaction mixture was stirred at 40° C. overnight and then quenched with saturated NaHCO$_3$ solution. The solution was extracted with DCM (50 mL) three times. The combined organic layer was washed with saturated NaHCO$_3$ solution and brine dried over anhydrous Na$_2$SO$_4$ and then concentrated. The residue was purified by column chromatography on silica gel (eluting with 1:20 methanol in dichloromethane) to afford 1-[(4S)-5-(5-amino-2,7-dioxo-6H-thiazolo[4,5-d]pyrimidin-3-yl)-4-methyl-1,3-oxathiolan-2-yl]but-2-ynyl benzoate (compound 24f) 54 mg as a colorless oil. MS obsd. (ESI$^+$) [(M−H)$^+$]: 457.

Preparation of 5-amino-3-[(4S)-2-(1-hydroxybut-2-ynyl)-4-methyl-1,3-oxathiolan-5-yl]-6H-thiazolo[4,5-d]pyrimidine-2,7-dione

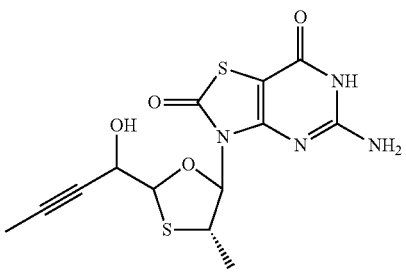

24

To a solution of 1-[(4S)-5-(5-amino-2,7-dioxo-6H-thiazolo[4,5-d]pyrimidin-3-yl)-4-methyl-1,3-oxathiolan-2-yl]but-2-ynyl benzoate (54 mg, 0.12 mmol) in methanol (10 mL) was added K$_2$CO$_3$ (138 mg, 1.0 mmol). The reaction was stirred at room temperature for 2 hours and the reaction solution was neutralized to pH 7 with HOAc (120 mg, 2.0 mmol). The reaction solution was concentrated and the residue was purified and separated by preparative HPLC to afford Example 24-A (the diastereomer 1), Example 24-B (the diastereomer 2), Example 24-C (the diastereomer 3) and Example 24-D (the diastereomer 4) as white powders.

Example 24-A 1.4 mg, $^1$H NMR (400 MHz, CD$_3$OD) δ ppm: 5.87 (d, J=9.03 Hz, 1H), 5.12 (d, J=6.78 Hz, 1H), 4.57-4.65 (m, 1H), 4.46-4.52 (m, 1H), 1.84 (d, J=2.13 Hz, 3H), 1.29 (d, J=6.53 Hz, 3H). MS obsd. (ESI$^+$) [(M+H)$^+$]: 355.

Example 24-B 1.6 mg, $^1$H NMR (400 MHz, CD$_3$OD) δ ppm: 6.69 (d, J=6.02 Hz, 1H), 5.77 (d, J=3.51 Hz, 1H), 4.40-4.46 (m, 1H), 4.22 (s, 1H), 1.86 (d, J=2.26 Hz, 2H), 1.25 (d, J=7.03 Hz, 3H). MS obsd. (ESI$^+$) [(M+H)$^+$]: 355.

Example 24-C 1.3 mg, $^1$H NMR (400 MHz, CD$_3$OD) δ ppm: 6.67 (d, J=6.27 Hz, 1H), 5.73 (d, J=6.02 Hz, 1H), 4.34-4.39 (m, 1H), 4.16-4.24 (m, 1H), 1.86 (d, J=2.26 Hz, 3H), 1.27 (d, J=6.78 Hz, 3H). MS obsd. (ESI$^+$) [(M+H)$^+$]: 355.

Example 24-D 1.2 mg, $^1$H NMR (400 MHz, CD$_3$OD) δ ppm: 5.85 (d, J=9.03 Hz, 1H), 5.22 (d, J=4.27 Hz, 1H), 4.56 (dd, J=2.07, 4.33 Hz, 1H), 4.49 (dd, J=6.46, 9.10 Hz, 1H), 1.85 (d, J=2.26 Hz, 3H), 1.28 (d, J=6.53 Hz, 3H). MS obsd. (ESI$^+$) [(M+H)$^+$]: 355.

Example 25

3-[4-Allyl-2-(hydroxymethyl)-1,3-oxathiolan-5-yl]-5-amino-6H-thiazolo[4,5-d]pyrimidine-2,7-dione

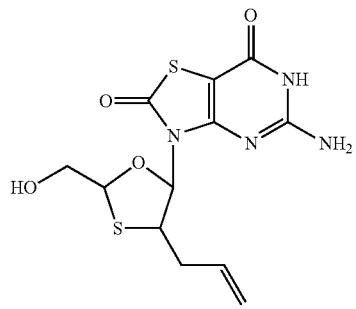

Synthetic Scheme of Example 25

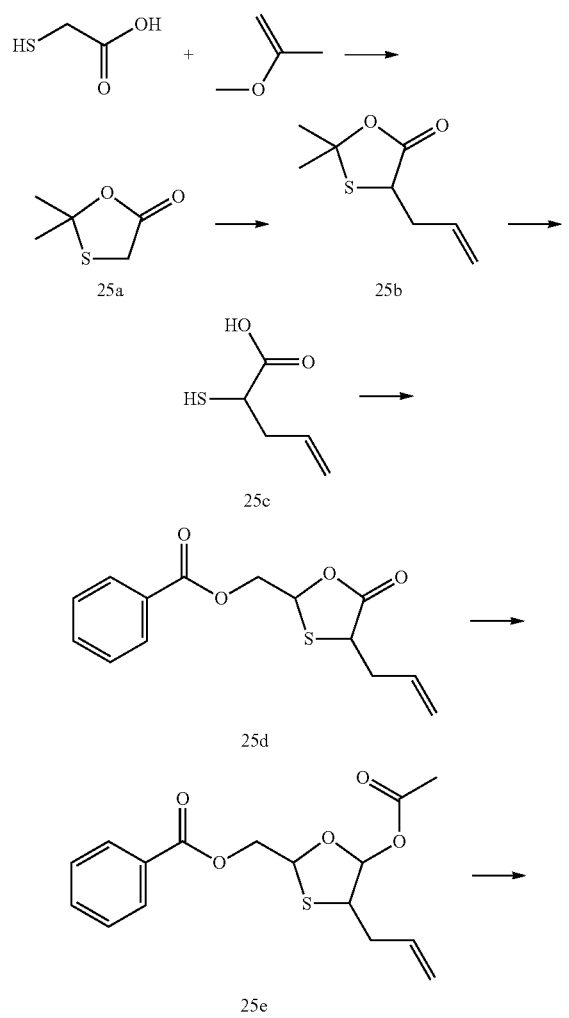

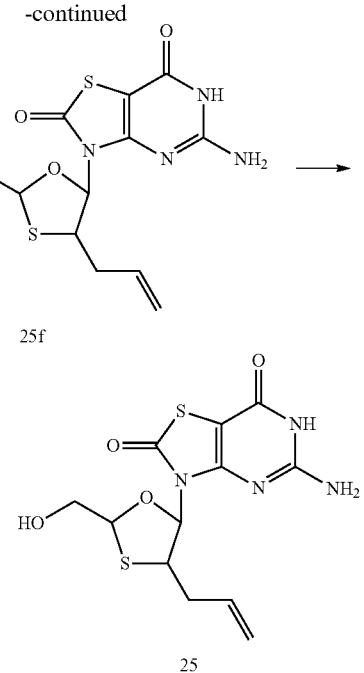

Preparation of 2,2-dimethyl-1,3-oxathiolan-5-one

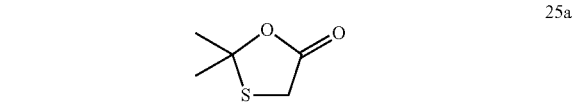

25a

To the thioglycolic acid (12 mL, 172.8 mmol) was added 2-methoxypropene (64.8 mL, 691.2 mmol) dropwise at 0° C. with vigorous stirring. After the addition was complete, the mixture was stirred at 70° C. overnight. The mixture was allowed to cool to room temperature. Then the reaction mixture was diluted with ether, washed with saturated NaHCO$_3$ solution and brine, dried over anhydrous Na$_2$SO$_4$ and then concentrated in vacuo. The residue was purified by flash column chromatography on silica gel (eluting with 1:10 to 1:5 ethyl acetate in petroleum ether) to afford a yellow oil. The yellow oil was fractionally distilled to give 2,2-dimethyl-1,3-oxathiolan-5-one (compound 25a) 5.8 g as a slightly yellow oil.

Compound 25a: $^1$H NMR (400 MHz, CDCl$_3$) δ ppm: 3.84 (s, 2H), 1.73-1.83 (m, 6H).

Preparation of 4-allyl-2,2-dimethyl-1,3-oxathiolan-5-one

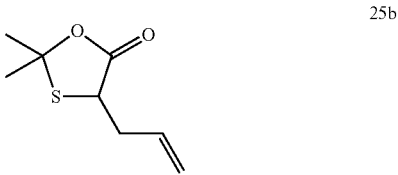

25b

To a solution of 2,2-dimethyl-1,3-oxathiolan-5-one (1.6 g, 11 mmol) in THF (20 mL) was dropwise added LiHMDS (1.3 M in THF, 10 mL, 13 mmol) at −78° C. and the reaction solution was maintained at this temperature for 1 hour after addition. To the solution was added allyl bromide (1.2 mL, 13.2 mmol). After being stirred at −78° C. for 2 hours, the reaction solution was quenched with saturated NH$_4$Cl solution. The mixture was extracted with ethyl acetate (50 mL) three times. The organic layer was combined, washed with brine, dried over anhydrous Na$_2$SO$_4$ and then concentrated. The residue was purified by flash column chromatography on silica gel (eluting with 1:20 to 1:5 ethyl acetate in petroleum ether) to afford 4-allyl-2,2-dimethyl-1,3-oxathiolan-5-one (compound 25b) 0.8 g as a colorless oil.

Compound 25b: $^1$H NMR (400 MHz, CDCl$_3$) δ ppm: 5.76-5.86 (m, 1H), 5.09-5.26 (m, 2H), 4.17-4.25 (m, 1H), 2.97 (dddt, J=14.68, 5.99, 4.36, 1.41, 1.41 Hz, 1H), 2.50-2.61 (m, 1H), 1.73-1.82 (m, 6H). MS obsd. (ESI$^+$) [(M+H)$^+$]: 173.

Preparation of 2-sulfanylpent-4-enoic acid

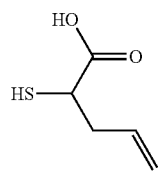

25c

To a solution of 4-allyl-2,2-dimethyl-1,3-oxathiolan-5-one (0.8 g, 4.6 mmol) in THF (5 mL) was added 5 ml of aqueous 1 M LiOH. The mixture was stirred at room temperature overnight and then acidified to PH 4 to 5 by cautious addition of aqueous HCl (1N). The solution was extracted with ether (50 mL) three times, dried over anhydrous Na$_2$SO$_4$ and then concentrated to give 2-sulfanylpent-4-enoic acid (compound 25c) 0.6 g.

Compound 25c: $^1$H NMR (400 MHz, CDCl$_3$) δ ppm: 5.75-5.90 (m, 1H), 5.11-5.25 (m, 2H), 3.44-3.53 (m, 1H), 2.63-2.77 (m, 1H), 2.48-2.60 (m, 1H). MS obsd. (ESI$^+$) [(M−H)$^+$]: 131.

Preparation of (4-allyl-5-oxo-1,3-oxathiolan-2-yl)methyl benzoate

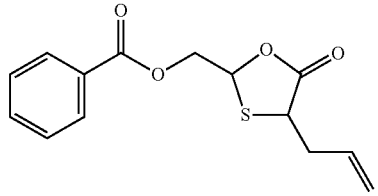

25d

A mixture of 2-sulfanylpent-4-enoic acid (0.6 g, 4.5 mmol) and 2-oxoethyl benzoate (0.9 g, 5.4 mmol) in DCM (10 mL) was stirred at 50° C. for 6 hours. The mixture was allowed to cool to room temperature. Then the reaction mixture was diluted with ethyl acetate, washed with saturated NaHCO$_3$ solution and brine, dried over anhydrous Na$_2$SO$_4$ and then concentrated. The residue was purified by flash column chromatography on silica gel (eluting with 1:10 to 1:5 ethyl acetate in petroleum ether) to afford (4-allyl-5-oxo-1,3-oxathiolan-2-yl)methyl benzoate (compound 25d) 0.6 g as a slightly yellow oil.

Compound 25d: $^1$H NMR (400 MHz, CDCl$_3$) δ ppm: 8.07 (ddd, J=9.35, 8.22, 1.00 Hz, 2H), 7.61 (dd, J=7.40, 1.13 Hz, 1H), 7.43-7.52 (m, 2H), 5.78-5.90 (m, 1H), 5.70-5.78 (m, 1H), 5.14-5.28 (m, 2H), 4.52-4.64 (m, 2H), 4.07-4.17 (m, 1H), 2.86-2.99 (m, 1H), 2.49-2.64 (m, 1H). MS obsd. (ESI$^+$) [(M+H)$^+$]: 279.

Preparation of
4-allyl-5-hydroxy-1,3-oxathiolan-2-yl]methyl
benzoate

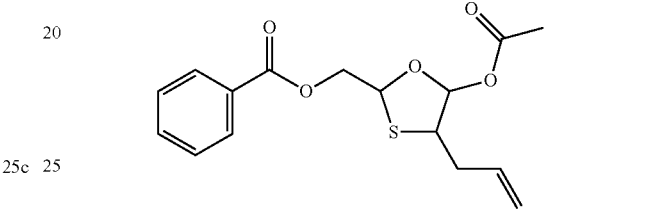

25e

To a solution of (4-allyl-5-oxo-1,3-oxathiolan-2-yl) methyl benzoate (460 mg, 1.7 mmol) in anhydrous THF (5 mL) was added lithium tri-tert-butoxyaluminum hydride (1 M in THF, 2.5 mL, 2.5 mmol) dropwise at −78° C. After being stirred at room temperature for 2 hours, pyridine (0.66 mL, 8.3 mmol), acetic anhydride (0.8 mL, 8.4 mmol) and DMAP (0.6 g, 5 mmol) were added. The reaction mixture was stirred at room temperature overnight and then quenched with saturated NH$_4$Cl solution. The solution was extracted with DCM (50 mL) three times. The organic layer was combined, washed with brine, dried over anhydrous Na$_2$SO$_4$ and then concentrated. The residue was purified by flash column chromatography on silica gel (eluting with 1:10 to 1:5 ethyl acetate in petroleum ether) to afford 4-allyl-5-hydroxy-1,3-oxathiolan-2-yl]methyl benzoate (compound 25e) 0.5 g as a colorless oil. MS obsd. (ESI$^+$) [(M+NH$_4$)$^+$]: 340.

Preparation of [4-allyl-5-(5-amino-2,7-dioxo-6H-thiazolo[4,5-d]pyrimidin-3-yl)-1,3-oxathiolan-2-yl]methyl

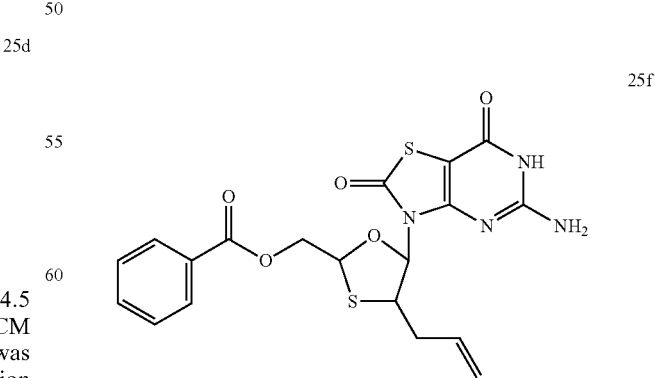

25f

To a solution of 5-amino-7-hydroxy-3H-thiazolo[4,5-d]pyrimidin-2-one (200 mg, 1.1 mmol) in CH$_3$CN (12 mL)

was added BSA (1 mL, 4 mmol). The mixture was heated at 60° C. until a clear solution was formed. The solvent was removed in vacuo. The residue was dissolved in DCM (10 mL). To the above solution were added 4-allyl-5-hydroxy-1,3-oxathiolan-2-yl]methyl benzoate (354 mg, 1.1 mmol) and trimethylsilyl iodide (0.34 mL, 2.4 mmol). After being stirred at room temperature overnight, the reaction mixture was quenched with saturated NaHCO$_3$ solution. The solution was extracted with DCM (50 mL) three times. The organic layer was washed with saturated NaHCO$_3$ solution and brine, dried over anhydrous Na$_2$SO$_4$ and then concentrated. The residue was purified by flash column chromatography on silica gel (eluting with 1:20 methanol in dichloromethane) to afford [4-allyl-5-(5-amino-2,7-dioxo-6H-thiazolo[4,5-d]pyrimidin-3-yl)-1,3-oxathiolan-2-yl]methyl benzoate (compound 25f) 90 mg as a colorless oil. MS obsd. (ESI$^+$) [(M+H)$^+$]: 447.

Preparation of 3-[4-allyl-2-(hydroxymethyl)-1,3-oxathiolan-5-yl]-5-amino-6H-thiazolo[4,5-d]pyrimidine-2,7-dione

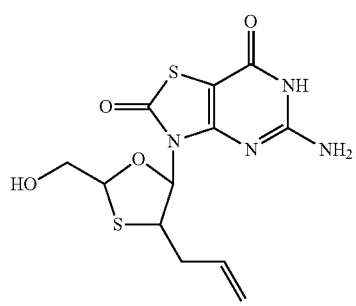

To a solution of [4-allyl-5-(5-amino-2,7-dioxo-6H-thiazolo[4,5-d]pyrimidin-3-yl)-1,3-oxathiolan-2-yl]methyl (90 mg, 0.2 mmol) in methanol (5 ml) was added K$_2$CO$_3$ (111 mg, 0.8 mmol). After being stirred at room temperature overnight, the reaction was neutralized to pH 7 with HOAc and concentrated. The residue was purified by preparative HPLC to afford Example 25-A(the diastereomer 1), Example 25-B(the diastereomer 2), Example 25-C(the diastereomer 3) and Example 25-D(the diastereomer 4) as white powders.

Example 25-A 3.3 mg, $^1$H NMR (400 MHz, CD$_3$OD) δ ppm: 5.91 (d, J=8.78 Hz, 1H), 5.71-5.79 (m, 1H), 5.26 (t, J=4.52 Hz, 1H), 5.10 (dd, J=17.07, 1.51 Hz, 1H), 5.00 (d, J=10.29 Hz, 1H), 4.62-4.69 (m, 1H), 3.77 (d, J=4.52 Hz, 2H), 2.34-2.47 (m, 2H). MS obsd. (ESI$^+$) [(M+H)$^+$]: 343.

Example 25-B 6.3 mg, $^1$H NMR (400 MHz, CD$_3$OD) δ ppm: 6.69 (d, J=6.27 Hz, 1H), 5.86 (t, J=4.52 Hz, 1H), 5.70-5.82 (m, 1H), 4.96-5.09 (m, 2H), 4.11-4.19 (m, 1H), 3.69 (dd, J=4.52, 2.76 Hz, 2H), 2.51-2.59 (m, 1H), 2.21-2.32 (m, 1H). MS obsd. (ESI$^+$) [(M+H)$^+$]: 343.

Example 25-C 4.8 mg, $^1$H NMR (400 MHz, CD$_3$OD) δ ppm: 6.07 (d, J=7.53 Hz, 1H), 5.71-5.83 (m, 2H), 5.14 (dd, J=17.07, 1.51 Hz, 1H), 5.03 (d, J=10.29 Hz, 1H), 4.60-4.67 (m, 1H), 3.74-3.81 (m, 1H), 3.66-3.72 (m, 1H), 2.50-2.59 (m, 1H), 2.39 (dt, J=14.93, 7.34 Hz, 1H). MS obsd. (ESI$^+$) [(M+H)$^+$]: 343.

Example 25-D 3.0 mg, $^1$H NMR (400 MHz, CD$_3$OD) δ ppm: 6.41 (d, J=6.53 Hz, 1H), 5.68-5.77 (m, 1H), 5.32 (s, 1H), 4.96-5.07 (m, 2H), 3.98-4.04 (m, 1H), 3.89 (t, J=4.39 Hz, 2H), 2.47-2.55 (m, 1H), 2.34-2.42 (m, 1H). MS obsd. (ESI$^+$) [(M+H)$^+$]: 343.

Example 26

HEK293-Blue-hTLR-7 Cells Assay

A stable HEK293-Blue-hTLR-7 cell line was purchased from InvivoGen (Cat.#: hkb-ht1r7, San Diego, Calif., USA). These cells were designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was regulated by the NF-κB promoter upon stimulation of human TLR7 for 20 hours. The cell culture supernatant SEAP reporter activity was determined using QUANTI-Blue™ kit (Cat.#: rep-qb1, Invivogen, San Diego, Calif., USA) at a wavelength of 640 nm, a detection medium that turns purple/blue in the presence of alkaline phosphatase.

HEK293-Blue-hTLR7 cells were incubated at a density of 250,000~450,000 cells/mL in a volume of 180 μL in a 96-well plate in Dulbecco's Modified Eagle's medium (DMEM) containing 4.5 g/L glucose, 50 U/mL penicillin, 50 mg/ml streptomycin, 100 mg/mL Normocin, 2 mM L-glutamine, 10% (v/v) heat-inactivated fetal bovine serum for 24 h. Then the HEK293-Blue-hTLR-7 cells were incubated with addition of 20 μL test compound in a serial dilution in the presence of final DMSO at 1% and perform incubation under 37° C. in a CO$_2$ incubator for 20 hours. Then 20 μL of the supernatant from each well was incubated with 180 μL Quanti-blue substrate solution at 37° C. for 2 h and the absorbance was read at 620~655 nm using a spectrophotometer. The signalling pathway that TLR7 activation leads to downstream NF-κB activation has been widely accepted, and therefore similar reporter assay was also widely used for evaluating TLR7 agonist (Tsuneyasu Kaisho and Takashi Tanaka, Trends in Immunology, Volume 29, Issue 7, July 2008, Pages 329.sci; Hiroaki Hemmi et al, Nature Immunology 3, 196-200 (2002).

The TLR7 agonism activity in HEK293-hTLR-7 assay of compounds of present invention is listed in Table 1. The compounds of Example 1-25 were found to have EC$_{50}$ of about 4.5 μM to about 180 μM.

TABLE 1

| Activity of Compounds in HEK293- hTLR-7 assay | |
|---|---|
| Example No. | HEK293- hTLR-7 EC$_{50}$ (μM) |
| 1 | 97 |
| 2-A | 125.3 |
| 4-A | 7.9 |
| 4-B | 306 |

TABLE 1-continued

Activity of Compounds in HEK293- hTLR-7 assay

| Example No. | HEK293- hTLR-7 EC$_{50}$ (μM) |
|---|---|
| 7-A | 61.7 |
| 8-A | 16.5 |
| 9-A | 10.0 |
| 9-B | 159.8 |
| 10-A | 7.6 |
| 10-B | 122.4 |
| 13-A | 151.4 |
| 14-A | 54.3 |
| 15-A | 16.7 |
| 16-A | 46.5 |
| 17-A | 63.3 |
| 17-B | 93.6 |
| 18-A | 29.0 |
| 19-A | 32.9 |
| 20-A | 33.9 |
| 21-A | 53.9 |
| 22-A | 4.7 |
| 23-A | 4.5 |
| 23-B | 31.5 |
| 24-A | 10.1 |
| 25-A | 177.5 |

Example 27

Metabolism of Prodrugs of Formula (I)

A study was undertaken to evaluate the metabolic conversion of prodrugs of formula (Ia) to compounds of formula (I) of the present invention. The produgs of formula (Ia) can be metabolized to the active compound of formula (I) and other compounds of the invention in the body if they are served as prodrugs. Hepatocytes are often used to assess the degree of metabolic conversion of prodrugs in the body of animal or human.

A study was undertaken to evaluate the metabolic conversion of prodrugs, Example 5-A, Example 6-A, Example 11-A and Example 12-A, to the corresponding active forms, Example 4-A and Example 10-A, in the presence of human hepatocytes. The formation of active forms, Example 4-A and Example 10-A, were monitored in the study. For comparison, the metabolic conversion of famciclovir to penciclovir was also assessed.

Hepatocytes Suspension

Cryopreserved hepatocytes plating medium (Cat.#: PY-HMD-01) was purchased from RILD Research Institute for Liver Diseases (Shanghai) Co. Ltd. Cryopreserved human hepatocyte (Cat.#: X008005, Lot#:VRR) was purchased from In Vitro Technologies (Baltimore, Md.).

The stock hepatocyte suspension was prepared from cryopreserved hepatocytes in plating medium at the concentration of 1.8×10$^6$ cells/mL.

Working Solutions of Compounds

Compounds were dissolved in DMSO to make 50 mM stock solutions. 10 μL of the stock solution was diluted to 5 mL plating medium to get a 100 μM working solution.

Incubations

Reaction suspensions were prepared in 24-well cell culture plate by mixing 200 μL of hepatocytes suspension (Cyno or human) and 200 μL of working solution. The final incubation contained 0.9×10$^6$ cells/mL and 50 μM compound. The above mixtures were incubated at 37° C. in a humidified 5% CO$_2$ atmosphere, with a 150 rpm shaking.

Preparation of Samples for Analysis

After 180 min of incubation, 200 μL of the incubation mixture was transferred to 1.5 mL tube and quenched with 400 μL stop solution (ice-cold acetonitrile with 0.2 μM Tolbutamide as internal standard). The samples were centrifuged at 12000 rpm for 10 minutes and the resultant supernatants were subjected to LC-MS/MS analysis.

The calibration curves were prepared in the following way. To a 200 μL of cell suspension (cell density of 1.8 million cells/mL), 198 μL of hepatocyte plating medium and 2 μL of the appropriate concentration of the compound in DMSO were added. Samples were mixed thoroughly and 200 μL of the mixture was transferred to 400 uL of the stop solution (see above). The standard curve range is from 1 μM to 25 μM.

Bioanalysis

The compounds were quantified on an API5500 LC-MC/MC instrument in the ESI-Positive MRM mode. The results of prodrug conversion and metabolite generation are summarized in Table 2.

TABLE 2

Concentration of the metabolites formed in human hepatocytes after 3-hour incubation of 50 μM of prodrugs.

| Example No. | Metabolized Product | Product Concentration in human hepatocytes (μM) |
|---|---|---|
| 5-A | 4-A | 9.6 |
| 6-A | 4-A | 12.9 |
| 11-A | 10-A | 11.3 |
| 12-A | 10-A | 18 |
| Famciclovir | Penciclovir | 23.5 |

In human hepatocytes, compounds of Example 5-A, Example 6-A, Example 11-A and Example 12-A as well as famciclovir were metabolized to yield the corresponding active metabolites of Example 4-A, Example 10-A and penciclovir, respectively.

Example 28

TLR7 Agonist Example 4-A Activates Murine TLR7

The potency of the TLR7 agonist Example 4-A was assessed in murine TLR7 activation using a stable HEK293-Blue-mTLR7 cell line purchased from InvivoGen (Cat.#: hkb-mt1r7, San Diego, Calif., USA). Similar to the HEK293-Blue-hTLR7 as described in Example 26, the HEK293-Blue-mTLR7 was designed for studying the stimulation of murine TLR7 by monitoring the activation of NF-κB. A SEAP reporter gene was placed under the control of the IFN-β minimal promoter fused to five NF-κB and AP-1-binding sites. SEAP expression was induced by the activation of NF-κB and AP-1 upon stimulation of murine TLR7 with TLR7 ligands. SEAP expression in cell culture supernatant was determined using QUANTI-Blue™ kit (Cat.#: rep-qb1, Invivogen, San Diego, Ca, USA) at a wavelength of 640 nm, a detection medium that turns purple/blue in the presence of alkaline phosphatase.

HEK293-Blue-mTLR7 cells were incubated at a density of 250,000~450,000 cells/mL in a volume of 180 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum for 24 h. Then the HEK293-Blue-mTLR-7 cells were incubated with 20 μL test compound in a serial dilution in the presence of final DMSO at 1% at 37° C. in a CO$_2$ incubator for 20 hours. Then 20 μL of the supernatant from each well was incubated with 180 µl Quanti-blue substrate solution at 37° C. for 2 hours and the absorbance was read at 640 nm using a spectrophotometer.

As shown in FIG. 1, Example 4-A activates murine TLR7 in a dose dependent manner with an EC50 of 7.8 µM.

Example 29

Example 6-A Reduces HBV DNA and HBsAg in AAV-HBV Model

Example 6-A was evaluated for its in vivo antiviral efficacy using an AAV-HBV mouse model. This mouse model for HBV infection was generated by injecting C57BL/6 mice with a recombinant adeno-associated virus (AAV) carrying a replicable HBV (hepatitis B virus) genome (AAV-HBV). In 3 weeks post infection, high levels of HBV viral markers, such as HBV genomic DNA and HBsAg (HBV surface antigen), was detected in the sera of infected mice. With persistent HBV viremia and fully competent immune system, the AAV-HBV model is suitable for investigating the in vivo efficacy of Example 6-A.

To establish the AAV-HBV model, a total of fifteen 4-week old male C57BL/6 mice, specific pathogen free, were purchased from Shanghai Laboratory Animal Center of Chinese Academy of Sciences (SLAC) and housed in an animal care facility in individually ventilated cages under controlled temperature and light conditions following the Institutional Animal Care guidelines. AAV-HBV virus stock was available from Beijing FivePlus Molecular Medicine Institute (Beijing, China). C57BL/6 mice were injected with 200 µL of recombinant virus in saline buffer through tail vein injection. The mice were bled on day 14 post injection to monitor HBsAg, HBeAg, and HBV genomic DNA in serum. On day 29 post injection, the fifteen mice were randomly recruited into 3 groups based on their HBV biomarker levels, and started to receive treatments, as shown in Table 3.

TABLE 3

In vivo study in AAV-HBV mouse model

| | | Treatment | | |
|---|---|---|---|---|
| Group # | Mice # | Compound | Dose (mg/kg) | Drug delivery |
| 1 | 5 | Vehicle | 0 | PO, QOD, 42D |
| 2 | 5 | Example 6-A | 30 | |
| 3 | 5 | Example 6-A | 100 | |

Mice in group 1 were treated with vehicle placebo (2% Klucel LF, 0.1% Polysorbate 80, and 0.1% Parabens in water); mice in group 2 and 3 were treated with Example 6-A at 30 mg/kg and 100 mg/kg respectively, every other day (QOD). All the mice were orally dosed for a total of 6 weeks. Serum samples were collected twice a week to monitor HBV biomarkers. Serum HBsAg was measured using CLIA kits (Autobio Diagnostics Co., Ltd, Zhengzhou, China) according to the manufacturer's instructions. The lower limit of detection for HBsAg was 0.1 ng/mL. Serum dilution of 500-fold (for HBsAg) was used to obtain values within the linear range of the standard curve. Serum HBV DNA was extracted using a MagNA Pure 96 DNA and Viral NA Small Volume Kit (Roche) following the manufacturer's instructions. The DNA samples were analyzed by real-time quantitative PCR (qPCR) using a HBV-specific primer and probe set for specific amplification and detection of a 128 bp HBV genome region from the nucleotide 2969 to 3096.

Figure 2:
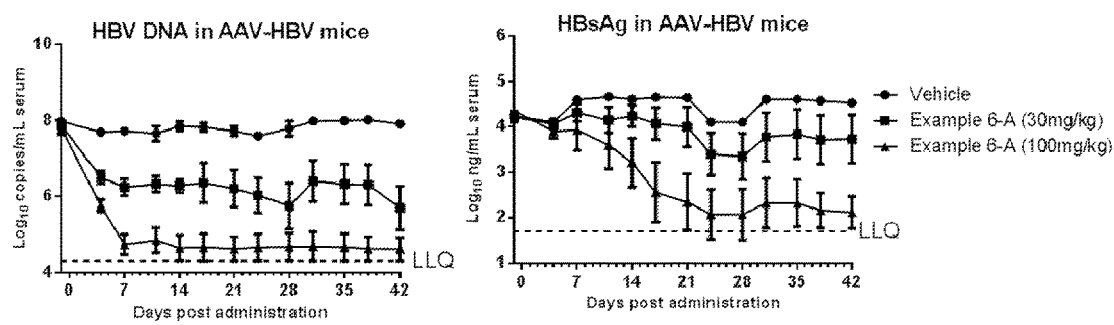
FIG. 2: HBV DNA and HBsAg in the AAV-HBV infected mice treated with Vehicle, a low dose of Example 6-A at 30 mg/kg, and a high dose of Example 6-A at 100 mg/kg. The treatment started after the mice were infected with AAV-HBV for 29 days. They were given the treatment for 42 days, and HBV DNA and HBsAg in mouse serum were measured on the indicated time points by RT-qPCR and HBsAg CLIA respectively. The results were presented as mean±SEM. LLQ: lower limit of quantification.

As shown in FIG. 2, after the 6-week treatment, Example 6-A at 30 mg/kg induced more than 2-log reduction in HBV DNA and 0.8-log reduction in HBsAg. At a higher dose of 100 mg/kg, Example 6-A reduced HBV DNA by more than 3-log and HBsAg by 2.4-log at the end of the treatment. The results of this study clearly demonstrate the in vivo antiviral efficacy of Example 6-A and underscore the potential of compounds of this invention to develop novel therapy for infectious diseases.

The invention claimed is:

1. A compound of formula (I),

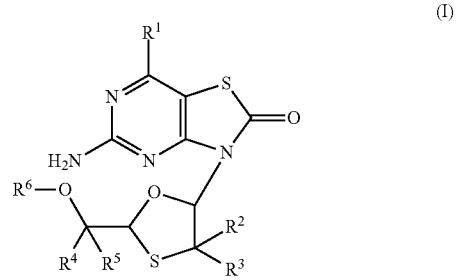

wherein
$R^1$ is hydroxy;
$R^2$ and $R^3$ are independently selected from hydrogen, $C_{2-6}$alkenyl, $C_{3-7}$cycloalkyl and $C_{1-6}$alkyl;
$R^4$ and $R^5$ are independently selected from hydrogen, $C_{1-6}$alkyl, $C_{3-7}$cycloalkyl, $C_{3-7}$cycloalkyl, $C_{2-6}$alkynyl, $C_{2-6}$alkenyl, $C_{2-6}$alkynyl, phenyl and thiophenyl; and
$R^6$ is hydrogen, $C_{1-6}$alkoxylcarbonyl or $C_{1-6}$alkylcarbonyl;
or a pharmaceutically acceptable salt, enantiomer or diastereomer thereof.

2. A compound according to claim 1, wherein
$R^1$ is hydroxy;
$R^2$ and $R^3$ are independently selected from hydrogen, methyl, cyclopropyl and allyl;
$R^4$ and $R^5$ are independently selected from hydrogen, methyl, ethyl, n-propyl, n-butyl, isobutyl, cyclopropyl, ethynyl, 1-propynyl, 2-cyclopropylethynyl, allyl, phenyl, 3-thiophenyl and 2-thiophenyl; and
$R^6$ is hydrogen, ethoxycarbonyl or acetyl;
or a pharmaceutically acceptable salt, enantiomer or diastereomer thereof.

3. A compound according to claim 1, wherein
$R^1$ is hydroxy;
$R^2$ and $R^3$ are independently selected from hydrogen, $C_{2-6}$alkenyl and $C_{1-6}$alkyl;
$R^4$ and $R^5$ are independently selected from hydrogen, $C_{1-6}$alkyl, $C_{3-7}$cycloalkyl, $C_{3-7}$cycloalkyl, $C_{2-6}$alkynyl, $C_{2-6}$alkenyl, $C_{2-6}$alkynyl and 2-thiophenyl; and
$R^6$ is hydrogen or $C_{1-6}$alkylcarbonyl;
or a pharmaceutically acceptable salt, enantiomer or diastereomer thereof.

4. A compound according to claim 1, wherein
$R^1$ is hydroxy;
$R^2$ and $R^3$ are independently selected from hydrogen, methyl and allyl;
$R^4$ and $R^5$ are independently selected from hydrogen, methyl, ethyl, n-propyl, n-butyl, isobutyl, cyclopropyl, ethynyl, 1-propynyl, 2-cyclopropylethynyl, allyl and 2-thiophenyl; and R⁶ is hydrogen or acetyl;
or a pharmaceutically acceptable salt, enantiomer or diastereomer thereof.

5. A compound or a pharmaceutically acceptable salt, enantiomer or diastereomer according to claim 1, wherein R² and R³ are independently selected from hydrogen and C₁₋₆alkyl.

6. A compound or a pharmaceutically acceptable salt, enantiomer or diastereomer according to claim 1, wherein R² and R³ are independently selected from hydrogen and methyl.

7. A compound or a pharmaceutically acceptable salt, enantiomer or diastereomer according to claim 1, wherein R⁴ and R⁵ are independently selected from hydrogen, C₁₋₆alkyl, C₃₋₇cycloalkyl, C₂₋₆alkenyl, C₂₋₆alkynyl and 2-thiophenyl.

8. A compound or a pharmaceutically acceptable salt, enantiomer or diastereomer according to claim 1, wherein R⁴ and R⁵ are independently selected from hydrogen, methyl, ethyl, n-propyl, n-butyl, cyclopropyl, ethynyl, 1-propynyl, allyl and 2-thiophenyl.

9. A compound or a pharmaceutically acceptable salt, enantiomer or diastereomer according to claim 1, wherein R⁶ is hydrogen.

10. A compound according to claim 1, wherein
R¹ is hydroxy;
R² and R³ are independently selected from hydrogen and C₁₋₆alkyl;
R⁴ and R⁵ are independently selected from hydrogen, C₁₋₆alkyl, C₃₋₇cycloalkyl, C₂₋₆alkenyl, C₂₋₆alkynyl and 2-thiophenyl; and
R⁶ is hydrogen;
or a pharmaceutically acceptable salt, enantiomer or diastereomer thereof.

11. A compound according to claim 10, wherein
R¹ is hydroxy;
R² and R³ are independently selected from hydrogen and methyl;
R⁴ and R⁵ are independently selected from hydrogen, methyl, ethyl, n-propyl, n-butyl, cyclopropyl, ethynyl, 1-propynyl, allyl and 2-thiophenyl; and
R⁶ is hydrogen;
or a pharmaceutically acceptable salt, enantiomer or diastereomer thereof.

12. A compound according to claim 1 selected from:
5-Amino-3-[2-(hydroxymethyl)-1,3-oxathiolan-5-yl]-6H-thiazolo[4,5-d] pyrimidine-2,7-dione;
5-Amino-3-[(2S)-2-(hydroxymethyl)-1,3-oxathiolan-5-yl]-6H-thiazolo[4,5-d] pyrimidine-2,7-dione;
5-Amino-3-[(2S,5R)-2-[cyclopropyl(hydroxy)methyl]-1,3-oxathiolan-5-yl]-6H-thiazolo[4,5-d]pyrimidine-2,7-dione;
[[(2S,5R)-5-(5-Amino-2,7-dioxo-6H-thiazolo[4,5-d]pyrimidin-3-yl)-1,3-oxathiolan-2-yl]-cyclopropylmethyl] acetate;
5-Amino-3-[(2S,5R)-2-(1-hydroxypropyl)-1,3-oxathiolan-5-yl]-6H-thiazolo[4,5-d] pyrimidine-2,7-dione;
5-Amino-3-[(2S,5R)-2-(1-hydroxybutyl)-1,3-oxathiolan-5-yl]-6H-thiazolo[4,5-d]pyrimidine-2,7-dione;
5-Amino-3-[(2S,5R)-2-(1-hydroxybut-2-ynyl)-1,3-oxathiolan-5-yl]-6H-thiazolo[4,5-d]pyrimidine-2,7-dione;
1-[(2S,5R)-5-(5-Amino-2,7-dioxo-6H-thiazolo[4,5-d]pyrimidin-3-yl)-1,3-oxathiolan-2-yl] but-2-ynyl acetate;
5-Amino-3-[(2S,5R)-2-(3-cyclopropyl-1-hydroxy-prop-2-ynyl)-1,3-oxathiolan-5-yl]-6H-thiazolo[4,5-d]pyrimidine-2,7-dione;
5-Amino-3-[(2S,5R)-2-(1-hydroxyprop-2-ynyl)-1,3-oxathiolan-5-yl]-6H-thiazolo[4,5-d]pyrimidine-2,7-dione;
5-Amino-3-[(2S,5R)-2-(1-hydroxyethyl)-1,3-oxathiolan-5-yl]-6H-thiazolo[4,5-d]pyrimidine-2,7-dione;
5-Amino-3-[(2S,5R)-2-(1-hydroxy-3-methyl-butyl)-1,3-oxathiolan-5-yl]-6H-thiazolo[4,5-d]pyrimidine-2,7-dione;
5-Amino-3-[(2S,5R)-2-(1-hydroxybut-3-enyl)-1,3-oxathiolan-5-yl]-6H-thiazolo[4,5-d]pyrimidine-2,7-dione;
5-Amino-3-[(2S,5R)-2-(1-hydroxypentyl)-1,3-oxathiolan-5-yl]-6H-thiazolo[4,5-d] pyrimidine-2,7-dione;
5-amino-3-[(2S,5R)-2-[hydroxy(2-thienyl)methyl]-1,3-oxathiolan-5-yl]-6H-thiazolo[4,5-d]pyrimidine-2,7-dione;
5-Amino-3-[(2S,4S)-2-(hydroxymethyl)-4-methyl-1,3-oxathiolan-5-yl]-6H-thiazolo[4,5-d]pyrimidine-2,7-dione;
5-Amino-3-[(4S)-2-[(1S)-1-hydroxypropyl]-4-methyl-1,3-oxathiolan-5-yl]-6H-thiazolo[4,5-d]pyrimidine-2,7-dione;
5-Amino-3-[(2S,4S)-2-[cyclopropyl(hydroxy)methyl]-4-methyl-1,3-oxathiolan-5-yl]-6H-thiazolo[4,5-d]pyrimidine-2,7-dione;
5-Amino-3-[(4S)-2-(1-hydroxybut-2-ynyl)-4-methyl-1,3-oxathiolan-5-yl]-6H-thiazolo[4,5-d]pyrimidine-2,7-dione; and
3-[4-Allyl-2-(hydroxymethyl)-1,3-oxathiolan-5-yl]-5-amino-6H-thiazolo[4,5-d]pyrimidine-2,7-dione;
or a pharmaceutically acceptable salt, enantiomer or diastereomer thereof.

13. A compound according to claim 12 selected from:
5-Amino-3-[(2S)-2-(hydroxymethyl)-1,3-oxathiolan-5-yl]-6H-thiazolo[4,5-d]pyrimidine-2,7-dione;
5-Amino-3-[(2S,5R)-2-[cyclopropyl(hydroxy)methyl]-1,3-oxathiolan-5-yl]-6H-thiazolo[4,5-d]pyrimidine-2,7-dione;
5-Amino-3-[(2S,5R)-2-(1-hydroxypropyl)-1,3-oxathiolan-5-yl]-6H-thiazolo[4,5-d] pyrimidine-2,7-dione;
5-Amino-3-[(2S,5R)-2-(1-hydroxybutyl)-1,3-oxathiolan-5-yl]-6H-thiazolo[4,5-d]pyrimidine-2,7-dione;
5-Amino-3-[(2S,5R)-2-(1-hydroxybut-2-ynyl)-1,3-oxathiolan-5-yl]-6H-thiazolo[4,5-d]pyrimidine-2,7-dione;
5-Amino-3-[(2S,5R)-2-(1-hydroxyprop-2-ynyl)-1,3-oxathiolan-5-yl]-6H-thiazolo[4,5-d]pyrimidine-2,7-dione;
5-Amino-3-[(2S,5R)-2-(1-hydroxyethyl)-1,3-oxathiolan-5-yl]-6H-thiazolo[4,5-d]pyrimidine-2,7-dione;
5-Amino-3-[(2S,5R)-2-(1-hydroxybut-3-enyl)-1,3-oxathiolan-5-yl]-6H-thiazolo[4,5-d]pyrimidine-2,7-dione;
5-Amino-3-[(2S,5R)-2-(1-hydroxypentyl)-1,3-oxathiolan-5-yl]-6H-thiazolo[4,5-d] pyrimidine-2,7-dione;
5-amino-3-[(2S,5R)-2-[hydroxy(2-thienyl)methyl]-1,3-oxathiolan-5-yl]-6H-thiazolo[4,5-d]pyrimidine-2,7-dione;
5-Amino-3-[(2S,4S)-2-(hydroxymethyl)-4-methyl-1,3-oxathiolan-5-yl]-6H-thiazolo[4,5-d]pyrimidine-2,7-dione;
5-Amino-3-[(4S)-2-[(1S)-1-hydroxypropyl]-4-methyl-1,3-oxathiolan-5-yl]-6H-thiazolo[4,5-d]pyrimidine-2,7-dione; and
5-Amino-3-[(2S,4S)-2-[cyclopropyl(hydroxy)methyl]-4-methyl-1,3-oxathiolan-5-yl]-6H-thiazolo[4,5-d]pyrimidine-2,7-dione;
or a pharmaceutically acceptable salt, enantiomer or diastereomer thereof.

14. A compound of formula (Ia),

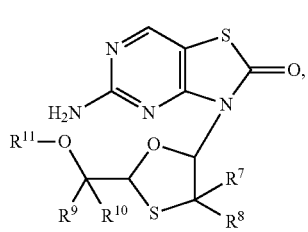

(Ia)

wherein
R$^7$ and R$^8$ are independently selected from hydrogen, C$_{2-6}$alkenyl and C$_{1-6}$alkyl;
R$^9$ and R$^{10}$ are independently selected from hydrogen, C$_{1-6}$alkyl, C$_{3-7}$cycloalkyl, C$_{3-7}$cycloalkyl, C$_{2-6}$alkynyl, C$_{2-6}$alkenyl, C$_{2-6}$alkynyl and 2-thiophenyl; and
R$^{11}$ is hydrogen or C$_{1-6}$alkylcarbonyl;
or a pharmaceutically acceptable salt, enantiomer or diastereomer thereof.

15. A compound according to claim 14, wherein
R$^7$ and R$^8$ are independently selected from hydrogen, methyl and allyl;
R$^9$ and R$^{10}$ are independently selected from hydrogen, methyl, ethyl, n-propyl, n-butyl, isobutyl, cyclopropyl, ethynyl, 1-propynyl, 2-cyclopropylethynyl, allyl and 2-thiophenyl; and
R$^{11}$ is hydrogen or acetyl;
or a pharmaceutically acceptable salt, enantiomer or diastereomer thereof.

16. A compound according to claim 14, wherein
R$^7$ and R$^8$ are hydrogen;
R$^9$ and R$^{10}$ are independently selected from hydrogen, C$_{2-6}$alkynyl and C$_{3-7}$cycloalkyl; and
R$^{11}$ is hydrogen or C$_{1-6}$alkylcarbonyl;
or a pharmaceutically acceptable salt, enantiomer or diastereomer thereof.

17. A compound according to claim 14, wherein
R$^7$ and R$^8$ are hydrogen;
R$^9$ and R$^{10}$ are independently selected from hydrogen, 1-propynyl and cyclopropyl; and
R$^{11}$ is hydrogen or acetyl;
or a pharmaceutically acceptable salt, enantiomer or diastereomer thereof.

18. A compound according to claim 14 selected from:
5-Amino-3-[(2S)-2-(hydroxymethyl)-1,3-oxathiolan-5-yl]thiazolo[4,5-d] pyrimidin-2-one;
5-Amino-3-[(2S,5R)-2-[-cyclopropyl(hydroxy)methyl]-1,3-oxathiolan-5-yl]thiazolo[4,5-d]pyrimidin-2-one;
[[(2S,5R)-5-(5-Amino-2-oxo-thiazolo[4,5-d]pyrimidin-3-yl)-1,3-oxathiolan-2-yl]-cyclopropyl-methyl] acetate;
5-Amino-3-[(2S,5R)-2-(1-hydroxybut-2-ynyl)-1,3-oxathiolan-5-yl]thiazolo[4,5-d]pyrimidin-2-one; and
1-[(2S,5R)-5-(5-Amino-2-oxo-thiazolo[4,5-d]pyrimidin-3-yl)-1,3-oxathiolan-2-yl]but-2-ynyl acetate;
or a pharmaceutically acceptable salt, enantiomer or diastereomer thereof.

19. A process for the preparation of a compound or a pharmaceutically acceptable salt, enantiomer or diastereomer according to claim 1 or 14 comprising:

(a) the reaction of a compound of formula (IX),

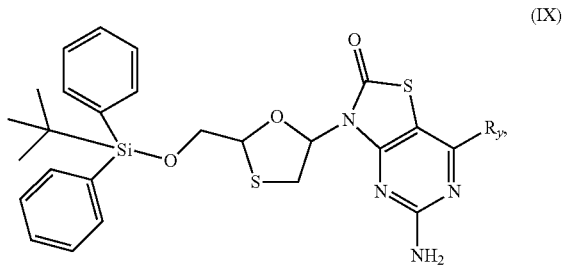

(IX)

with a fluoride reagent, wherein R$_y$ is hydrogen or hydroxy;

(b) the reaction of a compound of formula (XV),

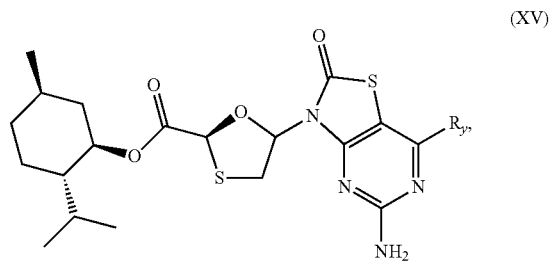

(XV)

with a reductant, wherein R$_y$ is hydrogen or hydroxy;

(c) the reaction of a compound of formula (XIX),

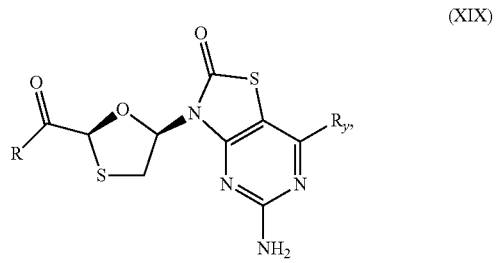

(XIX)

with a reductant, wherein R$_y$ is hydrogen or hydroxy; and R is R$^4$, R$^5$, R$^9$ or R$^{10}$;

(d) the reaction of a compound of formula (XXII),

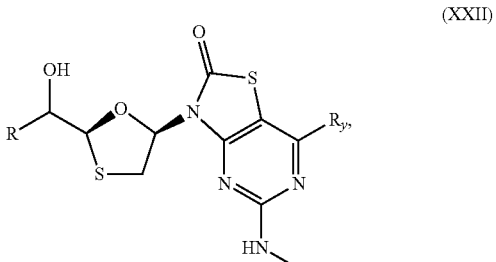

(XXII)

with an acid, wherein R$_y$ is hydrogen or hydroxy; and R is R$^4$, R$^5$, R$^9$ or R$^{10}$;

(e) the reaction of a compound of formula (XXIII),

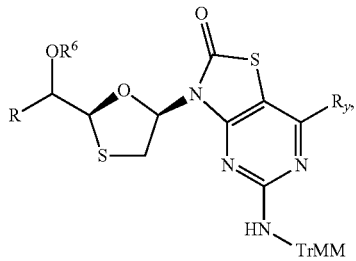

(XXIII)

with an acid, wherein $R_y$ is hydrogen or hydroxy; and R is $R^4$, $R^5$, $R^9$ or $R^{10}$; or (f) the reaction of a compound of formula (XXIX),

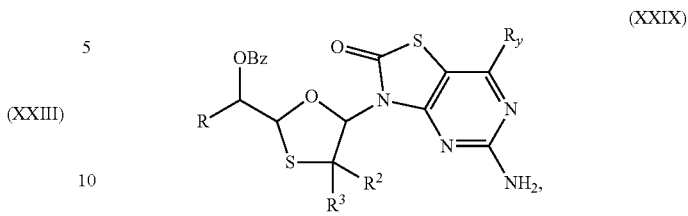

(XXIX)

with a base, wherein $R_y$ is hydrogen or hydroxy; and R is $R^4$, $R^5$, $R^9$ or $R^{10}$.

20. A pharmaceutical composition comprising a compound or a pharmaceutically acceptable salt, enantiomer or diastereomer thereof in accordance with claim 1 and a therapeutically inert carrier.

21. A pharmaceutical composition comprising a compound or a pharmaceutically acceptable salt, enantiomer or diastereomer thereof in accordance with claim 14 and a therapeutically inert carrier.

* * * * *